United States Patent
Mensinger et al.

(10) Patent No.: US 11,102,306 B2
(45) Date of Patent: Aug. 24, 2021

(54) SYSTEMS AND METHODS FOR PROCESSING, TRANSMITTING AND DISPLAYING SENSOR DATA

(71) Applicant: DexCom, Inc., San Diego, CA (US)

(72) Inventors: Michael Robert Mensinger, San Diego, CA (US); John Michael Dobbles, San Diego, CA (US); Apurv Ullas Kamath, San Diego, CA (US); Beat Stadelmann, San Diego, CA (US); Deborah M. Ruppert, San Diego, CA (US); Nasser Salamati, San Diego, CA (US); Richard C. Yang, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 16/937,440

(22) Filed: Jul. 23, 2020

(65) Prior Publication Data

US 2020/0358855 A1    Nov. 12, 2020

Related U.S. Application Data

(63) Continuation of application No. 15/673,307, filed on Aug. 9, 2017, which is a continuation of application
(Continued)

(51) Int. Cl.
*A61B 5/00* (2006.01)
*H04L 29/08* (2006.01)
(Continued)

(52) U.S. Cl.
CPC .......... *H04L 67/125* (2013.01); *A61B 5/0022* (2013.01); *A61B 5/7445* (2013.01);
(Continued)

(58) Field of Classification Search
None
See application file for complete search history.

(56) References Cited

U.S. PATENT DOCUMENTS

| 52,641 A | 2/1866 | Gregg et al. |
|---|---|---|
| 62,334 A | 2/1867 | Berner et al. |
| (Continued) | | |

FOREIGN PATENT DOCUMENTS

| CA | 2127172 C | 7/1998 |
|---|---|---|
| EP | 0098592 A2 | 1/1984 |
| (Continued) | | |

OTHER PUBLICATIONS

US 7,530,950 B2, 05/2009, Brister et al. (withdrawn)
(Continued)

*Primary Examiner* — Etsub D Berhanu
(74) *Attorney, Agent, or Firm* — Knobbe Martens Olson & Bear LLP

(57) ABSTRACT

Systems and methods for continuous measurement of an analyte in a host are provided. The system generally includes a continuous analyte sensor configured to continuously measure a concentration of analyte in a host and a sensor electronics module physically connected to the continuous analyte sensor during sensor use, wherein the sensor electronics module is further configured to directly wirelessly communicate displayable sensor information to a plurality of different types of display devices.

24 Claims, 21 Drawing Sheets

Related U.S. Application Data

No. 12/880,015, filed on Sep. 10, 2010, now abandoned, which is a continuation of application No. 12/390,304, filed on Feb. 20, 2009, now Pat. No. 9,143,569.

(60) Provisional application No. 61/030,499, filed on Feb. 21, 2008.

(51) Int. Cl.
*G16H 15/00* (2018.01)
*G16H 40/63* (2018.01)
*G16H 40/67* (2018.01)
*A61B 5/145* (2006.01)

(52) U.S. Cl.
CPC .............. *G16H 40/63* (2018.01); *G16H 40/67* (2018.01); *A61B 5/14532* (2013.01); *Y02A 90/10* (2018.01)

(56) References Cited

U.S. PATENT DOCUMENTS

| | | |
|---|---|---|
| 65,604 A | 6/1867 | Heller et al. |
| 3,210,578 A | 10/1965 | Sherer |
| 3,219,533 A | 11/1965 | Mullins |
| 3,381,371 A | 5/1968 | Russell |
| 3,775,182 A | 11/1973 | Patton et al. |
| 3,826,244 A | 7/1974 | Salcman et al. |
| 3,837,339 A | 9/1974 | Aisenberg et al. |
| 3,874,850 A | 4/1975 | Sorensen et al. |
| 3,898,984 A | 8/1975 | Mandel et al. |
| 3,943,918 A | 3/1976 | Lewis |
| 3,957,613 A | 5/1976 | Macur |
| 3,964,974 A | 6/1976 | Banauch et al. |
| 3,979,274 A | 9/1976 | Newman |
| 4,024,312 A | 5/1977 | Korpman |
| 4,040,908 A | 8/1977 | Clark, Jr. |
| 4,052,754 A | 10/1977 | Homsy |
| 4,073,713 A | 2/1978 | Newman |
| 4,172,770 A | 10/1979 | Semersky et al. |
| 4,197,840 A | 4/1980 | Beck et al. |
| 4,206,755 A | 6/1980 | Klein |
| 4,215,703 A | 8/1980 | Willson |
| 4,240,438 A | 12/1980 | Updike et al. |
| 4,245,634 A | 1/1981 | Albisser et al. |
| 4,253,469 A | 3/1981 | Aslan |
| 4,255,500 A | 3/1981 | Hooke |
| 4,259,540 A | 3/1981 | Sabia |
| 4,319,578 A | 3/1982 | Enger |
| 4,374,013 A | 2/1983 | Enfors |
| 4,388,166 A | 6/1983 | Suzuki et al. |
| 4,403,984 A | 9/1983 | Ash et al. |
| 4,442,841 A | 4/1984 | Uehara et al. |
| 4,477,314 A | 10/1984 | Richter et al. |
| 4,494,950 A | 1/1985 | Fischell |
| RE31,916 E | 6/1985 | Oswin et al. |
| 4,534,355 A | 8/1985 | Potter |
| 4,535,786 A | 8/1985 | Kater |
| 4,554,927 A | 11/1985 | Fussell |
| 4,655,880 A | 4/1987 | Liu |
| 4,663,824 A | 5/1987 | Kenmochi |
| 4,675,656 A | 6/1987 | Narcisse |
| 4,684,558 A | 8/1987 | Keusch et al. |
| 4,702,732 A | 10/1987 | Powers et al. |
| 4,703,756 A | 11/1987 | Gough et al. |
| 4,731,726 A | 3/1988 | Allen, III |
| 4,750,496 A | 6/1988 | Reinhart et al. |
| 4,753,652 A | 6/1988 | Langer et al. |
| 4,757,022 A | 7/1988 | Shults et al. |
| 4,777,953 A | 10/1988 | Ash et al. |
| 4,786,394 A | 11/1988 | Enzer et al. |
| 4,787,398 A | 11/1988 | Garcia et al. |
| 4,805,625 A | 2/1989 | Wyler |
| 4,810,243 A | 3/1989 | Howson |
| 4,810,470 A | 3/1989 | Burkhardt et al. |
| 4,820,281 A | 4/1989 | Lawler, Jr. |
| 4,823,808 A | 4/1989 | Clegg et al. |
| 4,832,034 A | 5/1989 | Pizziconi et al. |
| 4,852,573 A | 8/1989 | Kennedy |
| 4,854,322 A | 8/1989 | Ash et al. |
| 4,858,615 A | 8/1989 | Meinema |
| 4,871,440 A | 10/1989 | Nagata et al. |
| 4,883,057 A | 11/1989 | Broderick |
| 4,889,744 A | 12/1989 | Quaid |
| 4,890,621 A | 1/1990 | Hakky |
| 4,902,294 A | 2/1990 | Gosserez |
| 4,907,857 A | 3/1990 | Giuliani et al. |
| 4,919,141 A | 4/1990 | Zier et al. |
| 4,925,444 A | 5/1990 | Orkin et al. |
| 4,927,407 A | 5/1990 | Dorman |
| 4,927,516 A | 5/1990 | Yamaguchi et al. |
| 4,944,299 A | 7/1990 | Silvian |
| 4,946,439 A | 8/1990 | Eggers |
| 4,953,552 A | 9/1990 | Demarzo |
| 4,974,592 A | 12/1990 | Branco |
| 4,974,929 A | 12/1990 | Curry |
| 4,984,929 A | 1/1991 | Rock et al. |
| 4,989,607 A | 2/1991 | Keusch et al. |
| 4,992,794 A | 2/1991 | Brouwers |
| 4,994,167 A | 2/1991 | Shults et al. |
| 5,007,929 A | 4/1991 | Quaid |
| 5,033,864 A | 7/1991 | Lasecki et al. |
| 5,034,112 A | 7/1991 | Murase et al. |
| 5,050,612 A | 9/1991 | Matsumura |
| 5,055,171 A | 10/1991 | Peck |
| 5,059,654 A | 10/1991 | Hou et al. |
| 5,067,491 A | 11/1991 | Taylor, II et al. |
| 5,088,981 A | 2/1992 | Howson et al. |
| 5,096,669 A | 3/1992 | Lauks et al. |
| 5,097,834 A | 3/1992 | Skrabal |
| 5,101,814 A | 4/1992 | Palti |
| 5,137,028 A | 8/1992 | Nishimura |
| 5,165,407 A | 11/1992 | Wilson et al. |
| 5,178,142 A | 1/1993 | Harjunmaa et al. |
| 5,190,041 A | 3/1993 | Palti |
| 5,208,147 A | 5/1993 | Kagenow et al. |
| 5,235,003 A | 8/1993 | Ward et al. |
| 5,243,983 A | 9/1993 | Tarr et al. |
| 5,249,576 A | 10/1993 | Goldberger et al. |
| 5,265,594 A | 11/1993 | Olsson et al. |
| 5,266,179 A | 11/1993 | Nankai et al. |
| 5,269,891 A | 12/1993 | Colin |
| 5,271,736 A | 12/1993 | Picha |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,287,753 A | 2/1994 | Routh et al. |
| 5,299,571 A | 4/1994 | Mastrototaro |
| 5,304,468 A | 4/1994 | Phillips et al. |
| 5,307,263 A | 4/1994 | Brown |
| 5,310,469 A | 5/1994 | Cunningham et al. |
| 5,312,361 A | 5/1994 | Zadini et al. |
| 5,314,471 A | 5/1994 | Brauker et al. |
| 5,316,008 A | 5/1994 | Suga et al. |
| 5,326,356 A | 7/1994 | Della Valle et al. |
| 5,330,521 A | 7/1994 | Cohen |
| 5,330,634 A | 7/1994 | Wong et al. |
| 5,331,555 A | 7/1994 | Hashimoto et al. |
| 5,335,658 A | 8/1994 | Bedingham |
| 5,337,747 A | 8/1994 | Neftel |
| 5,342,409 A | 8/1994 | Mullett |
| 5,343,869 A | 9/1994 | Pross et al. |
| 5,344,454 A | 9/1994 | Clarke et al. |
| 5,348,788 A | 9/1994 | White |
| 5,352,351 A | 10/1994 | White et al. |
| 5,354,449 A | 10/1994 | Band et al. |
| 5,356,786 A | 10/1994 | Heller et al. |
| 5,368,028 A | 11/1994 | Palti |
| 5,368,224 A | 11/1994 | Richardson et al. |
| 5,368,562 A | 11/1994 | Blomquist et al. |
| 5,372,135 A | 12/1994 | Mendelson et al. |

(56) References Cited

U.S. PATENT DOCUMENTS

| | | |
|---|---|---|
| 5,376,070 A | 12/1994 | Purvis et al. |
| 5,380,536 A | 1/1995 | Hubbell et al. |
| 5,380,665 A | 1/1995 | Cusack et al. |
| 5,384,028 A | 1/1995 | Ito |
| 5,390,671 A | 2/1995 | Lord et al. |
| 5,394,879 A | 3/1995 | Gorman |
| 5,397,848 A | 3/1995 | Yang et al. |
| 5,404,877 A | 4/1995 | Nolan et al. |
| 5,411,647 A | 5/1995 | Johnson et al. |
| 5,411,866 A | 5/1995 | Luong et al. |
| 5,421,328 A | 6/1995 | Bedingham |
| 5,421,923 A | 6/1995 | Clarke et al. |
| 5,429,602 A | 7/1995 | Hauser |
| 5,448,992 A | 9/1995 | Kupershmidt |
| 5,453,278 A | 9/1995 | Chan et al. |
| 5,462,051 A | 10/1995 | Oka et al. |
| 5,462,064 A | 10/1995 | D'Angelo et al. |
| 5,469,846 A | 11/1995 | Khan |
| 5,474,552 A | 12/1995 | Palti |
| 5,476,776 A | 12/1995 | Wilkins |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,507,288 A | 4/1996 | Bocker et al. |
| 5,508,203 A | 4/1996 | Fuller et al. |
| 5,513,636 A | 5/1996 | Palti |
| 5,527,288 A | 6/1996 | Gross et al. |
| 5,531,679 A | 7/1996 | Schulman et al. |
| 5,531,878 A | 7/1996 | Vadgama et al. |
| 5,545,220 A | 8/1996 | Andrews et al. |
| 5,551,850 A | 9/1996 | Williamson et al. |
| 5,553,616 A | 9/1996 | Ham et al. |
| 5,562,614 A | 10/1996 | O'Donnell |
| 5,562,615 A | 10/1996 | Nassif |
| 5,568,806 A | 10/1996 | Cheney, II et al. |
| 5,569,186 A | 10/1996 | Lord et al. |
| 5,575,293 A | 11/1996 | Miller et al. |
| 5,575,930 A | 11/1996 | Tietje-Girault et al. |
| 5,582,184 A | 12/1996 | Erickson et al. |
| 5,584,876 A | 12/1996 | Bruchman et al. |
| 5,586,553 A | 12/1996 | Halili et al. |
| 5,590,651 A | 1/1997 | Shaffer et al. |
| 5,593,440 A | 1/1997 | Brauker et al. |
| 5,611,900 A | 3/1997 | Worden et al. |
| 5,628,619 A | 5/1997 | Wilson |
| 5,640,470 A | 6/1997 | Iyer et al. |
| 5,653,756 A | 8/1997 | Clarke et al. |
| 5,658,250 A | 8/1997 | Blomquist et al. |
| 5,660,163 A | 8/1997 | Schulman et al. |
| 5,665,065 A | 9/1997 | Colman et al. |
| 5,667,504 A | 9/1997 | Baumann et al. |
| 5,676,820 A | 10/1997 | Wang et al. |
| 5,682,884 A | 11/1997 | Hill et al. |
| 5,683,562 A | 11/1997 | Schaffar et al. |
| 5,686,829 A | 11/1997 | Girault |
| 5,695,623 A | 12/1997 | Michel et al. |
| 5,743,262 A | 4/1998 | Lepper, Jr. et al. |
| 5,749,832 A | 5/1998 | Vadgama et al. |
| 5,749,907 A | 5/1998 | Mann |
| 5,768,696 A | 6/1998 | Law |
| 5,771,890 A | 6/1998 | Tamada |
| 5,782,880 A | 7/1998 | Lahtinen et al. |
| 5,782,912 A | 7/1998 | Brauker et al. |
| 5,787,900 A | 8/1998 | Butler et al. |
| 5,791,344 A | 8/1998 | Schulman et al. |
| 5,791,880 A | 8/1998 | Wilson |
| 5,795,774 A | 8/1998 | Matsumoto et al. |
| 5,798,065 A | 8/1998 | Picha |
| 5,800,383 A | 9/1998 | Chandler et al. |
| 5,800,420 A | 9/1998 | Gross et al. |
| 5,800,529 A | 9/1998 | Brauker et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,814,599 A | 9/1998 | Mitragotri et al. |
| 5,820,622 A | 10/1998 | Gross et al. |
| 5,822,715 A | 10/1998 | Worthington et al. |
| 5,836,887 A | 11/1998 | Oka et al. |
| 5,836,989 A | 11/1998 | Shelton |
| 5,840,026 A | 11/1998 | Uber, III et al. |
| 5,840,148 A | 11/1998 | Campbell et al. |
| 5,848,991 A | 12/1998 | Gross et al. |
| 5,851,197 A | 12/1998 | Marano et al. |
| 5,858,747 A | 1/1999 | Schinstine et al. |
| 5,861,019 A | 1/1999 | Sun et al. |
| 5,863,400 A | 1/1999 | Drummond et al. |
| 5,867,688 A | 2/1999 | Simmon et al. |
| 5,882,494 A | 3/1999 | Van Antwerp |
| 5,895,235 A | 4/1999 | Droz |
| 5,899,855 A | 5/1999 | Brown |
| 5,904,708 A | 5/1999 | Goedeke |
| 5,917,346 A | 6/1999 | Gord |
| 5,928,155 A | 7/1999 | Eggers et al. |
| 5,928,195 A | 7/1999 | Malamud et al. |
| 5,931,814 A | 8/1999 | Alex et al. |
| 5,933,136 A | 8/1999 | Brown |
| 5,944,661 A | 8/1999 | Swette et al. |
| 5,954,954 A | 9/1999 | Houck et al. |
| 5,957,854 A | 9/1999 | Besson et al. |
| 5,957,903 A | 9/1999 | Mirzaee et al. |
| 5,961,451 A | 10/1999 | Reber et al. |
| 5,963,132 A | 10/1999 | Yoakum |
| 5,964,993 A | 10/1999 | Blubaugh, Jr. et al. |
| 5,971,922 A | 10/1999 | Arita et al. |
| 5,985,693 A | 11/1999 | Leedy |
| 5,987,352 A | 11/1999 | Klein et al. |
| 5,995,208 A | 11/1999 | Sarge et al. |
| 5,997,501 A | 12/1999 | Gross et al. |
| 5,999,848 A | 12/1999 | Gord et al. |
| 6,001,067 A | 12/1999 | Shults et al. |
| 6,001,471 A | 12/1999 | Bries et al. |
| 6,011,984 A | 1/2000 | Van Antwerp et al. |
| 6,014,577 A | 1/2000 | Henning et al. |
| 6,016,448 A | 1/2000 | Busacker et al. |
| 6,018,674 A | 1/2000 | Aronow |
| 6,023,629 A | 2/2000 | Tamada |
| 6,024,720 A | 2/2000 | Chandler et al. |
| 6,027,445 A | 2/2000 | Von Bahr |
| 6,028,514 A | 2/2000 | Lemelson et al. |
| 6,032,059 A | 2/2000 | Henning et al. |
| 6,049,727 A | 4/2000 | Crothall |
| 6,059,946 A | 5/2000 | Yukawa et al. |
| 6,063,637 A | 5/2000 | Arnold et al. |
| 6,066,448 A | 5/2000 | Wohlstadter et al. |
| 6,071,391 A | 6/2000 | Gotoh et al. |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,103,033 A | 8/2000 | Say et al. |
| 6,115,634 A | 9/2000 | Donders et al. |
| 6,117,290 A | 9/2000 | Say et al. |
| 6,120,676 A | 9/2000 | Heller et al. |
| 6,121,009 A | 9/2000 | Heller et al. |
| 6,122,536 A | 9/2000 | Sun et al. |
| 6,123,827 A | 9/2000 | Wong et al. |
| 6,127,154 A | 10/2000 | Mosbach et al. |
| 6,134,461 A | 10/2000 | Say et al. |
| 6,142,939 A | 11/2000 | Eppstein et al. |
| 6,164,921 A | 12/2000 | Moubayed et al. |
| 6,167,614 B1 | 1/2001 | Tuttle et al. |
| 6,168,568 B1 | 1/2001 | Gavriely |
| 6,171,276 B1 | 1/2001 | Lippe et al. |
| 6,175,752 B1 | 1/2001 | Say et al. |
| 6,175,767 B1 | 1/2001 | Doyle, Sr. |

(56) References Cited

U.S. PATENT DOCUMENTS

| | | |
|---|---|---|
| 6,180,416 B1 | 1/2001 | Kurnik et al. |
| 6,187,062 B1 | 2/2001 | Oweis et al. |
| 6,189,536 B1 | 2/2001 | Martinez et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,214,185 B1 | 4/2001 | Offenbacher et al. |
| 6,230,059 B1 | 5/2001 | Duffin |
| 6,231,879 B1 | 5/2001 | Li et al. |
| 6,241,863 B1 | 6/2001 | Monbouquette |
| 6,248,067 B1 | 6/2001 | Causey, III et al. |
| 6,254,586 B1 | 7/2001 | Mann et al. |
| 6,263,222 B1 | 7/2001 | Diab et al. |
| 6,264,825 B1 | 7/2001 | Blackburn et al. |
| 6,272,364 B1 | 8/2001 | Kurnik |
| 6,274,285 B1 | 8/2001 | Gries et al. |
| 6,275,717 B1 | 8/2001 | Gross et al. |
| 6,280,408 B1 | 8/2001 | Sipin |
| 6,284,478 B1 | 9/2001 | Heller et al. |
| 6,298,254 B2 | 10/2001 | Tamada |
| 6,299,583 B1 | 10/2001 | Eggers et al. |
| 6,300,002 B1 | 10/2001 | Webb et al. |
| 6,302,855 B1 | 10/2001 | Lav et al. |
| 6,325,978 B1 | 12/2001 | Labuda et al. |
| 6,326,160 B1 | 12/2001 | Dunn et al. |
| 6,329,929 B1 | 12/2001 | Weijand et al. |
| 6,365,670 B1 | 4/2002 | Fry |
| 6,366,794 B1 | 4/2002 | Moussy et al. |
| 6,379,301 B1 | 4/2002 | Worthington et al. |
| 6,387,709 B1 | 5/2002 | Mason et al. |
| 6,403,944 B1 | 6/2002 | MacKenzie et al. |
| 6,413,393 B1 | 7/2002 | Van Antwerp et al. |
| 6,416,651 B1 | 7/2002 | Millar |
| 6,424,847 B1 | 7/2002 | Mastrototaro et al. |
| 6,427,088 B1 | 7/2002 | Bowman, IV et al. |
| 6,430,437 B1 | 8/2002 | Marro |
| 6,432,050 B1 | 8/2002 | Porat et al. |
| 6,447,448 B1 | 9/2002 | Ishikawa et al. |
| 6,447,542 B1 | 9/2002 | Weadock |
| 6,461,496 B1 | 10/2002 | Feldman et al. |
| 6,464,849 B1 | 10/2002 | Say et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,046 B1 | 11/2002 | Say et al. |
| 6,488,652 B1 | 12/2002 | Weijand et al. |
| 6,494,830 B1 | 12/2002 | Wessel |
| 6,498,043 B1 | 12/2002 | Schulman et al. |
| 6,498,941 B1 | 12/2002 | Jackson |
| 6,501,976 B1 | 12/2002 | Sohrab |
| 6,510,329 B2 | 1/2003 | Heckel |
| 6,512,939 B1 | 1/2003 | Colvin et al. |
| 6,520,997 B1 | 2/2003 | Pekkarinen et al. |
| 6,534,711 B1 | 3/2003 | Pollack |
| 6,537,318 B1 | 3/2003 | Ita et al. |
| 6,541,266 B2 | 4/2003 | Modzelewski et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,561,978 B1 | 5/2003 | Conn et al. |
| 6,565,509 B1 | 5/2003 | Say; James et al. |
| 6,569,521 B1 | 5/2003 | Sheridan et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,592,745 B1 | 7/2003 | Feldman et al. |
| 6,605,072 B2 | 8/2003 | Struys et al. |
| 6,607,509 B2 | 8/2003 | Bobroff et al. |
| 6,609,071 B2 | 8/2003 | Shapiro et al. |
| 6,612,984 B1 | 9/2003 | Kerr, II |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey, III et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,157 B1 | 12/2003 | Duchon et al. |
| 6,683,535 B1 | 1/2004 | Utke |
| 6,687,522 B2 | 2/2004 | Tamada |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,749,587 B2 | 6/2004 | Flaherty |
| 6,773,565 B2 | 8/2004 | Kunimoto et al. |
| 6,793,632 B2 | 9/2004 | Sohrab |
| 6,802,957 B2 | 10/2004 | Jung et al. |
| 6,809,653 B1 | 10/2004 | Mann et al. |
| 6,810,290 B2 | 10/2004 | Lebel et al. |
| 6,811,548 B2 | 11/2004 | Jeffrey |
| 6,813,519 B2 | 11/2004 | Lebel et al. |
| 6,862,465 B2 | 3/2005 | Shults et al. |
| 6,869,413 B2 | 3/2005 | Langley et al. |
| 6,893,396 B2 | 5/2005 | Schulze et al. |
| 6,893,552 B1 | 5/2005 | Wang et al. |
| 6,895,263 B2 | 5/2005 | Shin et al. |
| 6,895,265 B2 | 5/2005 | Silver |
| 6,925,393 B1 | 8/2005 | Kalatz et al. |
| 6,931,327 B2 | 8/2005 | Goode, Jr. et al. |
| 6,936,006 B2 | 8/2005 | Sabra |
| 6,948,492 B2 | 9/2005 | Wermeling et al. |
| 6,952,604 B2 | 10/2005 | Denuzzio et al. |
| 6,954,662 B2 | 10/2005 | Freger et al. |
| 6,960,192 B1 | 11/2005 | Flaherty et al. |
| 6,965,791 B1 | 11/2005 | Hitchcock et al. |
| 6,978,171 B2 | 12/2005 | Goetz et al. |
| 6,989,891 B2 | 1/2006 | Braig et al. |
| 6,990,366 B2 | 1/2006 | Say et al. |
| 6,998,247 B2 | 2/2006 | Monfre et al. |
| 7,011,630 B2 | 3/2006 | Desai et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,025,743 B2 | 4/2006 | Mann et al. |
| 7,027,848 B2 | 4/2006 | Robinson et al. |
| 7,033,322 B2 | 4/2006 | Silver |
| 7,060,059 B2 | 6/2006 | Keith et al. |
| 7,061,593 B2 | 6/2006 | Braig et al. |
| 7,066,884 B2 | 6/2006 | Custer et al. |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,144,496 B2 | 12/2006 | Meserol et al. |
| 7,162,290 B1 | 1/2007 | Levin |
| 7,163,511 B2 | 1/2007 | Conn et al. |
| 7,166,074 B2 | 1/2007 | Reghabi et al. |
| 7,169,289 B2 | 1/2007 | Schulein et al. |
| 7,183,102 B2 | 2/2007 | Monfre et al. |

(56) References Cited

U.S. PATENT DOCUMENTS

| | | |
|---|---|---|
| 7,184,810 B2 | 2/2007 | Caduff et al. |
| 7,192,450 B2 | 3/2007 | Brauker et al. |
| 7,221,970 B2 | 5/2007 | Parker |
| 7,226,978 B2 | 6/2007 | Tapsak et al. |
| 7,267,665 B2 | 9/2007 | Steil et al. |
| 7,276,029 B2 | 10/2007 | Goode, Jr. et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,315,767 B2 | 1/2008 | Caduff et al. |
| 7,317,927 B2 | 1/2008 | Staton et al. |
| 7,317,939 B2 | 1/2008 | Fine et al. |
| 7,338,464 B2 | 3/2008 | Blischak et al. |
| 7,343,565 B2 | 3/2008 | Ying et al. |
| 7,344,500 B2 | 3/2008 | Talbot et al. |
| 7,354,420 B2 | 4/2008 | Steil et al. |
| 7,364,562 B2 | 4/2008 | Braig et al. |
| 7,367,942 B2 | 5/2008 | Grage et al. |
| 7,399,277 B2 | 7/2008 | Saidara et al. |
| 7,426,408 B2 | 9/2008 | Denuzzio et al. |
| 7,433,727 B2 | 10/2008 | Ward et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,530,930 B2 | 5/2009 | Liao et al. |
| 7,604,593 B2 | 10/2009 | Parris et al. |
| 7,618,369 B2 | 11/2009 | Hayter et al. |
| 7,647,237 B2 | 1/2010 | Malave et al. |
| 7,695,434 B2 | 4/2010 | Malecha |
| 7,731,659 B2 | 6/2010 | Malecha |
| 7,761,126 B2 | 7/2010 | Gardner et al. |
| 7,766,830 B2 | 8/2010 | Fox et al. |
| 7,927,274 B2 | 4/2011 | Rasdal et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,229,535 B2 | 7/2012 | Mensinger et al. |
| 8,591,455 B2 | 11/2013 | Mensinger et al. |
| 9,020,572 B2 | 4/2015 | Mensinger et al. |
| 9,143,569 B2 | 9/2015 | Mensinger et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0009810 A1 | 1/2002 | O'Connor et al. |
| 2002/0016535 A1 | 2/2002 | Martin et al. |
| 2002/0019022 A1 | 2/2002 | Dunn et al. |
| 2002/0019330 A1 | 2/2002 | Murray et al. |
| 2002/0022883 A1 | 2/2002 | Burg |
| 2002/0026110 A1 | 2/2002 | Parris et al. |
| 2002/0026111 A1 | 2/2002 | Ackerman |
| 2002/0042561 A1 | 4/2002 | Schulman et al. |
| 2002/0045808 A1 | 4/2002 | Ford et al. |
| 2002/0065453 A1 | 5/2002 | Lesho et al. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0119711 A1 | 8/2002 | VanAntwerp et al. |
| 2002/0123048 A1 | 9/2002 | Gau |
| 2002/0128546 A1 | 9/2002 | Silver |
| 2002/0151796 A1 | 10/2002 | Koulik |
| 2002/0161288 A1 | 10/2002 | Shin et al. |
| 2002/0182241 A1 | 12/2002 | Borenstein et al. |
| 2002/0188185 A1 | 12/2002 | Sohrab |
| 2002/0193885 A1 | 12/2002 | Legeay et al. |
| 2002/0198513 A1 | 12/2002 | Lebel et al. |
| 2003/0004432 A1 | 1/2003 | Assenheimer |
| 2003/0023171 A1 | 1/2003 | Sato et al. |
| 2003/0028089 A1 | 2/2003 | Galley et al. |
| 2003/0032874 A1 | 2/2003 | Rhodes et al. |
| 2003/0036773 A1 | 2/2003 | Whitehurst et al. |
| 2003/0050546 A1 | 3/2003 | Desai et al. |
| 2003/0054428 A1 | 3/2003 | Monfre et al. |
| 2003/0060765 A1 | 3/2003 | Campbell et al. |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0091433 A1 | 5/2003 | Tam et al. |
| 2003/0100040 A1 | 5/2003 | Bonnecaze et al. |
| 2003/0100821 A1 | 5/2003 | Heller et al. |
| 2003/0117296 A1 | 6/2003 | Seely |
| 2003/0119208 A1 | 6/2003 | Yoon et al. |
| 2003/0120152 A1 | 6/2003 | Omiya |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0176183 A1 | 9/2003 | Drucker et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0225324 A1 | 12/2003 | Anderson et al. |
| 2003/0228681 A1 | 12/2003 | Ritts et al. |
| 2003/0231550 A1 | 12/2003 | MacFarlane |
| 2003/0235817 A1 | 12/2003 | Bartkowiak et al. |
| 2004/0006263 A1 | 1/2004 | Anderson et al. |
| 2004/0010207 A1 | 1/2004 | Flaherty et al. |
| 2004/0015063 A1 | 1/2004 | Denuzzio et al. |
| 2004/0015134 A1 | 1/2004 | Lavi et al. |
| 2004/0023317 A1 | 2/2004 | Motamedi et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0040840 A1 | 3/2004 | Mao et al. |
| 2004/0052689 A1 | 3/2004 | Yao |
| 2004/0054352 A1 | 3/2004 | Adams et al. |
| 2004/0068230 A1 | 4/2004 | Estes et al. |
| 2004/0074785 A1 | 4/2004 | Holker et al. |
| 2004/0078219 A1 | 4/2004 | Kaylor et al. |
| 2004/0122353 A1 | 6/2004 | Shahmirian et al. |
| 2004/0143173 A1 | 7/2004 | Reghabi et al. |
| 2004/0146909 A1 | 7/2004 | Duong et al. |
| 2004/0152187 A1 | 8/2004 | Haight et al. |
| 2004/0152622 A1 | 8/2004 | Keith et al. |
| 2004/0153289 A1 | 8/2004 | Casey et al. |
| 2004/0158138 A1 | 8/2004 | Kilcoyne et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0204687 A1 | 10/2004 | Mogensen et al. |
| 2004/0219664 A1 | 11/2004 | Heller et al. |
| 2004/0220517 A1 | 11/2004 | Starkweather et al. |
| 2004/0253365 A1 | 12/2004 | Warren et al. |
| 2004/0254433 A1 | 12/2004 | Bandis et al. |
| 2005/0003399 A1 | 1/2005 | Blackburn et al. |
| 2005/0010087 A1 | 1/2005 | Banet et al. |
| 2005/0027180 A1 | 2/2005 | Goode, Jr. et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0051427 A1 | 3/2005 | Brauker et al. |
| 2005/0054909 A1 | 3/2005 | Petisce et al. |
| 2005/0056552 A1 | 3/2005 | Simpson et al. |
| 2005/0065464 A1 | 3/2005 | Talbot et al. |
| 2005/0090607 A1 | 4/2005 | Tapsak et al. |
| 2005/0096519 A1 | 5/2005 | Denuzzio et al. |
| 2005/0103625 A1 | 5/2005 | Rhodes et al. |
| 2005/0107677 A1 | 5/2005 | Ward et al. |
| 2005/0112358 A1 | 5/2005 | Potyrailo et al. |
| 2005/0113653 A1 | 5/2005 | Fox et al. |
| 2005/0121322 A1 | 6/2005 | Say et al. |

(56) References Cited

U.S. PATENT DOCUMENTS

| | | |
|---|---|---|
| 2005/0124873 A1 | 6/2005 | Shults et al. |
| 2005/0137480 A1* | 6/2005 | Alt .................. A61B 5/0031 600/508 |
| 2005/0139489 A1 | 6/2005 | Davies et al. |
| 2005/0143635 A1 | 6/2005 | Kamath et al. |
| 2005/0143671 A1 | 6/2005 | Hastings et al. |
| 2005/0143675 A1 | 6/2005 | Neel et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0187720 A1 | 8/2005 | Goode, Jr. et al. |
| 2005/0192557 A1 | 9/2005 | Brauker et al. |
| 2005/0196747 A1 | 9/2005 | Stiene |
| 2005/0197585 A1 | 9/2005 | Brockway et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |
| 2005/0261563 A1 | 11/2005 | Zhou et al. |
| 2006/0001550 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020215 A1* | 1/2006 | Callahan, III ......... A61B 8/468 600/481 |
| 2006/0025663 A1 | 2/2006 | Talbot et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0040402 A1 | 2/2006 | Brauker et al. |
| 2006/0051736 A1 | 3/2006 | Shields et al. |
| 2006/0052745 A1 | 3/2006 | Van Antwerp et al. |
| 2006/0068208 A1 | 3/2006 | Tapsak et al. |
| 2006/0079740 A1 | 4/2006 | Silver et al. |
| 2006/0079809 A1 | 4/2006 | Goldberger et al. |
| 2006/0086624 A1 | 4/2006 | Tapsak et al. |
| 2006/0089856 A1 | 4/2006 | Kadhiresan et al. |
| 2006/0094946 A1 | 5/2006 | Kellogg et al. |
| 2006/0100588 A1 | 5/2006 | Brunnberg et al. |
| 2006/0142651 A1 | 6/2006 | Brister et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0222566 A1 | 10/2006 | Brauker et al. |
| 2006/0224141 A1 | 10/2006 | Rush et al. |
| 2006/0226991 A1* | 10/2006 | Rivas ................ G06F 19/00 340/573.1 |
| 2006/0229512 A1 | 10/2006 | Petisce et al. |
| 2006/0258929 A1 | 11/2006 | Goode, Jr. et al. |
| 2006/0263839 A1 | 11/2006 | Ward et al. |
| 2006/0281982 A1 | 12/2006 | Grata et al. |
| 2006/0281985 A1 | 12/2006 | Ward et al. |
| 2006/0293576 A1 | 12/2006 | Van Antwerp et al. |
| 2007/0016381 A1 | 1/2007 | Kamath et al. |
| 2007/0027370 A1 | 2/2007 | Brauker et al. |
| 2007/0027384 A1 | 2/2007 | Brister et al. |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0043596 A1* | 2/2007 | Donaldson ............ G16H 10/60 705/3 |
| 2007/0049873 A1 | 3/2007 | Hansen et al. |
| 2007/0059196 A1 | 3/2007 | Brister et al. |
| 2007/0060870 A1 | 3/2007 | Tolle et al. |
| 2007/0066873 A1 | 3/2007 | Kamath et al. |
| 2007/0085995 A1 | 4/2007 | Pesach et al. |
| 2007/0093704 A1 | 4/2007 | Brister et al. |
| 2007/0100222 A1 | 5/2007 | Mastrototaro et al. |
| 2007/0116600 A1 | 5/2007 | Kochar et al. |
| 2007/0129621 A1 | 6/2007 | Kellogg et al. |
| 2007/0130153 A1* | 6/2007 | Nachman ............ G06F 16/9537 |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0179436 A1 | 8/2007 | Braig et al. |
| 2007/0197889 A1 | 8/2007 | Brister et al. |
| 2007/0197890 A1 | 8/2007 | Boock et al. |
| 2007/0200254 A1 | 8/2007 | Curry |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0232879 A1 | 10/2007 | Brister et al. |
| 2007/0235331 A1 | 10/2007 | Simpson et al. |
| 2007/0249916 A1 | 10/2007 | Pesach et al. |
| 2007/0251835 A1* | 11/2007 | Mehta ................... G16H 40/67 205/783 |
| 2007/0255116 A1 | 11/2007 | Mehta et al. |
| 2007/0255126 A1 | 11/2007 | Moberg et al. |
| 2007/0288266 A1* | 12/2007 | Sysko ................... G06Q 50/22 705/2 |
| 2008/0021666 A1 | 1/2008 | Goode, Jr. et al. |
| 2008/0027301 A1 | 1/2008 | Ward et al. |
| 2008/0029390 A1 | 2/2008 | Roche et al. |
| 2008/0033254 A1 | 2/2008 | Kamath et al. |
| 2008/0071157 A1 | 3/2008 | McGarraugh et al. |
| 2008/0071158 A1 | 3/2008 | McGarraugh et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086043 A1 | 4/2008 | Heller et al. |
| 2008/0091094 A1 | 4/2008 | Heller et al. |
| 2008/0091095 A1 | 4/2008 | Heller et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0139910 A1 | 6/2008 | Mastrototaro et al. |
| 2008/0154101 A1 | 6/2008 | Jain et al. |
| 2008/0171941 A1 | 7/2008 | Huelskamp et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0193936 A1 | 8/2008 | Squirrell |
| 2008/0194837 A1 | 8/2008 | Kim et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0208025 A1 | 8/2008 | Shults et al. |
| 2008/0214915 A1 | 9/2008 | Brister et al. |
| 2008/0242961 A1 | 10/2008 | Brister et al. |
| 2008/0262334 A1 | 10/2008 | Dunn et al. |
| 2008/0262469 A1 | 10/2008 | Brister et al. |
| 2008/0287764 A1 | 11/2008 | Rasdal et al. |

(56) References Cited

U.S. PATENT DOCUMENTS

| | | |
|---|---|---|
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306433 A1 | 12/2008 | Cesaroni |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005666 A1 | 1/2009 | Shin et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0062633 A1 | 3/2009 | Brauker et al. |
| 2009/0062635 A1 | 3/2009 | Brauker et al. |
| 2009/0062645 A1 | 3/2009 | Fehre et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0177068 A1 | 7/2009 | Stivoric et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0241093 A1 | 9/2009 | Chiu et al. |
| 2009/0264856 A1 | 10/2009 | Lebel et al. |
| 2010/0174158 A1 | 7/2010 | Kamath et al. |
| 2010/0179401 A1 | 7/2010 | Rasdal et al. |
| 2010/0179404 A1 | 7/2010 | Kamath et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0234707 A1 | 9/2010 | Goode, Jr. et al. |
| 2010/0235106 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0118579 A1 | 5/2011 | Goode, Jr. et al. |
| 2011/0124997 A1 | 5/2011 | Goode, Jr. et al. |
| 2011/0130970 A1 | 6/2011 | Goode, Jr. et al. |
| 2011/0137601 A1 | 6/2011 | Goode, Jr. et al. |
| 2011/0201910 A1 | 8/2011 | Rasdal et al. |
| 2011/0218414 A1 | 9/2011 | Kamath et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0270158 A1 | 11/2011 | Brauker et al. |
| 2014/0040984 A1 | 2/2014 | Mackler |
| 2017/0366617 A1 | 12/2017 | Mensinger et al. |

FOREIGN PATENT DOCUMENTS

| | | |
|---|---|---|
| EP | 0107634 A2 | 5/1984 |
| EP | 0127958 A2 | 12/1984 |
| EP | 0286118 A2 | 10/1988 |
| EP | 0288793 A2 | 11/1988 |
| EP | 0320109 A1 | 6/1989 |
| EP | 0352610 A2 | 1/1990 |
| EP | 0352631 A2 | 1/1990 |
| EP | 0353328 A1 | 2/1990 |
| EP | 0390390 A1 | 10/1990 |
| EP | 0396788 A1 | 11/1990 |
| EP | 0406473 A1 | 1/1991 |
| EP | 0440044 A1 | 8/1991 |
| EP | 0441252 A2 | 8/1991 |
| EP | 0441394 A2 | 8/1991 |
| EP | 0467078 A2 | 1/1992 |
| EP | 0155813 B1 | 7/1992 |
| EP | 0323605 B1 | 1/1994 |
| EP | 0595474 A3 | 7/1994 |
| EP | 0647849 A2 | 4/1995 |
| EP | 0424633 B1 | 1/1996 |
| EP | 0776628 A2 | 6/1997 |
| EP | 0880936 A2 | 12/1998 |
| EP | 0587008 B1 | 2/1999 |
| EP | 0967788 A2 | 12/1999 |
| EP | 0995805 A1 | 4/2000 |
| EP | 1102194 A2 | 5/2001 |
| EP | 1112717 A1 | 7/2001 |
| EP | 1112718 A1 | 7/2001 |
| EP | 1120084 A1 | 8/2001 |
| EP | 1120085 A1 | 8/2001 |
| EP | 1153571 A1 | 11/2001 |
| EP | 1205753 A2 | 5/2002 |
| EP | 1251137 A2 | 10/2002 |
| EP | 1258728 A2 | 11/2002 |
| EP | 1266607 A2 | 12/2002 |
| EP | 0680727 B1 | 6/2003 |
| EP | 0774658 B1 | 10/2003 |
| EP | 1413245 A2 | 4/2004 |
| EP | 1437086 A1 | 7/2004 |
| EP | 1672070 A2 | 6/2006 |
| EP | 1411346 B1 | 10/2006 |
| EP | 1722310 A1 | 11/2006 |
| EP | 1759726 A2 | 3/2007 |
| EP | 1234053 B1 | 4/2007 |
| EP | 1850226 A1 | 10/2007 |
| EP | 1862112 A1 | 12/2007 |
| EP | 1870026 A1 | 12/2007 |
| EP | 1905514 A1 | 4/2008 |
| EP | 1522255 B1 | 5/2008 |
| EP | 1918837 A1 | 5/2008 |
| EP | 1933246 A1 | 6/2008 |
| EP | 1949849 A1 | 7/2008 |
| EP | 1972270 A1 | 9/2008 |
| EP | 1982644 A1 | 10/2008 |
| EP | 1281351 B1 | 11/2008 |
| EP | 1457913 B1 | 12/2008 |
| EP | 2223710 A1 | 9/2010 |
| EP | 2226086 A1 | 9/2010 |
| FR | 2656423 A1 | 6/1991 |
| FR | 2760962 A1 | 9/1998 |
| GB | 2149918 A | 6/1985 |
| JP | S6283649 A | 4/1987 |
| JP | S6283849 A | 4/1987 |
| JP | 2000060826 A | 2/2000 |
| JP | 2002189015 A | 7/2002 |
| JP | 2003108679 A | 4/2003 |
| WO | WO-8902720 A1 | 4/1989 |
| WO | WO-8905977 A1 | 6/1989 |
| WO | WO-8907263 A1 | 8/1989 |
| WO | WO-9002938 A1 | 3/1990 |
| WO | WO-9010861 A1 | 9/1990 |
| WO | WO-9213271 A1 | 8/1992 |
| WO | WO-9314693 A1 | 8/1993 |
| WO | WO-9422367 A1 | 10/1994 |
| WO | WO-9507109 A1 | 3/1995 |
| WO | WO-9511454 A1 | 4/1995 |
| WO | WO-9513838 A1 | 5/1995 |
| WO | WO-9614026 A1 | 5/1996 |
| WO | WO-9625089 A1 | 8/1996 |
| WO | WO-9635697 A1 | 11/1996 |
| WO | WO-9637246 A1 | 11/1996 |
| WO | WO-9701986 A1 | 1/1997 |
| WO | WO-9706727 A1 | 2/1997 |
| WO | WO-9715227 A1 | 5/1997 |
| WO | WO-9722291 A1 | 6/1997 |
| WO | WO-9728737 A1 | 8/1997 |
| WO | WO-9734521 A1 | 9/1997 |
| WO | WO-9738625 A1 | 10/1997 |
| WO | WO-9824358 A2 | 6/1998 |
| WO | WO-9824366 A2 | 6/1998 |

(56) References Cited

FOREIGN PATENT DOCUMENTS

| | | |
|---|---|---|
| WO | WO-9838904 A1 | 9/1998 |
| WO | WO-9838906 A1 | 9/1998 |
| WO | WO-9845427 A2 | 10/1998 |
| WO | WO-9904043 A1 | 1/1999 |
| WO | WO-9913574 A1 | 3/1999 |
| WO | WO-9927100 A1 | 6/1999 |
| WO | WO-9927848 A1 | 6/1999 |
| WO | WO-9948419 A1 | 9/1999 |
| WO | WO-9949039 A2 | 9/1999 |
| WO | WO-9956613 A1 | 11/1999 |
| WO | WO-9959657 A1 | 11/1999 |
| WO | WO-9963328 A1 | 12/1999 |
| WO | WO-9964620 A2 | 12/1999 |
| WO | WO-0007013 A2 | 2/2000 |
| WO | WO-0012720 A2 | 3/2000 |
| WO | WO-0013002 A2 | 3/2000 |
| WO | WO-0013003 A1 | 3/2000 |
| WO | WO-0018449 A2 | 4/2000 |
| WO | WO-0019887 A1 | 4/2000 |
| WO | WO-0020626 A1 | 4/2000 |
| WO | WO-0032098 A1 | 6/2000 |
| WO | WO-0033065 A1 | 6/2000 |
| WO | WO-0040144 A1 | 7/2000 |
| WO | WO-0049941 A1 | 8/2000 |
| WO | WO-0049942 A2 | 8/2000 |
| WO | WO-0059373 A1 | 10/2000 |
| WO | WO-0072181 A2 | 11/2000 |
| WO | WO-0074753 A1 | 12/2000 |
| WO | WO-0116579 A1 | 3/2001 |
| WO | WO-0136666 A1 | 5/2001 |
| WO | WO-0140466 A2 | 6/2001 |
| WO | WO-0152727 A1 | 7/2001 |
| WO | WO-0152935 A1 | 7/2001 |
| WO | WO-0154753 A2 | 8/2001 |
| WO | WO-0159425 A1 | 8/2001 |
| WO | WO-0174968 A2 | 10/2001 |
| WO | WO-0188534 A2 | 11/2001 |
| WO | WO-0191634 A2 | 12/2001 |
| WO | WO-0205702 A2 | 1/2002 |
| WO | WO-0207596 A1 | 1/2002 |
| WO | WO-2000078210 A2 | 5/2002 |
| WO | WO-02056751 A2 | 7/2002 |
| WO | WO-02058537 A2 | 8/2002 |
| WO | WO-02062210 A1 | 8/2002 |
| WO | WO-02074161 A2 | 9/2002 |
| WO | WO-02078512 A2 | 10/2002 |
| WO | WO-02082989 A1 | 10/2002 |
| WO | WO-02087681 A2 | 11/2002 |
| WO | WO-02089666 A2 | 11/2002 |
| WO | WO-02100262 A1 | 12/2002 |
| WO | WO-02100266 A1 | 12/2002 |
| WO | WO-02100474 A2 | 12/2002 |
| WO | WO-03000127 A2 | 1/2003 |
| WO | WO-03008013 A2 | 1/2003 |
| WO | WO-03008014 A2 | 1/2003 |
| WO | WO-03009207 A1 | 1/2003 |
| WO | WO-03009208 A1 | 1/2003 |
| WO | WO-03022327 A2 | 3/2003 |
| WO | WO-03053498 A2 | 7/2003 |
| WO | WO-03057027 A2 | 7/2003 |
| WO | WO-03063700 A1 | 8/2003 |
| WO | WO-03074107 A2 | 9/2003 |
| WO | WO-03094714 A1 | 11/2003 |
| WO | WO-03101862 A1 | 12/2003 |
| WO | WO-03106966 A2 | 12/2003 |
| WO | WO-2004008956 A2 | 1/2004 |
| WO | WO-2004009161 A1 | 1/2004 |
| WO | WO-2004028337 A2 | 4/2004 |
| WO | WO-2004042364 A2 | 5/2004 |
| WO | WO-2004060455 A1 | 7/2004 |
| WO | WO-2004061420 A2 | 7/2004 |
| WO | WO-2004110256 A2 | 12/2004 |
| WO | WO-2004113912 A1 | 12/2004 |
| WO | WO-2005001462 A1 | 1/2005 |
| WO | WO-2005011489 A1 | 2/2005 |
| WO | WO-2005020797 A2 | 3/2005 |
| WO | WO-2005026689 A2 | 3/2005 |
| WO | WO-2005032400 A2 | 4/2005 |
| WO | WO-2005041766 A1 | 5/2005 |
| WO | WO-2005048834 A1 | 6/2005 |
| WO | WO-2005058028 A2 | 6/2005 |
| WO | WO-2005065537 A1 | 7/2005 |
| WO | WO-2005065538 A2 | 7/2005 |
| WO | WO-2005078424 A1 | 8/2005 |
| WO | WO-2005084546 A2 | 9/2005 |
| WO | WO-2005089103 A2 | 9/2005 |
| WO | WO-2005026689 A9 | 10/2005 |
| WO | WO-2005101994 A2 | 11/2005 |
| WO | WO-2005112619 A2 | 12/2005 |
| WO | WO-2005121785 A2 | 12/2005 |
| WO | WO-2005124331 A1 | 12/2005 |
| WO | WO-2006001929 A1 | 1/2006 |
| WO | WO-2006019623 A2 | 2/2006 |
| WO | WO-2006020212 A2 | 2/2006 |
| WO | WO-2006026222 A2 | 3/2006 |
| WO | WO-2006029293 A1 | 3/2006 |
| WO | WO-2006023241 A9 | 5/2006 |
| WO | WO-2006049854 A2 | 5/2006 |
| WO | WO-2006050405 A1 | 5/2006 |
| WO | WO-2006060806 A2 | 6/2006 |
| WO | WO-2006076412 A1 | 7/2006 |
| WO | WO-2006079114 A2 | 7/2006 |
| WO | WO-2006083831 A1 | 8/2006 |
| WO | WO-2006083885 A1 | 8/2006 |
| WO | WO-2006098887 A2 | 9/2006 |
| WO | WO-2006102412 A2 | 9/2006 |
| WO | WO-2006104843 A1 | 10/2006 |
| WO | WO-2006105146 A2 | 10/2006 |
| WO | WO-2006108811 A1 | 10/2006 |
| WO | WO-2006108858 A1 | 10/2006 |
| WO | WO-2006118713 A1 | 11/2006 |
| WO | WO-2006124759 A2 | 11/2006 |
| WO | WO-2006130268 A1 | 12/2006 |
| WO | WO-2006131288 A1 | 12/2006 |
| WO | WO-2006132899 A2 | 12/2006 |
| WO | WO-2006133851 A2 | 12/2006 |
| WO | WO-2007002579 A2 | 1/2007 |
| WO | WO-2007005170 A2 | 1/2007 |
| WO | WO-2007005219 A1 | 1/2007 |
| WO | WO-2007021423 A2 | 2/2007 |
| WO | WO-2007021892 A1 | 2/2007 |
| WO | WO-2007021894 A2 | 2/2007 |
| WO | WO-2007025088 A2 | 3/2007 |
| WO | WO-2007028138 A2 | 3/2007 |
| WO | WO-2007028271 A2 | 3/2007 |
| WO | WO-2007033010 A1 | 3/2007 |
| WO | WO-2007037970 A1 | 4/2007 |
| WO | WO-2007037989 A2 | 4/2007 |
| WO | WO-2007038464 A1 | 4/2007 |
| WO | WO-2007053497 A2 | 5/2007 |
| WO | WO-2007053832 A2 | 5/2007 |
| WO | WO-2007056638 A2 | 5/2007 |
| WO | WO-2007058921 A2 | 5/2007 |
| WO | WO-2007059061 A1 | 5/2007 |
| WO | WO-2007061992 A2 | 5/2007 |
| WO | WO-2007062013 A2 | 5/2007 |
| WO | WO-2007065285 A2 | 6/2007 |
| WO | WO-2007076940 A1 | 7/2007 |
| WO | WO-2007079025 A2 | 7/2007 |
| WO | WO-2007081608 A2 | 7/2007 |
| WO | WO-2007097754 A1 | 8/2007 |
| WO | WO-2007101260 A2 | 9/2007 |
| WO | WO-2007114943 A2 | 10/2007 |
| WO | WO-2007114979 A2 | 10/2007 |
| WO | WO-2007120363 A2 | 10/2007 |
| WO | WO-2007126444 A2 | 11/2007 |
| WO | WO-2007126920 A1 | 11/2007 |
| WO | WO-2007127606 A1 | 11/2007 |
| WO | WO-2007127879 A2 | 11/2007 |
| WO | WO-2007127880 A2 | 11/2007 |
| WO | WO-2007130239 A1 | 11/2007 |
| WO | WO-2007137286 A2 | 11/2007 |
| WO | WO-2007143225 A2 | 12/2007 |
| WO | WO-2008003003 A2 | 1/2008 |

(56) References Cited

FOREIGN PATENT DOCUMENTS

| WO | WO-2008005780 A2 | 1/2008 |
|---|---|---|
| WO | WO-2008016486 A2 | 2/2008 |
| WO | WO-2008016501 A2 | 2/2008 |
| WO | WO-2008021913 A2 | 2/2008 |
| WO | WO-2008028644 A1 | 3/2008 |
| WO | WO-2008036437 A2 | 3/2008 |
| WO | WO-2008037485 A1 | 4/2008 |
| WO | WO-2008039944 A2 | 4/2008 |
| WO | WO-2008039946 A2 | 4/2008 |
| WO | WO-2008039949 A2 | 4/2008 |
| WO | WO-2008042760 A2 | 4/2008 |
| WO | WO-2008048452 A2 | 4/2008 |
| WO | WO-2007143225 A9 | 5/2008 |
| WO | WO-2008051924 A2 | 5/2008 |
| WO | WO-2008052057 A2 | 5/2008 |
| WO | WO-2008052199 A2 | 5/2008 |
| WO | WO-2008052374 A1 | 5/2008 |
| WO | WO-2008054608 A1 | 5/2008 |
| WO | WO-2008054676 A2 | 5/2008 |
| WO | WO-2008054677 A2 | 5/2008 |
| WO | WO-2008055037 A2 | 5/2008 |
| WO | WO-2008060827 A1 | 5/2008 |
| WO | WO-2008067291 A2 | 6/2008 |
| WO | WO-2008067314 A2 | 6/2008 |
| WO | WO-2008069931 A1 | 6/2008 |
| WO | WO-2008069932 A1 | 6/2008 |
| WO | WO-2008073813 A1 | 6/2008 |
| WO | WO-2008076868 A2 | 6/2008 |
| WO | WO-2008079616 A1 | 7/2008 |
| WO | WO-2008079849 A2 | 7/2008 |
| WO | WO-2008080591 A1 | 7/2008 |
| WO | WO-2008083179 A2 | 7/2008 |
| WO | WO-2008083379 A1 | 7/2008 |
| WO | WO-2008064053 A9 | 8/2008 |
| WO | WO-2008092286 A1 | 8/2008 |
| WO | WO-2008101211 A2 | 8/2008 |
| WO | WO-2008101217 A2 | 8/2008 |
| WO | WO-2008101229 A2 | 8/2008 |
| WO | WO-2008103620 A2 | 8/2008 |
| WO | WO-2008104397 A2 | 9/2008 |
| WO | WO-2008112375 A2 | 9/2008 |
| WO | WO-2007079015 A9 | 10/2008 |
| WO | WO-2008116329 A1 | 10/2008 |
| WO | WO-2008118257 A1 | 10/2008 |
| WO | WO-2008124597 A1 | 10/2008 |
| WO | WO-2008128210 A1 | 10/2008 |
| WO | WO-2008130895 A2 | 10/2008 |
| WO | WO-2008130896 A1 | 10/2008 |
| WO | WO-2008130897 A2 | 10/2008 |
| WO | WO-2008130898 A1 | 10/2008 |
| WO | WO-2008134146 A1 | 11/2008 |
| WO | WO-2008134561 A1 | 11/2008 |
| WO | WO-2008134587 A1 | 11/2008 |
| WO | WO-2008135128 A1 | 11/2008 |
| WO | WO-2008137405 A1 | 11/2008 |
| WO | WO-2008138006 A2 | 11/2008 |
| WO | WO-2008150280 A1 | 12/2008 |
| WO | WO-2008150436 A1 | 12/2008 |
| WO | WO-2008150633 A2 | 12/2008 |

OTHER PUBLICATIONS

Aalders, et al., "Development of a Wearable Glucose Sensor; Studies in Healthy Volunteers and in Diabetic Patients," The International Journal of Artificial Organs, 1991, vol. 14, No. 2, pp. 102-108.

Abe, et al., "Characterization of Glucose Microsensors for Intracellular Measurements," Analytical Chemistry, 1992, vol. 64, No. 18, pp. 2160-2163.

Abel, et al., "Biosensors for in Vivo Glucose Measurements: Can We Cross the Experimental Stage," Biosensors & Bioelectronics, 2002, vol. 17, pp. 1059-1070.

Abel, et al., "Experience With an Implantable Glucose Sensor as a Prerequisite of an Artificial Beta Cell," Biomed. Biochim. Actan, 1984, vol. 43, No. 5, pp. 577-584.

Alcock S.J., et al., "Continuous Analyte Monitoring to Aid Clinical Practice," IEEE Engineering in Medicine & Biology, 1994, vol. 13, pp. 319-325.

Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.

Armour J.C., et al., "Application of Chronic Intravascular Blood Glucose Sensor in Dogs," Diabetes, Dec. 1990, vol. 39, pp. 1519-1526.

Assolant-Vinet C.H., et al., "New Immoblized Enzyme Membranes for Tailor-Made Biosensors", Analytical Letters, 1986, vol. 19(7 &8), pp. 875-885.

Atanasov P., et al., "Biosensor for Continuous Glucose Monitoring," Biotechnology and Bioengineering, John Wiley & sons Inc, 1994, vol. 43, pp. 262-266.

Atanasov P., et al., "Implantation of a Refillable Glucose Monitoring-Telemetry Device," Biosenors and Bioelectronics, vol. 12 (7), 1997, pp. 669-680.

Aussedat B., et al., "A User-Friendly Method for Calibrating a Subcutaneous Glucose Sensor-Based Hypoglycaemic Alarm," Elsevier Science Limited, Biosensors & Bioelectronic, 1997, vol. 12, No. 11, pp. 1061-1071.

Bailey T.S., et al., "Reduction in Hemoglobin A1C with Real-Time Continuous Glucose Monitoring: Results from a 12-Week Observational Study," Diabetes Technology & Therapeutics, vol. 9 (3), 2007, pp. 203-210.

Bard A.J., et al., "Electrochemical Methods," Fundamentals and Applications, John Wiley & Sons, New York, 1980, pp. 173-175.

Bardeletti G., et al., "A Reliable L-Lactate Electrode with a New Membrane for Enzyme Immobilization for Amperometric Assay of Lactate," Analytica Chemica Acta, vol. 187, 1986, pp. 47-54.

Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.

Bellucci F., et al., "Electrochemical Behaviour of Graphite-Epoxy Composite Materials (GECM) in Aqueous Salt Solutions," Journal of Applied Electrochemistry, vol. 16 (1), Jan. 1986, pp. 15-22.

Bertrand C., et al., "Multipurpose Electrode with Different Enzyme Systems Bound to Collagen Films," Analytica Chemica Acta, 1981, vol. 126, pp. 23-34.

Bessman S.P., et al., "Progress toward a Glucose Sensor for the Artificial Pancreas," Proceedings of a Workshop on Ion-Selective Microelectrodes, Jun. 4-5, 1973, Boston University, 1973, pp. 189-197.

Biermann E., et al., "How Would Patients Behave if they were Continually Informed of their Blood Glucose Levels? A Simulation Study Using a "Virtual" Patient," Diabetes Technology & Therapeutics, vol. 10 (3), 2008, pp. 178-187.

Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.

Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.

Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.

Bland J.M., et al., "Statistical Methods for Assessing Agreement Between Two Methods of Clinical Measurement," The Lancet, Feb. 8, 1986, pp. 307-310.

Bobbioni-Harsch E., et al., "Lifespan of Subcutaneous Glucose Sensors and their Performances during Dynamic Glycaemia Changes in Rats," J. Biomed. Eng., vol. 15, 1993, pp. 457-463.

Bode B.W., "Clinical Utility of the Continuous Glucose Monitoring System," Diabetes Technology & Therapeutics, vol. 2, Supplement 1, 2000, pp. S35-S41.

(56) References Cited

OTHER PUBLICATIONS

Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.

Bode B.W., et al., "Using the Continuous Glucose Monitoring System to Improve the Management of Type 1 Diabetes," Diabetes Technology & Therapeutics, vol. 2, Supplement 1, 2000, pp. S43-S48.

Boedeker Plastics Inc, "Polyethylene Specifications," Polyethylene Data Sheet, Retrieved from http://www.boedeker.com/polye.sub.--p. htm on Aug. 19, 2009, 4 pages.

Boland E., et al., "Limitations of Conventional Methods of Self-Monitoring of Blood Glucose," Diabetes Care, vol. 24 (11), Nov. 2001, pp. 1858-1862.

Bowman L., et al., "The Packaging of Implantable Integrated Sensors," IEEE Transactions in Biomedical Engineering, vol. BME-33 (2), Feb. 1986, pp. 248-255.

Brauker J., et al., "Local Inflammatory Response Around Diffusion Chambers Containing Xenografts," Transplantation, vol. 61 (12), Jun. 27, 1996, pp. 1671-1677.

Braunwald E., "Biomarkers in Heart Failure," Medical Progress, The New England Journal of Medicine, vol. 358, May 15, 2008, pp. 2148-2159.

Bremer T.M., et al., "Benchmark Data from the Literature for Evaluation of New Glucose Sensing Technologies," Diabetes Technology & Therapeutics, vol. 3 (3), 2001, pp. 409-418.

Brooks S.L., et al., "Development of an On-line Glucose Sensor for Fermentation Monitoring," Biosensors, vol. 3, 1987/1988, pp. 45-56.

Bruckel J., et al., "In Vivo Measurement of Subcutaneous Glucose Concentrations with an Enzymatic Glucose Sensor and a Wick Method," Klin Wochenschr, vol. 67, 1989, pp. 491-495.

Cai Q., et al., "A Wireless, Remote Query Glucose Biosensor Based on a pH-Sensitive Polymer," Analytical Chemistry, vol. 76 (14), Jul. 15, 2004, pp. 4038-4043.

Campanella L., et al., "Biosensor for Direct Determination of Glucose and Lactate in Undiluted Biological Fluids," Biosensors & Bioelectronics, vol. 8, 1993, pp. 307-314.

Candas B., et al., "An Adaptive Plasma Glucose Controller Based on a Nonlinear Insulin/Glucose Model," IEEE Transactions on Biomedical Engineering, vol. 41 (2), Feb. 1994, pp. 116-124.

Cass A.E.G., et al., "Ferrocene-Mediated Enzyme Electrodes for Amperometric Determination of Glucose," Analytical Chemistry, vol. 56 (4), Apr. 1984, pp. 667-671.

Cassidy J.F., et al., "Novel Electrochemical Device for the Detection of Cholesterol or Glucose," Analyst, vol. 118, Apr. 1993, pp. 415-418.

Chase H.P., et al., "Continuous Subcutaneous Glucose Monitoring in Children with Type 1 Diabetes," Pediatrics, vol. 107 (2), Feb. 2001, pp. 222-226.

Chia C.W., et al., "Glucose Sensors: Toward Closed Loop Insulin Delivery," Endocrinology and Metabolism Clinics of North America, vol. 33, 2004, pp. 175-195.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Claremont D.J., et al., "Potentially-Implantable, Ferrocene-Mediated Glucose Sensor," Journal of Biomedical Engineering, vol. 8, Jul. 1986, pp. 272-274.

Claremont D.J., et al., "Subcutaneous Implantation of a Ferrocene-Mediated Glucose Sensor in Pigs," Diabetologia, vol. 29, 1986, pp. 817-821.

Clark L.C., et al., "Configurational Cyclic Voltammetry: Increasing the Specificity and Reliability of Implanted Electrodes," IEEE/Ninth Annual Conference of the Engineering in Medicine and Biollogy Society, 1987, pp. 0782-0783.

Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.

Clark L.C., et al., "One-Minute Electrochemical Enzymic Assay for Cholesterol in Biological Materials," Clinical Chemistry, vol. 27 (12), 1981, pp. 1978-1982.

Colangelo V.J., et al., "Corrosion Rate Measurements in Vivo," Journal of Biomedical Materials Research, vol. 1, 1967, pp. 405-414.

Colowick S.P., et al., "Methods in Enzymology," vol. XLIV, Immobilized Enzymes, Edited by Mosbach K, New York Academic Press, 1976, 11 pages.

Coulet P.R., et al., "Enzymes Immobilized on Collagen Membranes: A Tool for Fundamental Research and Enzyme Engineering," Journal of Chromatography, vol. 215, 1981, pp. 65-72.

Coulet P.R., "Polymeric Membranes and Coupled Enzymes in the Design of Biosensors," Journal of Membrane Science, 1992, vol. 68, pp. 217-228.

Cox D.J., et al., "Accuracy of Perceiving Blood Glucose in IDDM," Diabetes Care, vol. 8 (6), Nov.-Dec. 1985, pp. 529-536.

Csoregi E., et al., "Amperometric Microbiosensors for Detection of Hydrogen Peroxide and Glucose Based on Peroxidase-Modified Carbon Fibers," Electroanalysis, vol. 6, 1994, pp. 925-933.

Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.

Danielsson B., et al., "Enzyme Thermistors," Methods in Enzymology, vol. 137, 1988, pp. 181-197.

Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.

Davies M.L., et al., "Polymer Membranes in Clinical Sensor Applications," An overview of membrane function, Biomaterials, vol. 13 (14), 1992, pp. 971-978.

Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.

DuPont, "Dimension® AR Clinical Chemistry System," The Chemistry Analyzer that Makes the most of your Time, Money and Effort, Dade International, Chemistry Systems, Newark, 1998, 18 pages.

Durliat H., et al., "Spectrophotometric and Electrochemical Determinations of L(+)-Lactate in Blood by Use of Lactate Dehydrogenase from Yeast," Clinical Chemistry, vol. 22 (11), 1976, pp. 1802-1805.

Edwards Lifesciences, "Accuracy for You and Your Patients," Marketing materials, 2002, 4 pages.

El Degheidy M.M., et al., "Optimization of an Implantable Coated Wire Glucose Sensor," Journal of Biomedical Engineering, vol. 8, Apr. 1986, pp. 121-129.

El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.

El-Sa'ad L., et al., "Moisture Absorption by Epoxy Resins: The Reverse Thermal Effect," Journal of Materials Science, vol. 25, 1990, pp. 3577-3582.

Ernst H., et al., "Reliable Glucose Monitoring Through the Use of Microsystem Technology," Analytical Bioanalytical Chemistry, vol. 373, 2002, pp. 758-761.

Fabietti P.G., et al., "Clinical Validation of a New Control-Oriented Model of Insulin and Glucose Dynamics in Subjects with Type 1 Diabetes," Diabetes Technology & Therapeutics, vol. 9 (4), 2007, pp. 327-338.

Fahy B.G., et al., "An Analysis: Hyperglycemic Intensive Care Patients Need Continuous Glucose Monitoring-Easier Said Than Done," Journal of Diabetes Science and Technology, Diabetes Technology Society, vol. 2 (2), Mar. 2008, pp. 201-204.

(56) References Cited

OTHER PUBLICATIONS

Fare T.L., et al., "Functional Characterization of a Conducting Polymer-Based Immunoassay System," Biosonsors & Bioelectronics, vol. 13 (3-4), 1998, pp. 459-470.
Feldman B., et al., "A Continuous Glucose Sensor Based on Wired EnzymeTM Technology—Results from a 3-Day Trial in Patients with Type 1 Diabetes," Diabetes Technology & Therapeutics, vol. 5 (5), 2003, pp. 769-779.
File History of U.S. Appl. No. 09/447,227, filed Nov. 22, 1999, 1184 pages.
File History of U.S. Appl. No. 11/654,135, filed Jan. 17, 2007, 519 pages.
File History of U.S. Appl. No. 12/098,353, filed Apr. 4, 2008, 469 pages.
File History of U.S. Appl. No. 12/133,738, filed Jun. 5, 2008, 557 pages.
File History of U.S. Appl. No. 12/133,761, filed Jun. 5, 2008, 585 pages.
File History of U.S. Appl. No. 12/133,786, filed Jun. 5, 2008, 814 pages.
File History of U.S. Appl. No. 12/390,290, filed Feb. 20, 2009, 669 pages.
File History of U.S. Appl. No. 12/536,852, filed Aug. 6, 2009, 480 pages.
File History of U.S. Appl. No. 12/579,385, filed Oct. 14, 2009, 558 pages.
Fischer U., et al., "Assessment of Subcutaneous Glucose Concentration: Validation of the Wick Technique as a Reference for Implanted Electrochemical Sensors in Normal and Diabetic Dogs," Diabetologia, vol. 30, 1987, pp. 940-945.
Fischer U., et al., "Hypoglycaemia-Warning by Means of Subcutaneous Electrochemical Glucose Sensors: An Animal Study," Horm. Metab. Res, vol. 27, 1995, p. 53. (Abstract Only).
Fischer U., et al., "Oxygen Tension at the Subcutaneous Implantation Site of Glucose Sensors," Biomed. Biochim. Acta, vol. 48 (11/12), 1989, pp. 965-971.
Freedman D., et al., "Statistics," Second Edition, W.W. Norton & Company, New York & London, 1991, p. 74 (3 pages).
Frohnauer M.K., et al., "Graphical Human Insulin Time-Activity Profiles Using Standardized Definitions," Diabetes Technology & Therapeutics, vol. 3 (3), 2001, pp. 419-429.
Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.
Gabby R.A., et al., "Optical Coherence Tomography-Based Continuous Noninvasive Glucose Monitoring in Patients with Diabetes," Diabetes Technology & Therapeutics, vol. 10, Nov. 3, 2008, pp. 188-193.
Ganesan N., et al., "Gold Layer-Based Dual Crosslinking Procedure of Glucose Oxidase with Ferrocene Monocarboxylic Acid Provides a Stable Biosensor," Analytical Biochemistry, Notes & Tips, vol. 343, 2005, pp. 188-191.
Ganesh A., et al., "Evaluation of the VIA® Blood Chemistry Monitor for Glucose in Healthy and Diabetic Volunteers," Journal of Diabetes Science and Technology, vol. 2 (2), Mar. 2008, pp. 182-193.
Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.
Gerritsen M., et al., "Performance of Subcutaneously Implanted Glucose Sensors for Continuous Monitoring," The Netherlands Journal of Medicine, vol. 54, 1999, pp. 167-179.
Gerritsen M., et al., "Problems Associated with Subcutaneously Implanted Glucose Sensors," Diabetes Care, vol. 23 (2), Feb. 2000, pp. 143-145.
Gilligan B.J., et al., "Evaluation of a Subcutaneous Glucose Sensor Out to 3 Months in a Dog Model" Diabetes Care, vol. 17 (8), Aug. 1994, pp. 882-887.
Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.
Godsland I.F., et al., "Maximizing the Success Rate of Minimal Model Insulin Sensivity Measurement in Humans: The Importance of Basal Glucose Levels," The Biochemical Society and the Medical Research Society, Clinical Science, vol. 101, 2001, pp. 1-9.
Gouda M.D., et al., "Thermal Inactivation of Glucose Oxidase," The Journal of Biological Chemistry, vol. 278 (27), Issue of Jul. 4, 2003, pp. 24324-24333.
Gough D.A., et al., "Frequency Characterization of Blood Glucose Dynamics," Annals of Biomedical Engineering, vol. 31, 2003, pp. 91-97.
Gough D.A., et al., "Immobilized Glucose Oxidase in Implantable Glucose Sensor Technology," Diabetes Technology & Therapeutics, vol. 2 (3), 2000, pp. 377-380.
Gough D.A., "The implantable Glucose Sensor: An Example of Bioengineering Design," Introduction to Bioengineering, 2001, Chapter 3, pp. 57-66.
Gross T.M., et al., "Efficacy and Reliability of the Continuous Glucose Monitoring System," Diabetes Technology & Therapeutics, vol. 2, Supplement 1, 2000, pp. S19-S26.
Gross T.M., et al., "Performance Evaluation of the Minimed® Continuous Glucose Monitoring System During Patient Home Use," Diabetes Technology & Therapeutics, vol. 2(1), 2000, pp. 49-56.
Guerci B., et al., "Clinical Performance of Cgms in Type 1 Diabetic Patients Treated by Continuous Subcutaneous Insulin Infusion Using Insulin Analogs," Diabetes Care, vol. 26, 2003, pp. 582-589.
Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.
Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.
Hall S.B., et al., "Electrochemical Oxidation of Hydrogen Peroxide at Platinum Electrodes. Part III: Effect of Temperature," Electrochimica Acta, vol. 44, 1999, pp. 2455-2462.
Hall S.B., et al., "Electrochemical Oxidation of Hydrogen Peroxide at Platinum Electrodes. Part Iv: Phosphate Buffer Dependence," Electrochimica Acta, vol. 44, 1999, pp. 4573-4582.
Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.
Hamilton, "Complete Guide to Selecting the Right Hamilton Gastight, Microliter, and Specialty Syringe for your Application," Syringe Selection, www.hamiltoncompany.com, 2006, 20 pages.
Hashiguchi Y., et al., "Development of a Miniaturized Glucose Monitoring System by Combining a Needle-Type Glucose Sensor with Microdialysis Sampling Method: Long-term subcutaneous tissue glucose monitoring in ambulatory diabetic patients," Diabetes Care, vol. 17, No. 5, May 1994, pp. 387-396.
Heller A., "Electrical Connection of Enzyme Redox Centers to Electrodes," J. Phys. Chem., vol. 96, 1992, pp. 3579-3587.
Heller A., "Electrical Wiring of Redox Enzymes," Ace. Chem. Res., vol. 23, 1990, pp. 128-134.
Heller A., "Implanted Electrochemical Glucose Sensors for the Management of Diabetes," Annu. Rev., Biomed Eng., vol. 1, 1999, pp. 153-175.
Heller A., "Plugging Metal Connectors into Enzymes," Nature Biotechnology, vol. 21, No. 6, Jun. 2003, pp. 631-632.
Hicks J.M., "In Situ Monitoring," Clinical Chemistry, vol. 31 (12), 1985, pp. 1931-1935.
Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.
Hoel P.G., "Elementary Statistics," Fourth Edition, John Wiley & Sons, Inc., 1976, pp. 113-114.
Hrapovic S., et al., "Picoamperometric Detection of Glucose at Ultrasmall Platinum-Based Biosensors Preparation and Characterization," Anal. Chem, vol. 75, 2003, pp. 3308-3315.

(56) References Cited

OTHER PUBLICATIONS

Hu Y., et al., "A Needle-Type Enzyme-Based Lactate Sensor for In Vivo Monitoring," Analytica Chimica Acta, vol. 281, 1993, pp. 503-511.
Huang C., et al., "Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode," U.S. Department of Commence/NTIS, 1975, 126 pages.
Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.
Hunter I., et al., "Minimally Invasive Glucose Sensor and Insulin Delivery System," Mit Home Automation and Healthcare Consortium, Mar. 31, 2000, Progress Report No. 25, 17 pages.
International Preliminary Examination Report on for Application No. PCT/US2001/023850 dated Jun. 4, 2003, 3 pages.
International Preliminary Report on Patentability for Application No. PCT/US2004/024263, dated Feb. 6, 2006, 5 pages.
International Preliminary Report on Patentability for Application No. PCT/US2004/038724, dated Feb. 24, 2009, 4 pages.
International Preliminary Report on Patentability for Application No. PCT/US2005/006301, dated Aug. 30, 2006, 4 pages.
International Preliminary Report on Patentability for Application No. PCT/US2005/024993, dated Jan. 16, 2007, 7 pages.
International Preliminary Report on Patentability for Application No. PCT/US2006/024132, dated Dec. 24, 2007, 6 pages.
International Preliminary Report on Patentability for Application No. PCT/US2006/034284, dated Sep. 9, 2008, 6 pages.
International Preliminary Report on Patentability for Application No. PCT/US2008/058158, dated Sep. 29, 2009, 9 pages.
International Preliminary Report on Patentability for Application No. PCT/US2008/066600, dated Dec. 17, 2009, 6 pages.
International Preliminary Report on Patentability for Application No. PCT/US2009/034773 dated Aug. 24, 2010, 13 pages.
International Search Report and Written Opinion for Application No. PCT/US2004/024263, dated Nov. 29, 2004, 6 pages.
International Search Report and Written Opinion for Application No. PCT/US2004/038724, dated Jan. 9, 2006, 4 pages.
International Search Report and Written Opinion for Application No. PCT/US2004/041095, dated Jun. 1, 2005, 5 pages.
International Search Report and Written Opinion for Application No. PCT/US2005/006301, dated Jun. 22, 2005, 4 pages.
International Search Report and Written Opinion for Application No. PCT/US2005/024993, dated Nov. 4, 2005, 12 pages.
International Search Report and Written Opinion for Application No. PCT/US2006/024132, dated Jul. 20, 2007, 6 pages.
International Search Report and Written Opinion for Application No. PCT/US2006/034284, dated Aug. 17, 2007, 6 pages.
International Search Report and Written Opinion for Application No. PCT/US2008/058158, dated Aug. 8, 2008, 10 pages.
International Search Report and Written Opinion for Application No. PCT/US2008/066600, dated Oct. 7, 2008, 6 pages.
International Search Report and Written Opinion for Application No. PCT/US2009/034773 dated Apr. 14, 2009, 13 pages.
International Search Report for Application No. PCT/US2001/023850 dated Jan. 16, 2002, 3 pages.
Ishikawa M., et al., "Initial Evaluation of a 290-Mm Diameter Subcutaneous Glucose Sensor: Glucose Monitoring With a Biocompatible, Flexible-Wire, Enzyme-Based Amperometric Microsensor in Diabetic and Nondiabetic Humans," Journal of Diabetes and Its Complications, vol. 12, 1998, pp. 295-301.
Jaffari S.A., et al., "Recent Advances in Amperometric Glucose Biosensors for In Vivo Monitoring," Physiological Measurement, 1995, vol. 16, pp. 1-15.
Jensen M.B., et al., "Fast Wave Forms for Pulsed Electrochemical Detection of Glucose by Incorporation of Reductive Desorption of Oxidation Products," Analytical Chemistry, vol. 69 (9), May 1997, pp. 1776-1781.

Jeutter D.C., "A Transcutaneous Implanted Battery Recharging and Biotelemeter Power Switching System," IEEE Transactions on Biomedical Engineering, vol. BME-29 (5), May 1982, pp. 314-321.
Jobst G., et al., "Thin-Film Microbiosensors for Glucose-Lactate Monitoring," Anal Chem, Sep. 15, 1996, vol. 68(18), pp. 3173-3179.
Johnson K.W., et al., "In Vivo Evaluation of an Electroenzymatic Glucose Sensor Implanted in Subcutaneous Tissue," Biosensors and Bioelectronics, 1992, vol. 7, pp. 709-714.
Johnson K.W., "Reproducible Electrodeposition of Biomolecules for the Fabrication of Miniature Electroenzymatic Biosensors," Sensors and Actuators B, vol. 5, 1991, pp. 85-89.
Jovanovic L.M.D., "The Role of Continuous Glucose Monitoring in Gestational Diabetes Mellitus," Diabetes Technology and Therapeutics, vol. 2 (1), 2000, pp. S67-S71.
Kacaniklic V., et al., "Amperometric Biosensors for Detection of L- and D-Amino Acids Based on Coimmoblized Peroxidase and L- and D-Amino Acid Oxidases in Carbon Paste Electrodes," Electroanalysis, vol. 6, May-Jun. 1994, pp. 381-390.
Kamath A., et al., "Calibration of a Continuous Glucose Monitor: Effect of Glucose Rate of Change," Eighth Annual Diabetes Technology Meeting, Nov. 13-15, 2008, pp. A88 (2 pages).
Kang S.K., et al., "In Vitro and Short-Term in Vivo Characteristics of a Kel-F Thin Film Modified Glucose Sensor," Analytical Sciences, vol. 19, Nov. 2003, pp. 1481-1486.
Kaplan S.M., "Wiley Electrical and Electronics Engineering Dictionary," IEEE Press, John Wiley & Sons, Inc., 2004, pp. 141, 142, 548 & 549.
Kaufman F.R., et al., "A Pilot Study of the Continuous Glucose Monitoring System," Diabetes Care, vol. 24 (12), Dec. 2001, pp. 2030-2034.
Kaufman F.R., "Role of the Continuous Glucose Monitoring System in Pediatric Patients," Diabetes Technology and Therapeutics, vol. 2 (1), 2000, S49-S52.
Kawagoe J.L., et al., "Enzyme-Modified Organic Conducting Salt Microelectrode," Analytical Chemistry, vol. 63, 1991, pp. 2961-2965.
Kerner, et al., "A Potentially Implantable Enzyme Electrode for Amperometric Measurement of Glucose," Hormone and Metabolic Research Supplement, vol. 20, 1988, pp. 8-13.
Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.
Kiechle F.L., "The Impact of Continuous Glucose Monitoring on Hospital Point-of-Care Testing Programs," Diabetes Technology and Therapeutics, vol. 3 (4), 2001, pp. 647-649.
Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.
Kondo T., et al., "A Miniature Glucose Sensor, Implantable in the Blood Stream," Diabetes Care, vol. 5 (3), May-Jun. 1982, 218-221.
Koschinsky T., et al., "Sensors for Glucose Monitoring: Technical and Clinical Aspects," Diabetes Metabolism Research and Reviews, vol. 17, No. 2, Jan. 1, 2001, pp. 113-123.
Koschinsky T., et al., "New Approach to Technical and Clinical Evaluation of Devices for Self-Monitoring of Blood Glucose," Diabetes Care, vol. 11 (8), Sep. 1988, pp. 619-629.
Kost J., et al., "Glucose-Sensitive Membranes Containing Glucose Oxidase: Activity, Swelling, and Permeability Studies," Journal of Biomedical Materials Research, vol. 19, 1985, pp. 1117-1133.
Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.
Koudelka M., et al., "In-Vivo Behaviour of Hypodermically Implanted Microfabricated Glucose Sensors," Biosensors and Bioelectronics, vol. 6, 1991, pp. 31-36.
Kraver., et al., "A Mixed-Signal Sensor Interface Microinstrument," Sensors and Actuators A, Physical 2001, vol. 91, pp. 266-277.
Kruger D., et al., "Psychological Motivation and Patient Education: A Role for Continuous Glucose Monitoring," Diabetes Technology and Therapeutics, vol. 2 (1), 2000, pp. S93-S97.

(56) References Cited

OTHER PUBLICATIONS

Kulys J., et al., "Carbon-Paste Biosensors Array for Long-Term Glucose Measurement," Biosensors & Bioelectronics, vol. 9, 1994, pp. 491-500.
Kunjan K., et al., "Automated Blood Sampling and Glucose Sensing in Critical Care Settings," Journal of Diabetes Science and Technology, vol. 2 (2), Mar. 2008, pp. 194-200.
Kurnik R.T., et al., "Application of the Mixtures of Experts Algorithm for Signal Processing in a Noninvasive Glucose Monitoring System," Sensors and Actuators B, vol. 60, 1999, pp. 19-26.
Kurtz T.W., et al., "Recommendations for Blood Pressure Measurement in Humans and Experimental Animals, Part 2: Blood Pressure Measurement in Experimental Animals: A Statement for Professionals From the Subcommittee of Professional and Public Education of the American Heart Association Council on High Blood Pressure Research," Hypertension, Feb. 2005, vol. 45, pp. 299-310.
Ladd M.F.C., et al., "Structure Determination by X-Ray Crystallography," 3rd Edition, Plenum Press, 1994, Ch. 1, pp. xxi-xxiv and 1-58.
Lehmann E.D., et al., Retrospective Validation of a Physiological Model of Glucose-Insulin Interaction in Type 1 Diabetes Mellitus. Medical Engineering & Physics, vol. 16, May 1994, pp. 193-202.
Lerner., et al., "An Implantable Electrochemical Glucose Sensor," Ann. N. Y. Acad. Sci., vol. 428, May 1984, pp. 263-278.
Lewandowski J.J., et al., "Evaluation of a Miniature Blood Glucose Sensor," Transactions—American Society for Artificial Internal Organs, vol. 34, 1988, pp. 255-258.
Leypoldt J.K., et al., "Model of a Two-Substrate Enzyme Electrode for Glucose," Analytical Chemistry, vol. 56, 1984, pp. 2896-2904.
Linke B., et al., "Amperometric Biosensor for In Vivo Glucose Sensing Based on Glucose Oxidase Immobilized in a Redox Hydrogel," Biosensors and Bioelectronics, vol. 9, 1994, pp. 151-158.
Lohn A., et al., "A Knowledge-Based System for Real-Time Validation of Calibrations and Measurements," Chemometrics and Intelligent Laboratory Systems, vol. 46, 1999, pp. 57-66.
Lowe C.R., "Biosensors," Trends in Biotechnology, vol. 2 (3), 1984, pp. 59-65.
Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.
Lyandres O., et al. "Progress toward an In Vivo Surface-Enhanced Raman Spectroscopy Glucose Sensor," Diabetes Technology and Therapeutics, vol. 10 (4), 2008, pp. 257-265.
Maidan R., et al., "Elimination of Electrooxidizable Interferent-Produced Currents in Amperometric Biosensors," Analytical Chemistry, vol. 64, 1992, pp. 2889-2896.
Makale M.T., et al., "Tissue Window Chamber System for Validation of Implanted Oxygen Sensors," American Journal of Physiology—Heart and Circulatory Physiology, vol. 284, Feb. 21, 2003, pp. 1-27.
Malin S.F., et al., "Noninvasive Prediction of Glucose by Near-Infrared Diffuse Reflectance Spectroscopy," Clinical Chemistry, vol. 45 (9), 1999, pp. 1651-1658.
Maran A., et al., "Continuous Subcutaneous Glucose Monitoring in Diabetic Patients," A Multicenter Analysis, Diabetes Care, vol. 25 (2), Feb. 2002, pp. 347-352.
March W.F., "Dealing with the Delay," Diabetes Technology & Therapeutics, vol. 4 (1), 2002, pp. 49-50.
Marena S., et al., "The Artificial Endocrine Pancreas in Clinical Practice and Research," Panminerva Medica, vol. 35 (2), 1993, pp. 67-74.
Martin R.F., "General Deming Regression for Estimating Systematic Bias and its Confidence Interval in Method-Comparison Studies," Clinical Chemistry, vol. 46 (1), 2000, pp. 100-104.
Mastrototaro J.J., et al., "An Electroenzymatic Glucose Sensor Fabricated on a Flexible Substrate," Sensors and Actuators B, vol. 5, 1991, pp. 139-144.
Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.
Mastrototaro J.J., "The MiniMed Continuous Glucose Monitoring System," Diabetes Technology & Therapeutics, vol. 2, Supplement 1, 2000, pp. S13-S18.
Matsumoto T., et al., "A Micro-Planar Amperometric Glucose Sensor Unsusceptible to Interference Species," Sensors and Actuators B, 49, 1998, pp. 68-72.
Matthews D.R., et al., "An Amperometric Needle-Type Glucose Sensor Testing in Rats and Man," Diabetic Medicine, vol. 5, 1988, pp. 248-252.
Mazze R.S., et al., "Characterizing Glucose Exposure for Individuals with Normal Glucose Tolerance Using Continuous Glucose Monitoring and Ambulatory Glucose Profile Analysis," Diabetes Technology & Therapeutics, vol. 10 (3), 2008, pp. 149-159.
Mazzola F., et al., "Video Diabetes: A Teaching Tool for Children with Insulin-Dependent Diabetes," IEEE, Proceedings 7th Annual Symposium on Computer Applications in Medical Care, Oct. 1983, 1 page Abstract.
McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.
McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.
McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.
Memoli A., et al., "A Comparison between Different Immobilised Glucoseoxidase-Based Electrodes," Journal of Pharmaceutical and Biomedical Analysis, vol. 29, 2002, pp. 1045-1052.
Merriam-Webster Online Dictionary, Definition of "Acceleration" retrieved from http://www.merriam-webster.com/dictionary/Acceleration, Jan. 11, 2010, 1 page.
Merriam-Webster Online Dictionary, Definition of "System". http://www.merriamwebster.com/dictionary/System, Jan. 11, 2010, 2 pages.
Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.
Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.
Moatti-Sirat D., et al., "Reduction of Acetaminophen Interference in Glucose Sensors by a Composite Nafion Membrane: Demonstration in Rats and Man," Diabetologia, vol. 37 (6), Jun. 1994, pp. 610-616.
Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.
Morff R.J., et al., "Microfabrication of Reproducible, Economical, Electroenzymatic Glucose Sensors," Annual International Conference of the IEEE Engineering in Medicine and Biology Society, vol. 12 (2), 1990, pp. 0483-0484.
Mosbach K., et al., "Determination of Heat Changes in the Proximity of Immobilized Enzymes with an Enzyme Thermistor and its Use for the Assay of Metabolites," Biochimica Biophysica Acta, vol. 403, 1975, pp. 256-265.
Motonaka J., et al., "Determination of Cholesterol and Cholesterol Ester with Novel enzyme Microsensors," Anal. Chem., vol. 65, 1993, pp. 3258-3261.
Moussy F., et al., "Performance of Subcutaneously Implanted Needle-Type Glucose Sensors Employing a Novel Trilayer Coating," Analytical Chemistry, vol. 65, Aug. 1, 1993, pp. 2072-2077.
Moussy F., "Implantable Glucose Sensor: Progress and Problems," IEEE, Nov. 2002, pp. 270-273.
Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.
Muslu, "Trickling Filter Performance," Applied Biochemistry and Biotechnology, vol. 37, 1992, pp. 211-224.

(56) References Cited

OTHER PUBLICATIONS

Nintendo Healthcare, Wired, Dec. 1993, 1 page.
Office Action for European Application No. 05723951.9, dated Jan. 28, 2011, 6 pages.
Office Action for U.S. Appl. No. 09/636,369, dated Sep. 30, 2002, 4 pages.
Office Action for U.S. Appl. No. 10/632,537, dated Dec. 21, 2004, 7 pages.
Office Action for U.S. Appl. No. 10/632,537, dated Oct. 20, 2004, 7 pages.
Office Action for U.S. Appl. No. 10/633,329, dated Dec. 18, 2008, 9 pages.
Office Action for U.S. Appl. No. 10/633,329, dated Feb. 4, 2008, 7 pages.
Office Action for U.S. Appl. No. 10/633,329, dated Jul. 30, 2007, 9 pages.
Office Action for U.S. Appl. No. 10/633,329, dated Jun. 11, 2009, 8 pages.
Office Action for U.S. Appl. No. 10/633,329, dated Jun. 12, 2008, 7 pages.
Office Action for U.S. Appl. No. 10/633,329, dated Mar. 26, 2007, 05 pages.
Office Action for U.S. Appl. No. 10/633,329, dated Oct. 5, 2006, 6 pages.
Office Action for U.S. Appl. No. 10/633,367, dated Jul. 15, 2008, 8 pages.
Office Action for U.S. Appl. No. 10/633,367, dated Jun. 11, 2009, 7 pages.
Office Action for U.S. Appl. No. 10/633,404, dated Feb. 12, 2007, 14 pages.
Office Action for U.S. Appl. No. 10/648,849, dated Jun. 23, 2009, 10 pages.
Office Action for U.S. Appl. No. 10/789,359, dated Mar. 20, 2008, 7 pages.
Office Action for U.S. Appl. No. 10/789,359, dated Nov. 27, 2006, 10 pages.
Office Action for U.S. Appl. No. 10/789,359, dated Oct. 3, 2008, 7 pages.
Office Action for U.S. Appl. No. 10/838,909, dated Jun. 5, 2008, 8 pages.
Office Action for U.S. Appl. No. 10/838,909, dated Mar. 16, 2009, 12 pages.
Office Action for U.S. Appl. No. 10/896,772, dated Dec. 14, 2005, 10 pages.
Office Action for U.S. Appl. No. 10/896,772, dated Jan. 11, 2005, 16 pages.
Office Action for U.S. Appl. No. 10/896,772, dated Jul. 19, 2005, 17 pages.
Office Action for U.S. Appl. No. 10/896,772, dated May 22, 2006, 31 pages.
Office Action for U.S. Appl. No. 10/991,966, dated Jul. 22, 2008, 12 pages.
Office Action for U.S. Appl. No. 10/991,966, dated Nov. 28, 2007, 13 pages.
Office Action for U.S. Appl. No. 11/007,635, dated Jan. 27, 2006, 9 pages.
Office Action for U.S. Appl. No. 11/007,920, dated Jun. 24, 2008, 10 pages.
Office Action for U.S. Appl. No. 11/034,344, dated Jan. 15, 2008, 5 pages.
Office Action for U.S. Appl. No. 11/038,340, dated Jan. 5, 2009, 13 pages.
Office Action for U.S. Appl. No. 11/038,340, dated Jun. 17, 2008, 11 pages.
Office Action for U.S. Appl. No. 11/038,340, dated May 19, 2009, 14 pages.
Office Action for U.S. Appl. No. 11/077,714, dated Apr. 10, 2007, 16 pages.
Office Action for U.S. Appl. No. 11/077,714, dated Apr. 16, 2009, 12 pages.
Office Action for U.S. Appl. No. 11/077,714, dated Jan. 10, 2008, 18 pages.
Office Action for U.S. Appl. No. 11/077,714, dated Jul. 27, 2007, 13 pages.
Office Action for U.S. Appl. No. 11/077,714, dated Oct. 11, 2006, 9 pages.
Office Action for U.S. Appl. No. 11/077,714, dated Sep. 16, 2008, 16 pages.
Office Action for U.S. Appl. No. 11/077,739, dated Jul. 21, 2009, 8 pages.
Office Action for U.S. Appl. No. 11/077,740, dated Apr. 28, 2009, 27 pages.
Office Action for U.S. Appl. No. 11/077,740, dated Feb. 7, 2008, 16 pages.
Office Action for U.S. Appl. No. 11/077,740, dated Jul. 25, 2008, 24 pages.
Office Action for U.S. Appl. No. 11/077,740, dated Jun. 1, 2007, 14 pages.
Office Action for U.S. Appl. No. 11/077,740, dated Nov. 1, 2007, 13 pages.
Office Action for U.S. Appl. No. 11/077,759, dated Jul. 10, 2008, 10 pages.
Office Action for U.S. Appl. No. 11/077,759, dated Mar. 31, 2008, 16 pages.
Office Action for U.S. Appl. No. 11/077,759, dated May 26, 2009, 8 pages.
Office Action for U.S. Appl. No. 11/077,765, dated Dec. 31, 2007, 10 pages.
Office Action for U.S. Appl. No. 11/077,765, dated Jan. 23, 2009, 11 pages.
Office Action for U.S. Appl. No. 11/077,765, dated May 16, 2008, 9 pages.
Office Action for U.S. Appl. No. 11/077,765, dated Sep. 19, 2008, 9 pages.
Office Action for U.S. Appl. No. 11/078,232, dated Jul. 21, 2009, 13 pages.
Office Action for U.S. Appl. No. 11/078,232, dated Mar. 5, 2009, 14 pages.
Office Action for U.S. Appl. No. 11/078,232, dated May 5, 2008, 21 pages.
Office Action for U.S. Appl. No. 11/078,232, dated Nov. 12, 2008, 28 pages.
Office Action for U.S. Appl. No. 11/157,365, dated Jan. 7, 2009, 10 pages.
Office Action for U.S. Appl. No. 11/157,365, dated Jul. 21, 2009, 9 pages.
Office Action for U.S. Appl. No. 11/157,365, dated Jun. 26, 2008, 11 pages.
Office Action for U.S. Appl. No. 11/333,837, dated Jun. 29, 2009, 13 pages.
Office Action for U.S. Appl. No. 11/333,837, dated Nov. 28, 2008, 11 pages.
Office Action for U.S. Appl. No. 11/334,876, dated Aug. 26, 2008, 8 pages.
Office Action for U.S. Appl. No. 11/334,876, dated May 2, 2008, 18 pages.
Office Action for U.S. Appl. No. 11/334,876, dated Oct. 4, 2006, 9 pages.
Office Action for U.S. Appl. No. 11/334,876, dated Sep. 25, 2007, 14 pages.
Office Action for U.S. Appl. No. 11/360,252, dated Jan. 29, 2009, 15 pages.
Office Action for U.S. Appl. No. 11/360,252, dated Jul. 23, 2009, 10 pages.
Office Action for U.S. Appl. No. 11/360,252, dated Jun. 30, 2008, 10 pages.
Office Action for U.S. Appl. No. 11/360,819, dated Apr. 7, 2010, 10 pages.
Office Action for U.S. Appl. No. 11/360,819, dated Aug. 11, 2008, 10 pages.
Office Action for U.S. Appl. No. 11/360,819, dated Dec. 26, 2008, 12 pages.

(56) References Cited

OTHER PUBLICATIONS

Office Action for U.S. Appl. No. 11/360,819, dated Oct. 29, 2009, 15 pages.
Office Action for U.S. Appl. No. 11/360,819, dated Sep. 2, 2010, 8 pages.
Office Action for U.S. Appl. No. 12/102,729, dated Jul. 7, 2009, 7 pages.
Office Action for U.S. Appl. No. 12/102,745, dated Dec. 23, 2008, 4 pages.
Office Action for U.S. Appl. No. 12/364,786, dated Jul. 29, 2010, 6 pages.
Office Action for U.S. Appl. No. 95/001,038, dated Jun. 17, 2008, 32 pages.
Office Action for U.S. Appl. No. 95/001,039, dated May 29, 2008, 21 pages.
Office Action from European Patent Application No. 05723951.9, dated Sep. 7, 2010, 5 pages.
Office Action from European Patent Application No. 05771646.6, dated Aug. 19, 2009, 4 pages.
Office Action from Japanese Patent Application No. 2006-522016, dated Aug. 31, 2010, 6 pages.
Ohara T.J., et al., "Glucose Electrodes Based on Cross-Linked [Os(bpy)2Cl](+/2+) Complexed Poly(1-Vinylimidazole) Films," Analytical Chemistry, vol. 65, Dec. 1993, pp. 3512-3517.
Ohara T.J., et al., ""Wired" Enzyme Electrodes for Amperometric Determination of Glucose or Lactate in the Presence of Interfering Substances," Anal Chem, vol. 66, 1994, pp. 2451-2457.
Okuda, et al., "Mutarotase Effect on Micro Determinations of D-Glucose and its Anomers with β D-Glucose Oxidase," Anal Biochem, vol. 43 (1), 1971, pp. 312-315.
Oxford English Dictionary Online, Definition of "Impending," http://www.askoxford.com/results/?view=devdict&field-12668446_Impending&branch=, Jan. 11, 2010, 1 page.
Palmisano F., et al., "Simultaneous Monitoring of Glucose and Lactate by an Interference and Cross-Talk Free Dual Electrode Amperometric Biosensor Based on Electropolymerized Thin Films," Biosensors & Bioelectronics, vol. 15, 2000, pp. 531-539.
Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.
Peacock W.F., et al., "Cardiac Troponin and Outcome in Acute Heart Failure," N. Engl. J. Med., vol. 358, 2008, pp. 2117-2126.
Peguin S., et al., "Pyruvate Oxidase and Oxaloacetate Decarbozylase Enzyme Electrodes—Simultaneous Determination of Transaminases with a Two-electrode-based Analyzer," Analytica Chimica Acta, vol. 222, 1989, pp. 83-93.
Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.
Pfeiffer E.F., "The Glucose Sensor: The Missing Link in Diabetes Therapy," Horm Metab Res Suppl., vol. 24, 1990, pp. 154-164.
Phillips R.P., "A High Capacity Transcutaneous Energy Transmission System," ASIAO Journal, vol. 41, 1995, pp. M259-M262.
Pichert J.W., et al., "Issues for the Coming Age of Continuous Glucose Monitoring," Diabetes Educator, vol. 26 (6), Nov.-Dec. 2000, pp. 969-980.
Pickup J.C., et al., "Developing Glucose Sensors for In Vivo Use," Elsevier Science Publishers Ltd (Uk), Tibtech, vol. 11, 1993, pp. 285-291.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pickup J.C., et al., "Potentially-Implantable, Amperometric Glucose Sensors with Mediated Electron Transfer: Improving the Operating Stability," Biosensors, vol. 4, 1989, pp. 109-119.
Pinner S.H., et al., "Cross-Linking of Cellulose Acetate by Ionizing Radiation," Nature, vol. 184, Oct. 24, 1959, pp. 1303-1304.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Pitzer K.R., et al., "Detection of Hypogylcemia with the Glucowatch Biographer," Diabetes Care, vol. 24 (5), 2001, pp. 881-885.
Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.
Poitout V., et al., "Development of a Glucose Sensor for Glucose Monitoring in Man: The Disposable Implant Concept," Clinical Materials, vol. 15, 1994, pp. 241-246.
Poitout V., et al., "In Vitro and In Vivo Evaluation in Dogs of a Miniaturized Glucose Sensor," Asaio Transactions, vol. 37, 1991, pp. M298-M300.
Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.
Prabhu V.G., et al., "Electrochemical Studies of Hydrogen Peroxide at a Platinum Disc Electrode," Electrochimica Acta, vol. 26 (6), 1981, pp. 725-729.
Quinn C.A.P., et al., "Biocompatible, Glucose-Permeable Hydrogel for in situ Coating of Implantable Biosensors," Biomaterials, vol. 18 (24), 1997, pp. 1665-1670.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Rabah M.A., et al., "Electrochemical Wear of Graphite Anodes During Electrolysis of Brine," Carbon, vol. 29 (2), 1991, pp. 165-171.
Raya Systems Pioneers, "Raya Systems Pioneers Healthy Video Games," PlayRight, Nov. 1993, pp. 14-15.
Reach G., "A Method for Evaluating in vivo the Functional Characteristics of Glucose Sensors," Biosensors, vol. 2, 1986, pp. 211-220.
Reach G., et al., "Can Continuous Glucose Monitoring Be Used for the Treatment of Diabetes?," Analytical Chemistry, vol. 64 (6), Mar. 15, 1992, pp. 381A-386A.
Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.
Rebrin K., et al., "Automated Feedback Control of Subcutaneous Glucose Concentration in Diabetic Dogs," Diabetologia, vol. 32, 1989, pp. 573-576.
Rebrin K., et al., "Subcutaneous Glucose Monitoring by Means of Electrochemical Sensors: Fiction or Reality?," Journal of Biomedical Engineering, vol. 14, Jan. 1992, pp. 33-40.
Reush, "Organometallic Compounds," Chemical Reactivity, Virtual Textbook of Organic Chemistry, Retrieved from http://www.cem.msu.edu/-reuschlVirtualText/orgmetal.htm, 2004, pp. 1-16.
Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.
Rigla M., et al., "Real-Time Continuous Glucose Monitoring Together with Telemedical Assistance Improves Glycemic Control and Glucose Stability in Pump-Treated Patients," Diabetes Technology & Therapeutics, vol. 10 (3), 2008, pp. 194-199.
Rinken T., et al., "Calibration of Glucose Biosensors by Using Pre-Steady State Kinetic Data," Biosensors & Bioelectronics, vol. 13, 1998, pp. 801-807.
Rivers E.P., et al., "Central Venous Oxygen Saturation Monitoring in the Critically Ill Patient," Current Opinion in Critical Care, 2001, vol. 7, pp. 204-211.

(56) References Cited

OTHER PUBLICATIONS

Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.

Sakakida M., et al., "Ferrocene-Mediated Needle Type Glucose Sensor Covered with Newly Designed Biocompatible Membrane," Sensors and Actuators B, vol. 13-14, 1993, pp. 319-322.

Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.

Samuels M.P., "The Effects of Flight and Altitude," Arch Dis Child, vol. 89, 2004, pp. 448-455.

San Diego Plastics Inc, "Polyethylene," Datasheet, Retrieved from http://www.sdplastics.com/polyeth.html on Aug. 19, 2009, 7 pages.

Sansen W., et al., "A Smart Sensor for the Voltammetric Measurement of Oxygen or Glucose Concentrations," Sensors and Actuators B1, 1990, pp. 298-302.

Sansen W., et al., "Glucose Sensor with Telemetry System," In Implantable Sensors for Closed Loop Prosthetic Systems edited by Ko W.H, Chapter 12, 1985, pp. 167-175.

Schaffar B.P.H., "Thick Film Biosensors for Metabolites in Undiluted Whole Blood and Plasma Samples," Analytical Bioanalytical Chemistry, Dec. 2001, vol. 372, pp. 254-260.

Schmidt F.J., et al., "Calibration of a Wearable Glucose Sensor," The International Journal of Artificial Organs, Wichtig Publishing, IT, vol. 15 (1), Jan. 1, 1992, pp. 55-61.

Schmidt F.J., et al., "Glucose Concentration in Subcutaneous Extracellular Space," Diabetes Care, vol. 16 (5), May 1993, pp. 695-700.

Schmidtke D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Analytical Chemistry, vol. 70 (10), May 15, 1998, pp. 2149-2155.

Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.

Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.

Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.

Service F.J., et al., "Mean Amplitude of Glycemic Excursions, A Measure of Diabetic Instability," Diabetes, vol. 19 (9), Sep. 1970, pp. 644-655.

Service F.J., et al., "Measurements of Glucose Control," Diabetes Care, vol. 10 (2), Mar.-Apr. 1987, pp. 225-237.

Service R.F., "Can Sensors Make a Home in the Body?," Science, Materials Science: Soft Surface, vol. 297, Aug. 9, 2002, pp. 962-963.

Sharkawy A.A., et al., "Engineering the Tissue Which Encapsulates Subcutaneous Implants. I. Diffusion Properties," Journal of Biomedical Materials Research, vol. 37, 1996, pp. 401-412.

Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.

Shichiri M., et al., "Glycaemic Control in Pancreatectomized Dogs with a Wearable Artificial Endocrine Pancreas," Diabetologia, vol. 24, 1983, pp. 179-184.

Shichiri M., et al., "Needle Type Glucose Sensor for Wearable Artificial Endocrine Pancreas," in Implantable Sensors for Closed-Loop Prosthetic Systems edited by Ko W.H, Chapter 15, 1985, pp. 197-210.

Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.

Shichiri M., et al., "Wearable Artificial Endocrine Pancreas with Needle-Type Glucose Sensor," Preliminary Communication, Lancet, vol. 2, Nov. 20, 1982, pp. 1129-1131.

Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.

Sigma-Aldrich Corp. "Nafion® 117 Solution Product Description, Product No. 70160," retrieved from https//:www.sigmaaldrich.com/cgi-bin/hsrun/Suite7/Suite/HAHTpage/Suite.HsExternalProd on Apr. 7, 2005, 1 page.

Skyler J.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.

Slater-MacLean L., et al., "Accuracy of Glycemic Measurements in the Critically Ill," Diabetes Technology and Therapeutics, vol. 10 (3), 2008, pp. 169-177.

Smith B., et al., "An Externally Powered, Multichannel, Implantable Stimulator-Telemeter for Control of Paralyzed Muscle," IEEE Transactions on Biomedical Engineering, vol. 45 (4), Apr. 1998, pp. 463-475.

Sokol L., et al., "Immobilized-Enzyme Rate-Determination Method for Glucose Analysis," Clinical Chemistry, vol. 26 (1), 1980, pp. 89-92.

Sokolov S., et al., "Metrological Opportunities of the Dynamic Mode of Operating an Enzyme Amperometric Biosensor," Medical Engineering & Physics, vol. 17 (6), 1995, pp. 471-476.

Sparacino G., et al., "Continuous Glucose Monitoring Time Series and Hypo-Hyperglycemia Prevention: Requirements, Methods, Open Problems," Current Diabetes Reviews, vol. 4 (3), 2008, pp. 181-192.

Sproule B.A., et al., "Fuzzy Pharmacology: Theory and Applications," Trends in Pharmacological Sciences, vol. 23 (9), Sep. 2002, pp. 412-417.

Sriyudthsak M., et al., "Enzyme-Epoxy Membrane Based Glucose Analyzing System and Medical Applications," Biosensors & Bioelectronics, vol. 11 (8), 1996, pp. 735-742.

Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.

Stern M., et al., "Electrochemical Polarization: I. A Theoretical Analysis of the Shape of Polarization Curves," Journal of the Electrochemical Society, vol. 104 (1), Jan. 1957, pp. 56-63.

Sternberg R., et al., "Study and Development of Multilayer Needle-type Enzyme Based Glucose Microsensors," Biosensors, vol. 4, 1988, pp. 27-40.

Street J.O., et al., "A Note on Computing Robust Regression Estimates Via Iteratively Reweighted Least Squares," The American Statistician, vol. 42 (2), May 1988, pp. 152-154.

Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.

Takatsu I., et al., "Solid State Biosensors Using Thin-Film Electrodes," Sensors and Actuators, 1987, vol. 11, pp. 309-317.

Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.

Tanenberg R.J., et al., "Continuous Glucose Monitoring System: A New Approach to the Diagnosis of Diabetic Gastroparesis," Diabetes Technology & Therapeutics, vol. 2, Supplement 1, 2000, pp. S73-S80.

Tatsuma T., et al., "Oxidase/Peroxidase Bilayer-Modified Electrodes as Sensors for Lactate, Pyruvate, Cholesterol and Uric Acid," Analytica Chimica Acta, vol. 242, 1991, pp. 85-89.

(56) References Cited

OTHER PUBLICATIONS

Thijssen, et al., "A Kalman Filter for Calibration, Evaluation of Unknown Samples and Quality Control in Drifting Systems," Part 1,Theory and Simulations, Analytica chimica Acta, 1984, vol. 156, pp. 87-101.
Thijssen, et al., "A Kalman Filter for Calibration, Evaluation of Unknown Samples and Quality Control in Drifting Systems," Part 3,Variance Reduction ,Analytica chimica Acta, 1985, vol. 173, pp. 265-272.
Thijssen, et al., "A Kalman Filter for Calibration, Evaluation of Unknown Samples and Quality Control in Drifting Systems," Part 4,Flow Injection Analysis, Analytica chimica Acta, 1985, vol. 174, pp. 27-40.
Thijssen P.C.,"A Kalman Filter for Calibration, Evaluation of Unknown Samples and Quality Control in Drifting Systems," Part 2,Optimal Designs, Analytica chimica Acta, vol. 162, 1984, pp. 253-262.
Thome V., et al., "(Abstract) Can the Decrease in Subcutaneous Glucose Concentration Precede the Decrease in Blood Glucose Level? Proposition for a Push-Pull Kinetics Hypothesis," Horm. metab. Res., vol. 27, 1995, p. 53.
Thome-Duret V., et al., "Continuous Glucose Monitoring in the Free-Moving Rat," Metabolism, vol. 47 (7), Jul. 1998, pp. 799-803.
Thome-Duret V., et al., "Modification of the Sensitivity of Glucose Sensor Implanted into Subcutaneous Tissue," Diabetes & Metabolism, vol. 22, 1996, pp. 174-178.
Thome-Duret V., et al., "Use of a Subcutaneous Glucose Sensor to Detect Decreases in Glucose Concentration Prior to Observation in Blood," Analytical Chemistry, vol. 68 (21), Nov. 1, 1996, pp. 3822-3826.
Thompson M., et al., "In Vivo Probes: Problems and Perspectives," Clinical Biochemistry, vol. 19 (5), Oct. 1986, pp. 255-261.
Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.
Tierney M.J., et al., "The Gluco Watch® Biographer: A Frequent, Automatic and Noninvasive Glucose Monitor," Annals of Medicine, vol. 32, 2000, pp. 632-641.
Tilbury J.B., et al., "Receiver Operating Characteristic Analysis for Intelligent Medical Systems—A New Approach for Finding Confidence Intervals," IEEE Transactions on Biomedical Engineering, vol. 47 (7), Jul. 2000, pp. 952-963.
Torjman M.C., et al., "Glucose Monitoring in Acute Care: Technologies on the Horizon," Journal of Diabetes Science and Technology, vol. 2 (2), Mar. 2008, pp. 178-181.
Trajanoski Z., et al., "Neural Predictive Controller for Insulin Delivery Using the Subcutaneous Route," IEEE Transactions on Biomedical Engineering, vol. 45(9), 1998, pp. 1122-1134.
Trecroci D., "A Glimpse into the Future-Continuous Monitoring of Glucose with a Microfiber," Diabetes Interview, Jul. 2002, pp. 42-43.
Tse P.S.H., et al., "Time-Dependent Inactivation of Immobilized Glucose Oxidase and Catalase," Biotechnology & Bioengineering, vol. 29, 1987, pp. 705-713.
Turner A.P.F., et al., "Carbon Monoxide: Acceptor Oxidoreductase from Pseudomonas Thermocarboxydovorans Strain C2 and its Use in a Carbon Monoxide Sensor," Analytica Chimica Acta, vol. 163, 1984, pp. 161-174.
Turner A.P.F., et al., "Diabetes Mellitus: Biosensors for Research and Management," Biosensors, vol. 1, 1985, pp. 85-115.
Unger J., et al., "Glucose Control in the Hospitalized Patient," Emergency Medicine, vol. 36 (9), 2004, pp. 12-18.
Updike S.J., et al., "A Subcutaneous Glucose Sensor with Improved Longevity, Dynamic Range, and Stability of Calibration," Diabetes Care, vol. 23 (2), Feb. 2000, pp. 208-214.
Updike S.J., et al., "Continuous Glucose Monitor Based on an Immobilized Enzyme Electrode Detector," Journal of Laboratory and Clinical Medicine, vol. 93(4), 1979, pp. 518-527.
Updike S.J., et al., "Enzymatic Glucose Sensor: Improved Long-Term Performance in Vitro and in Vivo," ASAIO Journal, vol. 40 (2), Apr.-Jun. 1994, pp. 157-163.
Updike S.J., et al., "Implanting the Glucose Enzyme Electrode: Problems, Progress, and Alternative Solutions," Diabetes Care, vol. 5 (3), May-Jun. 1982, pp. 207-212.
Updike S.J., et al., "Laboratory Evaluation of New Reusable Blood Glucose Sensor," Diabetes Care, vol. 11 (10), Nov.-Dec. 1988, pp. 801-807.
Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.
Updike S.J., et al., "The Enzyme Electrode," Nature, vol. 214, Jun. 3, 1967, pp. 986-988.
Utah Medical Products Inc., "Deltran—Disposable Blood Pressure Tranducers," Product Specifications, 2003-2006, 6 pages.
Vadgama P., "Diffusion Limited Enzyme Electrodes," NATO ASI Series: Series C, Math and Phys. Sci, vol. 226, 1988, pp. 359-377.
Vadgama P., "Enzyme Electrodes as Practical Biosensors," Journal of Medical Engineering & Technology, vol. 5 (6), Nov. 1981, pp. 293-298.
Van Den Berghe, "Tight Blood Glucose Control with Insulin in "Real-Life" Intensive Care," Mayo Clinic Proceedings, vol. 79 (8), Aug. 2004, pp. 977-978.
Velho G., et al., "In Vitro and In Vivo Stability of Electrode Potentials in Needle-Type Glucose Sensors," Influence of Needle Material, Diabetes, vol. 38, Feb. 1989, pp. 164-171.
Velho G., et al., "Strategies for Calibrating a Subcutaneous Glucose Sensor," Biomed Biochim Acta, vol. 48 (11/12), 1989, pp. 957-964.
Von Woedtke T., et al., "In Situ Calibration of Implanted Electrochemical Glucose Sensors," Biomed. Biochim. Acta 48 vol. 11/12, 1989, pp. 943-952.
Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.
Wang J., et al., "Highly Selective Membrane-Free Mediator-Free Glucose Biosensor," Analytical Chemistry, vol. 66 (21), Nov. 1, 1994, pp. 3600-3603.
Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.
Ward, et al., "A Wire-Based Dual-Analyte Sensor for Glucose and Lactate: In Vitro and In Vivo Evaluation," Diabetes Technology and Therapeutics, 2004, vol. 6 (3), pp. 389-401.
Ward W.K., et al., "A New Amperometric Glucose Microsensor: In Vitro and Short-Term In Vivo Evaluation," Biosensors & Bioelectronics, vol. 17, 2002, pp. 181-189.
Ward W.K., et al., "Assessment of Chronically Subcutaneous Glucose Sensors in Dogs: The Effect of Surrounding Fluid Masses," ASAIO Journal, 1999, vol. 45 (6), pp. 555-561.
Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.
Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.
Wientjes K.J.C., "Development of a Glucose Sensor for Diabetic Patients," (Ph.D. Thesis), 2000, 212 pages.
Wikipedia., "Intravenous Therapy," http://en.wikipedia.org/wiki/Intravenous_therapy, Aug. 15, 2006, 6 pages.
Wilkins E., et al., "Glucose Monitoring: State of the Art and Future Possibilities," Med. Eng. Phys., vol. 18 (4), 1996, pp. 273-288.
Wilkins E., et al., "Integrated Implantable Device for Long-Term Glucose Monitoring," Biosensors & Bioelectronics, vol. 10, 1995, pp. 485-494.
Wilkins E.S., et al., "The Coated Wire Electrode Glucose Sensor," Horm Metab Res Suppl., vol. 20, 1988, pp. 50-55.

(56) References Cited

OTHER PUBLICATIONS

Wilson G.S., et al., "Enzyme-Based Biosensors for In Vivo Measurements," Chem. Rev., vol. 100, 2000, pp. 2693-2704.
Wilson G.S., et al., "Progress Toward the Development of an Implantable Sensor for Glucose," Clinical Chemistry, vol. 38 (9), 1992, pp. 1613-1617.
Wood W D., et al., "Hermetic Sealing with Epoxy," Pave Technology—Mechanical Engineering, Mar. 1990, 3 pages.
Woodward S.C., "How Fibroblasts and Giant Cells Encapsulate Implants: Considerations in Design of Glucose Sensor," Diabetes Care, vol. 5 (3) May-Jun. 1982, pp. 278-281.
Worsley G.J et al., "Measurement of Glucose in Blood with a Phenylboronic Acid Optical Sensor," Journal of Diabetes Science and Technology, vol. 2 (2), Mar. 2008, pp. 213-220.
Wright M., et al., "Bioelectrochemical Dehalogenations Via Direct Electrochemistry of Poly(ethylene oxide)-Modified Myoglobin," Electrochemistry Communications, vol. 1, 1999, pp. 609-613.
Wu H., et al., "In Situ Electrochemical Oxygen Generation with an Immunoisolation Device," Annals New York Academy of Sciences, vol. 875, 1999, pp. 105-125.
Yamasaki Y., et al., "Direct Measurement of Whole Blood Glucose by a Needle-Type Sensor," Clinica Chimica Acta. 93, 1989, pp. 93-98.
Yamasaki Y., "The Development of a Needle-Type Glucose Sensor for Wearable Artificial Endocrine Pancreas," Medical Journal of Osaka University, vol. 35 (1-2), Sep. 1984, pp. 25-34.
Yang C., et al., "A Comparison of Physical Properties and Fuel Cell Performance of Nafion and Zirconium Phosphate/Nation Composite Membranes," Journal of Membrane Science, vol. 237, 2004, pp. 145-161.
Yang Q., et al., "Development of Needle-Type Glucose Sensor with High Selectivity," Science and Actuators B, vol. 46, 1998, pp. 249-256.
Yang S., et al., "A Glucose Biosensor Based on an Oxygen Electrode: In-Vitro Performances in a Model Buffer Solution and in Blood Plasma," Biomedical Instrumentation & Technology, vol. 30 (1), 1996, pp. 55-61.
Yang S., et al., "Glucose Biosensors with Enzyme Entrapped in Polymer Coating," Biomedical Instrument and Technology, Mar./Apr. 1995, vol. 29 (2), pp. 125-133.
Ye L., et al., "High Current Density Wired Quinoprotein Glucose Dehydrogenase Electrode," Analytical Chemistry, vol. 65, 1993, pp. 238-241.
Zamzow K.L., et al., "Development and Evaluation of a Wearable Blood Glucose Monitor," ASAIO Transactions, vol. 36 (3), 1990, pp. M588-M591.
Zavalkoff S.R., et al., "Evaluation of Conventional Blood Glucose Monitoring as an Indicator of Integrated Glucose Values Using a Continuous Subcutaneous Sensor," Diabetes Care, vol. 25(9), 2002, pp. 1603-1606.
Zethelius B., et al., "Use of Multiple Biomarkers to Improve the Prediction of Death From Cardiovascular Causes," N. Engl. J. Med., vol. 358, May 2008, pp. 2107-2116.
Zhang, et al., "Elimination of the Acetaminophen Interference in an Implantable Glucose Sensor," Analytical Chemistry, 1994, vol. 66 (7), pp. 1183-1188.
Zhang Y., et al., "Electrochemical Oxidation of H2O2 on Pt and Pt + Ir Electrodes in Physiological Buffer and its Applicability to H2O2-Based Biosensors," J. Electro Analytical Chemistry, vol. 345, 1993, pp. 253-271.
Zhang Y., et al., "In Vitro and In Vivo Evaluation of Oxygen Effects on a Glucose Oxidase Based Implantable Glucose Sensor," Analytica Chimica Acta, vol. 281, 1993, pp. 513-520.
Zhu, et al., "Fabrication and Characterization of Glucose Sensors Based on a Microarray H2O2 Electrode," Biosensors & Bioelectronics, 1994, vol. 9, pp. 295-300.
Zhu, et al., "Planar Amperometric Glucose Sensor Based on Glucose Oxidase Immobilized by Chitosan Film on Prussian blue Layer," Sensors, 2002, vol. 2, pp. 127-136.
CIBA Specialty Chemicals, "Ciba® IRGACURE® 2959," Coating Effects Segment, Photoinitiator Product Description, Basel Switzerland, Apr. 2, 1998, 3 pages.
Extended European Search Report for Application No. 09713130.4 dated Apr. 11, 2013, 10 pages.
Shichiri M., et al., "Membrane Design for Extending the Long-Life of an Implantable Glucose Sensor," Diabetes Nutrition & Metabolism, vol. 2 (4), 1989, pp. 309-313.

\* cited by examiner

Define Alerts

- 1110 — Alert ID: Hypo1 ▶
- 1120 — Glucose: Below [70] Above [ ] mg/dL
  - [5] [ ] Rate of change (mg/dL/min.)
- 1130 — Temperature: [ ] [ ] °F
  - [ ] [ ] Δ over 5 minutes
- 1140 — Pulse: [80] [ ] bpm
  - [ ] [15] Δ over 5 minutes 1150 — [Save] [Cancel]

FIG. 11

Alert Data Structure — 1400

| Alert (1410) | Send to (1420) | Device Type (1430) | Frequency (1440) |
|---|---|---|---|
| Near hypoglycemic | joe@msn.com | Mobile | 1 per day |
| Hypoglycemic | joe@msn.com | Mobile | no limit |
| | linda@email.com | MAC | 1 per day |
| | ftp://admin:pass@123.12.12.42 | EMR | 1 per hour |
| | Mobile app: AlertPro, username:joeandlinda | Mobile | no limit |
| | joe@work.com | PC | no limit |
| | device: teachersmobile | Receiver | no limit |
| None | Mobile app: AlertPro, username:joeandlinda | Mobile | up to once per day when in BT range |
| | ftp://admin:pass@123.12.12.42 | EMR | up to once per week |
| | localdevice://joescomputer/sensor data | PC | up to once per day when in BT range |

FIG. 14A

Display Options Data Structure

|  | Mobile | MAC/PC | EMR | Receiver |
|---|---|---|---|---|
| Blood Sugar |  | X |  |  |
| 10 min trend | X | X | X |  |
| 1 hour trend | X | X | X |  |
| 24 hr trend |  |  |  |  |
| Rate of Change |  |  |  |  |
| location |  |  |  |  |

FIG. 14B

Device Data Structure 1500

| Device ID | Device Address | Device Type | Device Model |
|---|---|---|---|
| Joesphone | joe@msn.com | Mobile | BB8830 |
| lindasmac | linda@email.com | MAC | MAC Desktop |
| HospitalEMR | ftp://admin:pass@123.12.12.42 | EMR | Centricity |
| lindasphone | Mobile app: AlertPro, username:joeandlinda | Mobile | iPhone |
| joeatwork | joe@work.com | PC | HP tablet |
| msjones | device: teachersmobile | Receiver | TeacherReceiver |

FIG. 15A

Alert Data Structure

| Alert | Device ID | Frequency | Activate alarm | blood sugar | 10 min trend | 1 hr trend | 24 hr trend | rate of change | location |
|---|---|---|---|---|---|---|---|---|---|
| Near hypoglycemic | mobile1 | 1 per day | | X | | X | | | |
| Hypoglycemic | mobile1 | no limit | | X | | | | | X |
| | lindasmac | 1 per day | | | | X | X | | |
| | HospitalEMR | 1 per hour | | X | X | X | X | X | X |
| | Joesphone | no limit | | X | | X | | | |
| | joeatwork | no limit | | X | | | | | |
| | msjones | no limit | X | | | | | | |
| None | joesphone | up to once per day when in BT range | | | | | X | | |
| | HospitalEMR | up to once per week | | X | X | X | X | X | |
| | joeathome | up to once per day when in BT range | | X | X | X | X | X | |

FIG. 15B

Multi-Sensor Alert Data Structure

| Glucose Level | Pulse | Temperature | Alert | Device ID | Frequency | Activate alarm | blood sugar | 10 min trend | 1 hr trend | 24 hr trend | rate of change | location |
|---|---|---|---|---|---|---|---|---|---|---|---|---|
| 80-90 | >10% increase in < 20 min. | >99 | Near hypoglycemic | mobile1 | 1 per day | | | | | | | |
| <80 | >10% increase in < 20 min. | >100 | Hypoglycemic | mobile1 | no limit | | x | | x | | | |
| | | | | lindasmac | 1 per day | | | | | x | | |
| | | | | HospitalEMR | 1 per hour | | x | x | x | x | x | x |
| | | | | Joesphone | no limit | | x | | | | | x |
| | | | | joeatwork | no limit | | x | | x | | | x |
| | | | | msjones | no limit | x | | | | | | |
| | | | | | up to once per day when in BT range | | | | | | | |
| | | | None | joesphone | up to once | | | | | x | | |
| | | | | HospitalEMR | per week | | x | x | x | x | x | |
| | | | | | up to once per day when in BT range | | | | | | | |
| | | | | joeathome | in BT range | | x | x | x | x | x | |

FIG. 16

SYSTEMS AND METHODS FOR PROCESSING, TRANSMITTING AND DISPLAYING SENSOR DATA

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/673,307, filed Aug. 9, 2017, which is a continuation of U.S. application Ser. No. 12/880,015, filed Sep. 10, 2010, now abandoned, which is a continuation of U.S. application Ser. No. 12/390,304, filed on Feb. 20, 2009, now U.S. Pat. No. 9,143,569, which claims priority under 35 U.S.C. § 119(e) to U.S. Provisional Application No. 61/030,499, filed on Feb. 21, 2008, the disclosures of which are hereby expressly incorporated by reference in their entirety and are hereby expressly made a portion of this application. U.S. application Ser. No. 12/390,304 is related to and incorporates by reference in their entirety the disclosures of commonly owned U.S. application Ser. No. 12/390,205, filed on Feb. 20, 2009, and U.S. application Ser. No. 12/390,290, filed on Feb. 20, 2009.

FIELD OF THE INVENTION

The present invention relates generally to systems and methods for processing, transmitting and displaying data received from an analyte sensor, such as a glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY OF THE INVENTION

In one embodiment, a system for continuous measurement of an analyte in a host comprises a continuous analyte sensor configured to measure a concentration of an analyte in a host, a sensor electronics module physically connected to the continuous analyte sensor during operation of the continuous analyte sensor, wherein the sensor electronics module is configured to process a data stream associated with an analyte concentration measured by the continuous analyte sensor and to generate displayable sensor information based on at least some sensor data of the data stream. In one embodiment, the sensor electronics module comprises a storage device configured to store at least some of the displayable sensor information and a telemetry module configured to wirelessly transmit a first portion of the displayable sensor information to a first display device, wherein the first portion of displayable sensor information is formatted for display on the first display device, and to wirelessly transmit a second portion of the displayable sensor information to a second display device, wherein the second portion of displayable sensor information is formatted for display on the second display device.

In one embodiment, a computerized method for customizing displayable sensor information that is transmitted to display devices comprises determining analyte concentration data associated with a host based at least on sensor data from a continuous analyte sensor associated with the host, generating displayable sensor information based on at least some of the analyte concentration data, storing at least some of the displayable sensor information on a storage device, wirelessly transmitting a first portion of the displayable sensor information to a first display device and wirelessly transmitting a second portion of the displayable sensor information to a second display device. In one embodiment the first portion of displayable sensor information is formatted for display on the first display device and the second portion of displayable sensor information is formatted for display on the second display device.

In one embodiment, a computer readable medium stores software code thereon, the software code configured for execution by one or more processors of a sensor electronics module configured for coupling to an analyte sensor that is attached to a host, wherein the software code, if executed by the one or more processors, causes the sensor electronics module to perform a method comprising determining analyte concentration data associated with a host based at least on sensor data from a continuous analyte sensor associated with the host, generating displayable sensor information based on at least some of the analyte concentration data, storing at least some of the displayable sensor information on a storage device, wirelessly transmitting a first portion of the displayable sensor information to a first display device, and wirelessly transmitting a second portion of the displayable sensor information to a second display device. In one embodiment, the first portion of displayable sensor information is formatted for display on the first display device and the second portion of displayable sensor information is formatted for display on the second display device.

BRIEF DESCRIPTION OF THE DRAWINGS

FIG. 11 illustrates an exemplary user interface for defining alert parameters.

FIG. 14A illustrates a portion of an exemplary alert data structure.

FIG. 14B illustrates a portion of an exemplary delivery options data structure.

FIG. 15A illustrates a portion of an exemplary device data structure.

FIG. 15B illustrates a portion of another exemplary alert data structure.

FIG. 16 illustrates a portion of an exemplary multi-sensor alert data structure.

DETAILED DESCRIPTION OF THE PREFERRED EMBODIMENT

Figure 1:
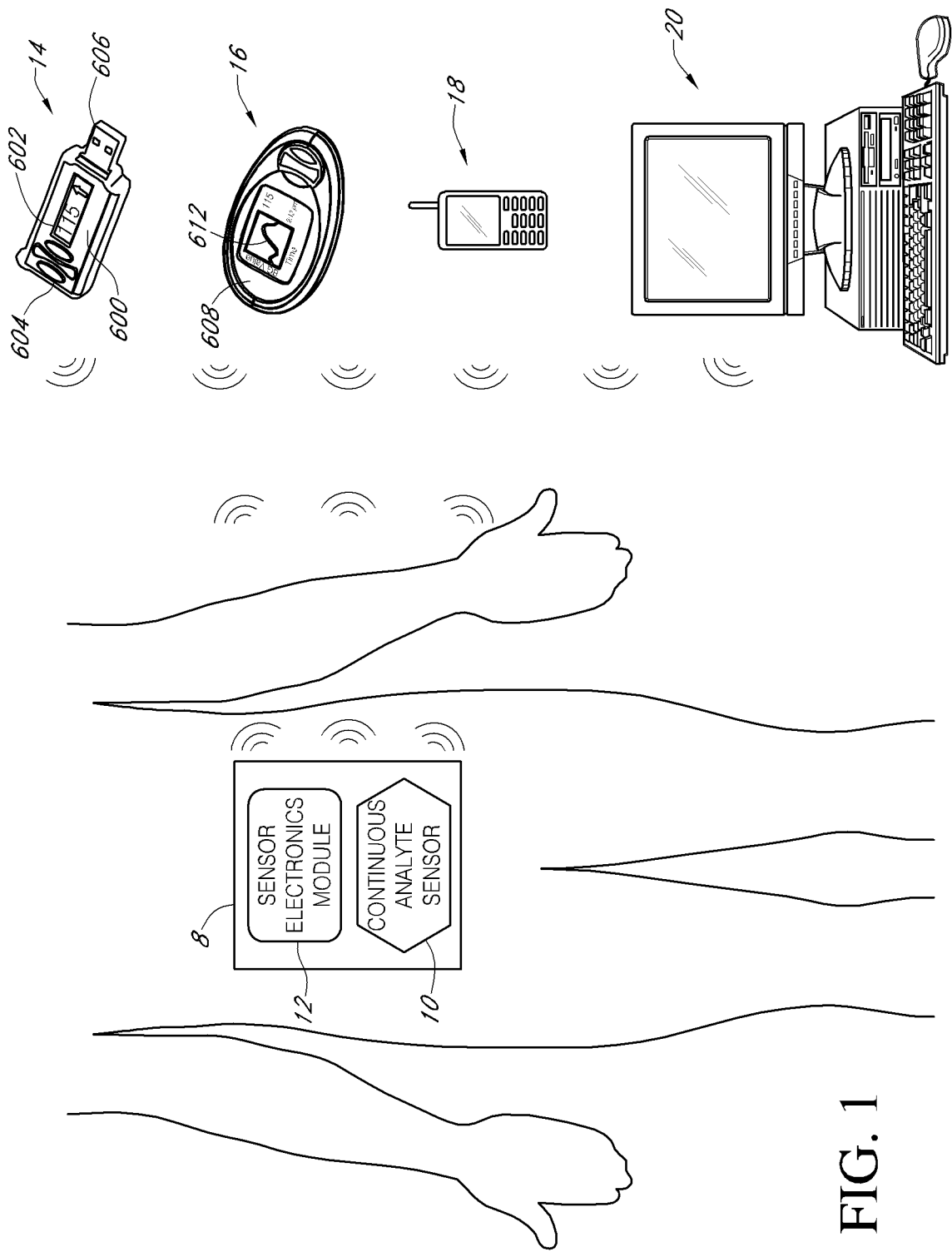
FIG. 1 is a diagram illustrating one embodiment of a continuous analyte sensor system including a sensor electronics module.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-13 hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypo-glycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to generate displayable sensor information that includes raw sensor data, transformed sensor data, and/or any other sensor data, for example. The sensor electronics module may further be configured to generate displayable sensor information that is customized for respective display devices, such that different display devices may receive different displayable sensor information.

Alerts

In one embodiment, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In one embodiment, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. Co-pending U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data packaging indicating an alarm should be initiated by one or a plurality of display devices (e.g., sequentially and/or simultaneously). In some embodiments, the sensor electronics module determines which of the one or more alarms to trigger based on one or more alerts that are triggered. For example, when an alert triggers that indicates severe hypoglycemia, the sensor electronics module can perform multiple actions, such as activating an alarm on the sensor electronics module, transmitting a data package to a small (key fob) indicating activation of an alarm on the display, and transmitting a data package as a text message to a care provider. As an example, a text message can appear on a small (key fob) display, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device, 2) a key fob device, 3) a cell phone (via auditory and/or visual methods, such as, text message to the host and/or care provider, voice message to the host and/or care provider, and/or 911).

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In one embodiment, the sensor electronics module directly wirelessly transmits displayable sensor information to one or a plurality of display devices, such that the displayable sensor information transmitted from the sensor electronics module is received by the display device without intermediate processing of the displayable sensor information.

In one embodiment, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used with the preferred embodiments.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with the preferred embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Small (Key Fob) Display Device

In some embodiments, one the plurality of display devices is a small (e.g., key fob) display device 14 (FIG. 1) that is configured to display at least some of the sensor information, such as an analyte concentration value and a trend arrow. In general, a key fob device is a small hardware device with a built-in authentication mechanism sized to fit on a key chain. However, any small display device 14 can be configured with the functionality as described herein with reference to the key fob device 14, including a wrist band, a hang tag, a belt, a necklace, a pendent, a piece of jewelry, an adhesive patch, a pager, an identification (ID) card, and the like, all of which are included by the phrase "small display device" and/or "key fob device" herein.

In general, the key fob device 14 includes electronics configured to receive and display displayable sensor information (and optionally configured to query the sensor electronics module for the displayable sensor information). In one embodiment, the electronics include a RAM and a program storage memory configured at least to display the sensor data received from the sensor electronics module. In some embodiments, the key fob device 14 includes an alarm configured to warn a host of a triggered alert (e.g., audio, visual and/or vibratory). In some embodiments, the key fob device 14 includes a user interface, such as an LCD 602 and one or more buttons 604 that allows a user to view data, such as a numeric value and/or an arrow, to toggle through one or more screens, to select or define one or more user parameters, to respond to (e.g., silence, snooze, turn off) an alert, and/or the like.

In some embodiments, the key fob display device has a memory (e.g., such as in a gig stick or thumb drive) that stores sensor, drug (e.g., insulin) and other medical information, enabling a memory stick-type function that allows data transfer from the sensor electronics module to another device (e.g., a PC) and/or as a data back-up location for the sensor electronics module memory (e.g., data storage memory). In some embodiments, the key fob display device is configured to be automatically readable by a network system upon entry into a hospital or other medical complex.

In some embodiments, the key fob display device includes a physical connector, such as USB port 606, to enable connection to a port (e.g., USB) on a computer, enabling the key fob to function as a data download device (e.g., from the sensor electronics module to a PC), a telemetry connector (e.g., Bluetooth adapter/connector for a PC), and/or enables configurable settings on the key fob device (e.g., via software on the PC that allows configurable parameters such as numbers, arrows, trend, alarms, font, etc.) In some embodiments, user parameters associated with the small (key fob) display device can be programmed into (and/or modified) by a display device such as a personal computer, personal digital assistant, or the like. In one embodiment, user parameters include contact information, alert/alarms settings (e.g., thresholds, sounds, volume, and/or the like), calibration information, font size, display preferences, defaults (e.g., screens), and/or the like. Alternatively, the small (key fob) display device can be configured for direct programming of user parameters. In some embodiments, wherein the small (key fob) display device comprises a telemetry module, such as Bluetooth, and a USB connector (or the like), such that the small (key fob) display device additionally functions as telemetry adapter (e.g., Bluetooth adapter) enabling direct wireless communication between the sensor electronics module and the PC, for example, wherein the PC does not include the appropriate telemetry adapter therein.

Large (Hand-Held) Display Device

Figure 6:
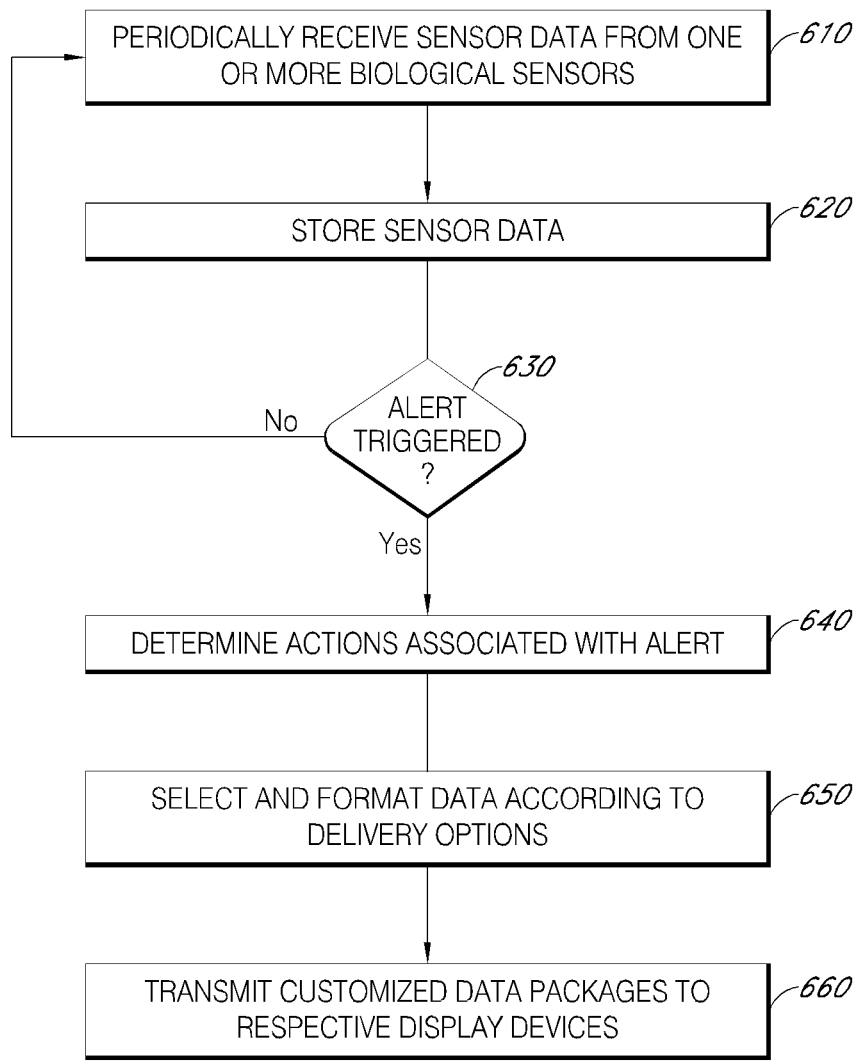
FIG. 6 is a flowchart illustrating one embodiment of a method of generating customizable data packages for delivery to respective display devices, such as based on user-defined delivery options.

In some embodiments, one the plurality of display devices is a hand-held display device 16 (FIG. 1) configured to display sensor information including an analyte concentration and a graphical representation of the analyte concentration over time. In general, the hand-held display device comprises a display 608 sufficiently large to display a graphical representation 612 of the sensor data over a time period, such as a previous 1, 3, 5, 6, 9, 12, 18, or 24-hours of sensor data. In some embodiments, the hand-held device 16 is configured to display a trend graph or other graphical representation, a numeric value, an arrow, and/or to alarm the host. U.S. Patent Publication No. 2005/0203360, which is incorporated herein by reference in its entirety, describes and illustrates some examples of display of data on a hand-held display device. Although FIG. 6 illustrates one embodiment of a hand-held display device, the hand-held device can be any single application device or multi-application device, such as mobile phone, a palm-top computer, a PDA, portable media player (e.g., iPod, MP3 player), a blood glucose meter, an insulin pump, and/or the like.

In some embodiments, a mobile phone (or PDA) is configured to display (as described above) and/or relay sensor information, such as via a voice or text message to the host and/or the host's care provider. In some embodiments, the mobile phone further comprises an alarm configured to warn a host of a triggered alert, such as in response to receiving a data package indicating triggering of the alert. Depending on the embodiment, the data package may include displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, one of the display devices is a drug delivery device, such as an insulin pump and/or insulin pen, configured to display sensor information. In some embodiments, the sensor electronics module is configured to wirelessly communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Patent Publication No. 2005/0192557, which is incorporated herein by reference in its entirety. In some alternative embodiments, the sensor electronic module is configured to wirelessly communicate with a drug delivery device that does not include a display, for example, in order to enable a closed loop and/or semi-closed loop system as described above.

In some embodiments, one of the display devices is a drug delivery device is a reference analyte monitor, such as a blood glucose meter, configured to measure a reference analyte value associated with an analyte concentration in a biological sample from the host.

Personal Computer Display Device

In some embodiments, one of the display devices is personal computer (PC) 20 (FIG. 1) configured to display sensor information. Preferably, the PC 24 has software installed, wherein the software enables display and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module and the PC. In some embodiments, the PC 24 is configured to set and/or modify configurable parameters of the sensor electronics module 12 and/or small (key fob device) 14, as described in more detail elsewhere herein.

Other Display Devices

In some embodiments, one of the display devices is an on-skin display device that is splittable from, releasably attached to, and/or dockable to the sensor housing (mounting unit, sensor pod, or the like). In some embodiments, release of the on-skin display turns the sensor off; in other embodiments, the sensor housing comprises sufficient sensor electronics to maintain sensor operation even when the on-skin display is released from the sensor housing.

In some embodiments, one of the display devices is a secondary device, such as a heart rate monitor, a pedometer, a temperature sensor, a car initialization device (e.g., configured to allow or disallow the car to start and/or drive in response to at least some of the sensor information wirelessly communicated from the sensor electronics module (e.g., glucose value above a predetermined threshold)). In some alternative embodiments, one of the display devices is designed for an alternative function device (e.g., a caller id device), wherein the system is configured to communicate with and/or translate displayable sensor information to a custom protocol of the alternative device such that displayable sensor information can be displayed on the alternative function device (display of caller id device).

Exemplary Configurations

FIG. 1 is a diagram illustrating one embodiment of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14, 16, 18, and/or 20.

In one embodiment, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and preferably a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327. and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety.

Referring again to FIG. 1, a plurality of display devices (14, 16, 18, and/or 20) are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a small (key fob) display device 14, such as a wrist watch, a belt, a necklace, a pendent, a piece of jewelry, an adhesive patch, a pager, a key fob, a plastic card (e.g., credit card), an identification (ID) card, and/or the like, wherein the small display device comprises a relatively small display (e.g., smaller than the large display device) and is configured to display certain types of displayable sensor information (e.g., a numerical value and an arrow, in some embodiments). In some embodiments, one of the plurality of display devices is a large (hand-held) display device 16, such as a hand-held receiver device, a palm-top computer and/or the like, wherein the large display device comprises a relatively larger display (e.g., larger than the small display device) and is configured to display a graphical representation of the continuous sensor data (e.g., including current and historic data). Other display devices can include other hand-held devices, such as a cell phone or PDA 18, an insulin delivery device, a blood glucose meter, and/or a desktop or laptop computer 24.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-

A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Sensor Electronics Module

Figure 2A:
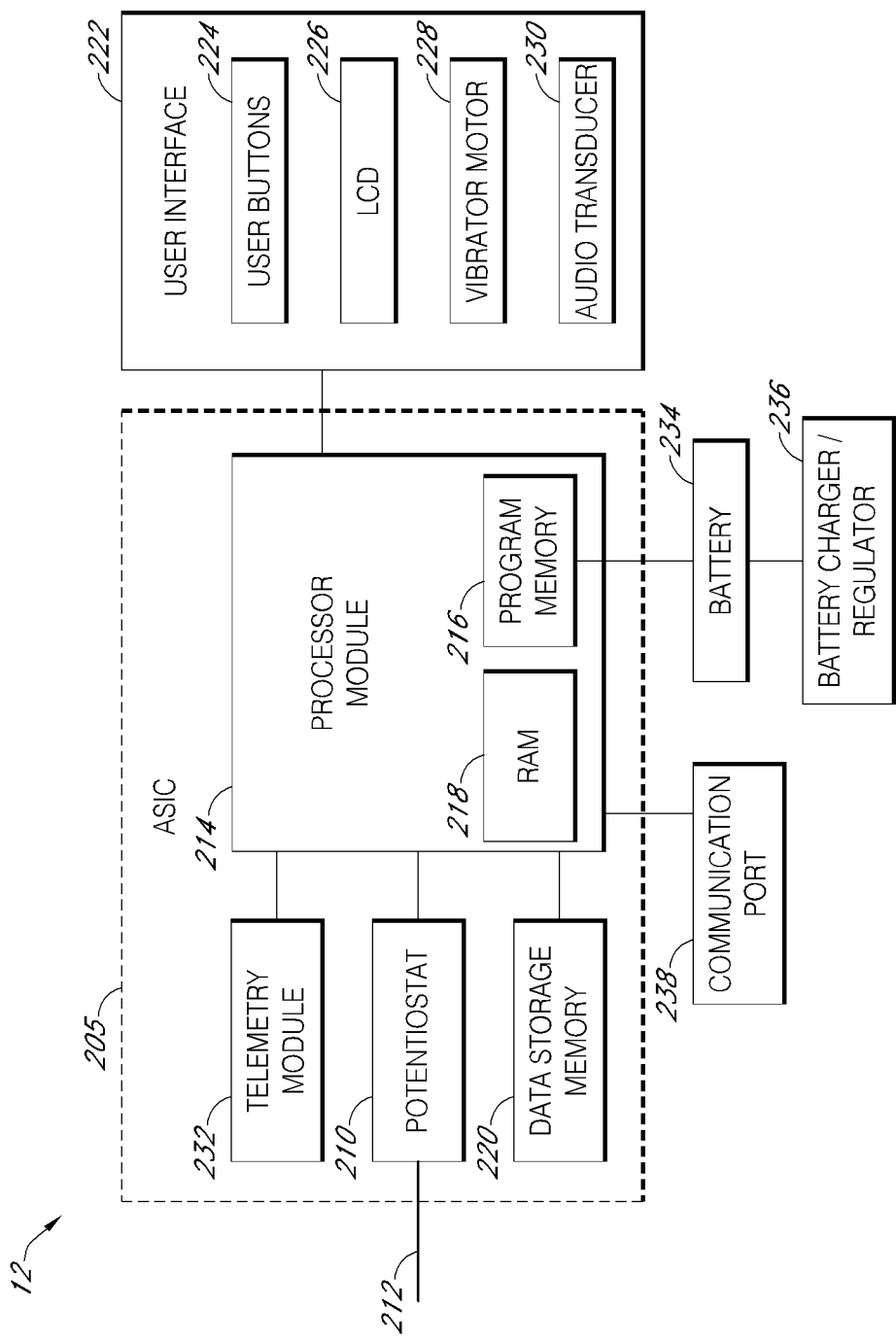
FIG. 2A is a block diagram illustrating one embodiment of the sensor electronics module of FIG. 1.
Figure 2B:
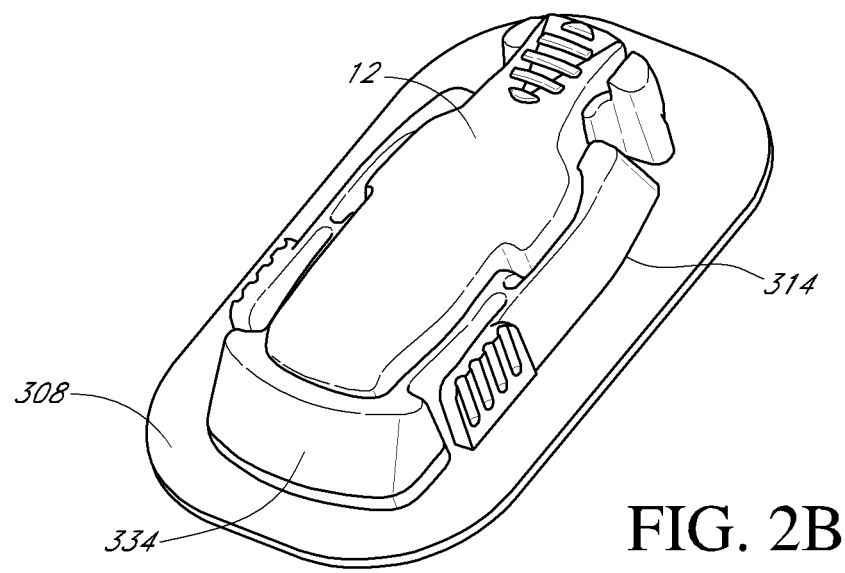
FIG. 2B is a perspective view of a sensor system including a mounting unit and sensor electronics module attached thereto according to one embodiment.
Figure 2C:
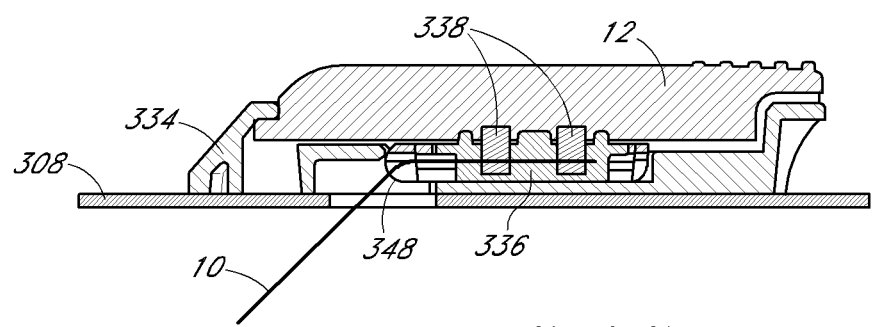
FIG. 2C is a side view of the sensor system of FIG. 2B.

FIG. 2 is a block diagram illustrating one embodiment of the sensor electronics module 12 (FIG. 1). In the embodiment of FIG. 2, the sensor electronics module 12 comprises an application-specific integrated circuit (ASIC) 205 and a user interface 122. In this embodiment, the ASIC 205 is coupled to a communication port 238 and a battery 234. Although the illustrated embodiment shows an Application Specific Integrated Circuit (ASIC) 205 that includes much of the electronic circuitry, the ASIC 205 may be replaced with one or more of any suitable logic device, such as field programmable gate arrays (FPGA), microprocessors, analog circuitry, or other digital and/or analog circuitry.

In this embodiment, a potentiostat 210 is coupled to a glucose sensor via data line 212, for example, in order to receive sensor data from the glucose sensor. In one embodiment, the potentiostat 210 provides a voltage to the glucose sensor via the data line 22 in order to bias the sensor to enable measurement of a current value indicative of the analyte concentration in the host (also referred to as the analog portion). The potentiostat can have one channel or multiple channels (and a corresponding one or multiple data lines 212), depending on the number of working electrodes, for example. In some embodiments, the potentiostat 210 includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 210.

A processor module 214 is the central control unit that controls the processing of the sensor electronics module 12. In some embodiments, the processor module 214 is formed as part of a custom chip, such as an ASIC, however a computer system other than an ASIC can be used to process data as described herein, for example a microprocessor can be used for some or all of the sensor electronics module processing. The processor module 214 typically provides a program memory 216, which provides semi-permanent storage of data, for example, storing data such as sensor identifier (ID) and programming to process data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 218 can be used for the system's cache memory, for example for temporarily storing recent sensor data.

In some embodiments, the processor module 214 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, such as when the potentiostat 210 is configured to measure the analyte at discrete time intervals, these time intervals determine the sample rate of the digital filter. In some alternative embodiments, wherein the potentiostat 210 is configured to continuously measure the analyte, for example, using a current-to-frequency converter, the processor module 214 can be programmed to request a digital value from the integrator at a predetermined time interval, also referred to as the acquisition time. In these alternative embodiments, the values obtained by the processor module 214 are advantageously averaged over the acquisition time due the continuity of the current measurement. Accordingly, the acquisition time determines the sample rate of the digital filter.

In an advantageous embodiment, the processor module 214 may be further configured to generate data packages for transmission to one or more display devices. Furthermore, the processor module 215 may generate data packets for transmission to these outside sources, e.g., via telemetry. As discussed above, the data packages may be customizable for each display device, for example, and may include any available data, such as displayable sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to the processor module 214 and is configured to store a variety of sensor information. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information.

In some embodiments, sensor electronics module 12 is configured to receive and store contact information in the data storage memory (and/or program memory), including a phone number and/or email address for the sensor's host and/or health care providers for the host (e.g., family member(s), nurse(s), doctor(s), or other health care provider(s)), which enables communication with a contact person (e.g., via phone, pager and/or text messaging in response to an alarm (e.g., a hypoglycemic alarm that has not been responded to by the host)). In some embodiments, user parameters can be programmed into (and/or modified in) the data storage memory (and/or program memory) of the sensor electronics module, via a display device such as a personal computer, personal digital assistant, or the like. Preferably, user parameters include contact information, alert/alarms settings (e.g., thresholds, sounds, volume, and/or the like), calibration information, font size, display preferences, defaults (e.g., screens), and/or the like. Alternatively, the sensor electronics module can be configured for direct programming of certain user parameters.

In one embodiment, clinical data of a medical practitioner may be uploaded to the sensor electronics module 12 and stored on the data storage memory 220, for example. Thus, information regarding the host's condition, treatments, medications, etc., may be stored on the sensor electronics module 12 and may be viewable by the host or other authorized user. In one embodiment, certain of the clinical data may be included in a data package that is transmitted to a display device in response to triggering of an alert. The clinical data may be uploaded to the sensor electronics module 12 via any available communication protocol, such as direct transmission via a wireless Bluetooth, infrared, or RF connection, or via a wired USB connection, for example. Additionally, the clinical data may be uploaded to the sensor electronics module 12 via indirect transmission, such as via one or more networks (e.g., local area, personal area, or wide area networks, or the Internet) or via a repeater device that receives the clinical data from a device of the medical practitioner and retransmits the clinical data to the sensor electronics module.

Although separate data storage and program memories are shown in FIG. 1, one skilled in the art appreciates a variety of configurations, including one or multiple memories that provide the necessary storage space to support the sensor electronic module 12 data processing and storage requirements. Accordingly, the described location of storage of any particular information and/or or programming is not meant to be limiting, but rather exemplary.

In some embodiments, the sensor electronics module 12 is configured to perform smoothing and/or filtering algorithms on the sensor data (e.g., raw data stream and/or other sensor information), wherein the smoothed and/or filtered data is stored in the data storage memory as transformed data. Co-pending U.S. Patent Publication Nos. 2005/0043598, 2007/0032706, 2007/0016381 and 2008/0033254 describe some algorithms useful in performing data smoothing and/or filtering herein (including signal artifacts replacement), and are incorporated herein by reference in their entirety.

In some embodiments, the sensor electronics module 12 is configured to calibrate the sensor data, and the data storage memory 220 stores the calibrated sensor data points as transformed sensor data. In some further embodiments, the sensor electronics module 12 is configured to wirelessly receive calibration information from a display device, from which the sensor electronics module is configured to calibrate the sensor data. U.S. Pat. Nos. 7,310,544 and 6,931,327 describe some algorithms useful in sensor calibration herein, and are incorporated herein by reference in their entirety.

In some embodiments, the sensor electronics module 12 is configured to perform additional algorithmic processing on the sensor data (e.g., calibrated and/or filtered data and/or other sensor information) and the data storage memory 220 is configured to store the transformed sensor data and/or sensor diagnostic information associated with the algorithms. U.S. Pat. Nos. 7,310,544 and 6,931,327 describe some algorithms that can be processed by the sensor electronics module, and are incorporated herein by reference in their entirety.

Referring again to FIG. 5, a user interface 222 can include a variety of interfaces, such as one or more buttons 224, a liquid crystal display (LCD) 226, a vibrator 228, an audio transducer (e.g., speaker) 230, backlight, and/or the like. A backlight can be provided, for example, to aid the user in reading the LCD in low light conditions. The components that comprise the user interface 222 provide controls to interact with the user (e.g., the host). One or more buttons 224 can allow, for example, toggle, menu selection, option selection, status selection, yes/no response to on-screen questions, a "turn off" function (e.g., for an alarm), a "snooze" function (e.g., for an alarm), a reset, and/or the like. The LCD 226 can be provided, for example, to provide the user with visual data output. The audio transducer 230 (e.g., speaker) provides audible signals in response to triggering of certain alerts, such as present and/or predicted hyper- and hypoglycemic conditions. In some embodiments, audible signals are differentiated by tone, volume, duty cycle, pattern, duration, and/or the like. In some embodiments, the audible signal is configured to be silenced (e.g., snoozed or turned off) by pressing one or more buttons 224 on the sensor electronics module and/or by signaling the sensor electronics module using a button or selection on a display device (e.g., key fob, cell phone, and/or the like).

In some embodiments, the audio transducer 230 is mounted to the circuit board and/or the sensor electronics module housing. In some embodiments, the sound produced by the audio transducer 230 exits the device from a sound port in the sensor electronics module 12, such as a hole on the sensor electronics module body 12. Preferably, the hole is waterproofed and/or otherwise protected from moisture by a waterproof material that easily allows sound waves there through. In one preferred embodiment, the hole is protected from moisture by an acoustically transparent venting material (wherein the material allows at least about 60%, 70%, 80%, 90%, 95%, or more of the transmitted sound waves there through), such as a screw-in vent, a press-fit vent, a snap-in vent, an o-ring vent, and adhesive vent, and/or the like. One manufacturer that provides acoustically transparent venting material is W. L. Gore & Associates (Elkton, Md.) under the trade name Protective Vents (Acoustic Vents).

The vibrator 228 can include a motor that provides, for example, tactile signals or alerts for reasons such as described with reference to the audio transducer, above. In one embodiment, the vibrator motor 228 provides a signal in response to triggering of one or more alerts, which can be triggered by the processor module 214 that processes algorithms useful in determining whether alert conditions associated with one or more alerts have been met, for example, present and/or predicted hyper- and hypoglycemic conditions. In some embodiments, one or more different alerts are differentiated by intensity, quantity, pattern, duration, and/or the like. In some embodiments, the alarm is configured to be silenced (e.g., snoozed or turned off) by pressing one or more buttons 224 on the sensor electronics module 12 and/or by signaling the sensor electronics module 12 using a button or selection on a display device (e.g., key fob, cell phone, and/or the like).

In some embodiments, the vibrator motor 228 is mounted to the circuit board and/or the sensor electronics module 12 housing. Preferably the diameter of the motor is less than or equal to about 6 mm, 5 mm, 4 mm, 3.5 mm, 3 mm, 2.5 mm, 2 mm or less. Preferably the overall length of the vibrator motor is less than or equal to about 18 mm, 16 mm, 14 mm, 12 mm, 10 mm or less. By providing a low power vibrator motor, the motor can be place in the sensor electronics module 12 without significantly affecting the low profile nature of the on-skin sensor electronics module 12.

In some embodiments, the vibrator motor 228 may be used to provide a vibratory alarm that creates vibration and/or movement of the sensor within the host. While not wishing to be bound by theory, it is believed that a concentration increase of noise-causing electroactive species, such as electroactive metabolites from cellular metabolism and wound healing, can interfere with sensor function and cause noise observed during host start-up and/or sedentary periods. For example, local lymph pooling, which can occur when a part of the body is compressed or when the body is inactive, can cause, in part, this local build up of interferants (e.g., electroactive metabolites). Similarly, a local accumulation of wound healing metabolic products (e.g., at the site of sensor insertion) likely causes noise on the sensor during the first few hours to days after sensor insertion. Accordingly, it is believed vibration and/or movement of the sensor at the insertion site, after sensor insertion, can reduce or eliminate pooling of local interfering species caused by the wound healing process described above. In some embodiments, the sensor is vibrated and/or moved at predetermined intervals and/or in response to noise artifacts detected on the sensor signal. Co-pending U.S. Patent Application No. 2005/0043598, 2007/0032706, 2007/0016381 or 2008/0033254 describe systems and methods for detection of noise artifacts, noise episodes and/or classification of noise, which can be useful with the embodiments described herein.

Although audio and vibratory alarms are exemplified in FIG. 5, alternative alarming mechanisms can be used in some embodiments. For example, in one alternative embodiment, a tactile alarm is provided including a poking mechanism (not shown) configured to "poke" the patient in response to one or more alarm conditions.

In another alternative embodiment, the sensor electronics module 12 is configured to transmit sound waves into the host's body (e.g., abdomen or other body part) that will be felt by the host, thereby allowing the host to be alerted without calling attention to himself and/or thereby allowing a hearing-impaired visually-impaired, and/or tactilely-impaired host to be alerted. In some embodiments, the sound waves can be transmitted into the host's body using the electrodes of the sensor itself. In some embodiments, one or more transcutaneous electrodes (other than the electrodes related to analyte measurement) are provided for transmitting sound waves. In some embodiments, electrodes can be provided in the adhesive patch that holds the sensor/sensor electronics module onto the host's body, which can be used to transmit the sound waves. In some embodiments, different sound waves are used to transmit different alarm conditions to the host. The sound waves could be differentiated by any sound characteristic, such as but not limited to amplitude, frequency and pattern.

In another alternative embodiment, mild electric shock could be used to transmit one or more alarms to the host. Preferably the level of shock would not be overly uncomfortable to the host; however, the intensity of the level of shock can be configured to increase when a host does not respond to (e.g., snooze or turn off) an alert within an amount of time. In some embodiments, the shock can be delivered to the host's body using the electrodes of the sensor itself. In some embodiments, the sensor system can include one or more additional electrodes configured for delivering the shock to the host (alone or in combination with the electrodes related to analyte measurement). In still another example, the one or more electrodes can be disposed on the host's skin, such as in the adhesive patch, for delivering the shock. Alternatively, one or more additional patches, each including an electrode, can be provided, for delivering the shock. The additional patches can be in wired and/or wireless communication with the sensor electronics module.

A telemetry module 232 is operably connected to the processor module 214 and provides the hardware, firmware, and/or software that enable wireless communication between the sensor electronics module 12 and one or more display devices. A variety of wireless communication technologies that can be implemented in the telemetry module 232 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, and/or the like. In one preferred embodiment, the telemetry module comprises a Bluetooth chip. In some embodiments, Bluetooth technology is implemented in a combination of the telemetry module 232 and the processor module 214.

A battery 234 is operatively connected to the processor module 214 (and possibly other components of the sensor electronics module 12) and provides the necessary power for the sensor electronics module 12. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example.

A battery charger and/or regulator 236 may be configured to receive energy from an internal and/or external charger. In one embodiment, a battery regulator (or balancer) 236 regulates the recharging process by bleeding off excess charge current to allow all cells or batteries in the sensor electronics module to be fully charged without overcharging other cells or batteries. In some embodiments, the battery 234 (or batteries) is configured to be charged via an inductive and/or wireless charging pad. One skilled in the art appreciates a variety of known methods of charging batteries, which can be implemented with the system described herein, including wired (cable/plug) and wireless methods.

One or more communication ports 238, also referred to as external connector(s), can be provided to allow communication with other devices, for example a PC communication (com) port can be provided to enable communication with systems that are separate from, or integral with, the sensor electronics module. The communication port, for example, may comprise a serial (e.g., universal serial bus or "USB") communication port, allows for communicating with another computer system (e.g., PC, personal digital assistant or "PDA," server, or the like). In one exemplary embodiment, the sensor electronics module 12 is able to transmit historical data to a PC or other computing device for retrospective analysis by a patient and/or physician.

In conventional continuous analyte sensor systems, the on-skin portion of the sensor electronics is generally simplified to minimize complexity and/or size of on-skin electronics, for example, providing only raw, calibrated, and/or filtered data to a secondary display device configured to run calibration and other algorithms required for displaying the sensor data. In contrast, the sensor electronics module 12 executes prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like, which are described in more detail in U.S. Pat. Nos. 7,310,544 and 6,931,327, and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety. Furthermore, the sensor electronics module 12 is configured to store the transformed sensor data (e.g., values, trend information) and to communicate the displayable sensor information to a plurality of different display devices. In some embodiments, the display devices are "dummy" devices, namely, they are configured to display the displayable sensor information as received from the sensor electronics module 12, without any additional sensor data processing.

Exemplary System Configurations

Figure 3:
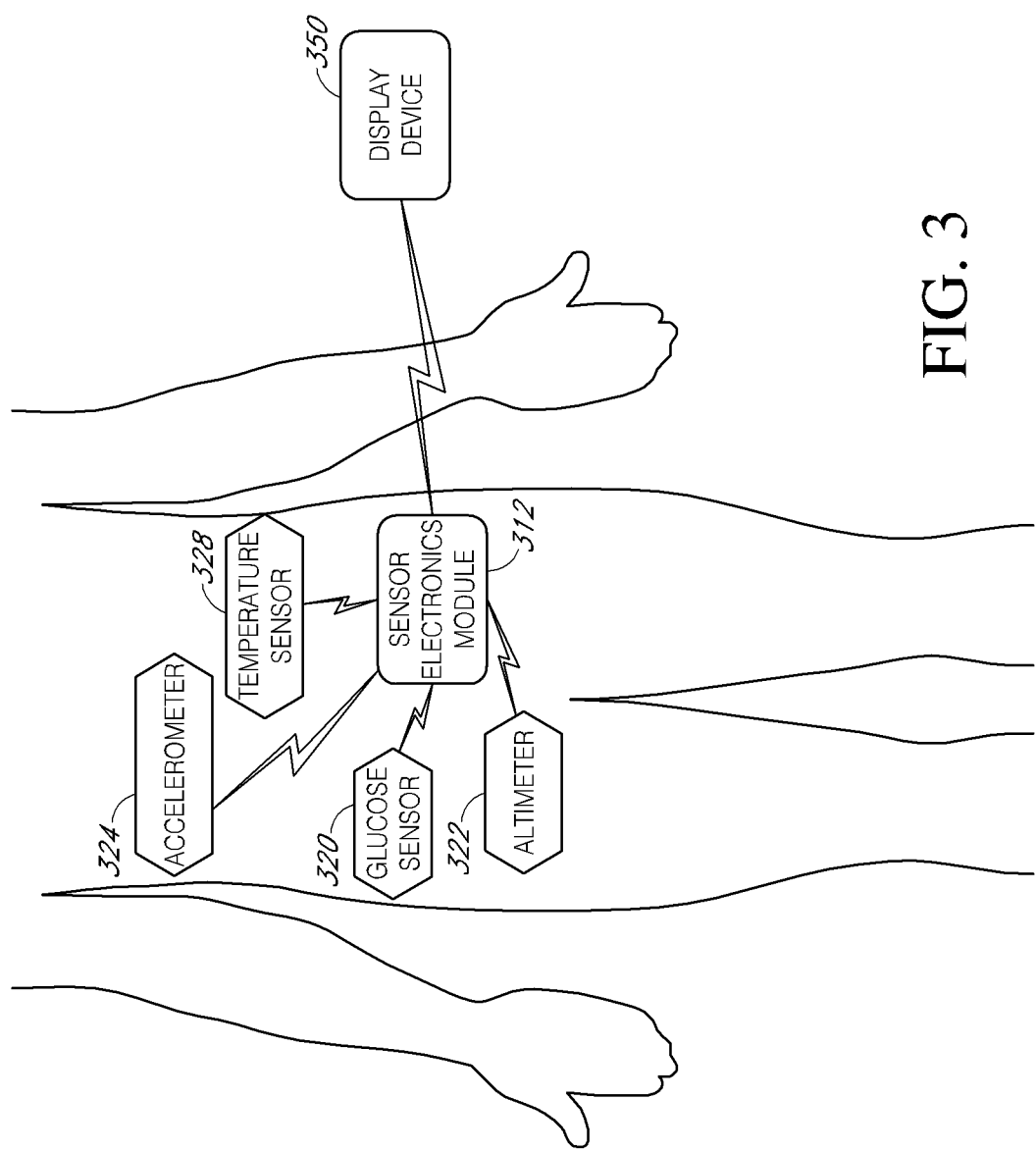
FIG. 3 is a diagram illustrating one embodiment of a sensor electronics module in communication with multiple sensors, including a glucose sensor.

FIG. 3A is a diagram illustrating one embodiment of a sensor electronics module 312 in communication with multiple sensors, including a glucose sensor 320, an altimeter 322, an accelerometer 324, and a temperature sensor 328. In this embodiment, each of the sensors 320-328 communicates sensor data wirelessly to the sensor electronics module 312. In other embodiments, the sensor electronics module 312 comprises one or more of the sensors 320-328. In other embodiments, the sensors are combined in any other configuration, such as a combined glucose/temperature sensor that transmits sensor data to the sensor electronics module 312 using common communication circuitry. Depending on the embodiment, fewer or additional sensors may communicate with the sensor electronics module 312. In other embodiments, one or more of the sensors 320-328 is directly coupled to the sensor electronics module 312, such as via one or more electrical communication wires.

In the embodiment of FIG. 3A, the sensor electronics module 312 generates and transmits a data package to display device 350, which may be any electronic device that is configured to receive, store, retransmit, and/or display displayable sensor data. Advantageously, the sensor electronics module 312 analyzes the sensor data from the multiple sensors and determines which displayable sensor data is to be transmitted to the particular display device 350, based on one or more of many characteristics of the host, the display device 350, a user of the display device 350, and characteristics of the sensor data and/or the transformed sensor data. Thus, the customized displayable sensor information that is transmitted to the display device 350 may be displayed on the display device with minimal processing by the display device 350.

FIGS. 3B and 3C are perspective and side views of a sensor system including a mounting unit 314 and sensor electronics module 12 attached thereto in one embodiment, shown in its functional position, including a mounting unit and a sensor electronics module matingly engaged therein. In some preferred embodiments, the mounting unit 314, also referred to as a housing or sensor pod, comprises a base 334 adapted for fastening to a host's skin. The base can be formed from a variety of hard or soft materials, and preferably comprises a low profile for minimizing protrusion of the device from the host during use. In some embodiments, the base 334 is formed at least partially from a flexible material, which is believed to provide numerous advantages over conventional transcutaneous sensors, which, unfortunately, can suffer from motion-related artifacts associated with the host's movement when the host is using the device. Preferably, the mounting unit 314 and/or sensor electronics module 12 is/are located over the sensor insertion site to protect the site and/or provide a minimal footprint (utilization of surface area of the host's skin).

In some embodiments, a detachable connection between the mounting unit 314 and sensor electronics module 12 is provided, which enables improved manufacturability, namely, the relatively inexpensive mounting unit 314 can be disposed of when replacing the sensor system after its usable life, while the relatively more expensive sensor electronics module 12 can be reusable with multiple sensor systems. In some preferred embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 338 are mounted on or in a subassembly hereinafter referred to as a contact subassembly 336 configured to fit within the base 334 of the mounting unit 314 and a hinge 348 that allows the contact subassembly 336 to pivot between a first position (for insertion) and a second position (for use) relative to the mounting unit 314. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In preferred embodiments, the contacts 338 are formed from a conductive elastomeric material, such as a carbon black elastomer, through which the sensor 10 extends.

In certain embodiments, the mounting unit 314 is provided with an adhesive pad 308, preferably disposed on the mounting unit's back surface and preferably including a releasable backing layer. Thus, removing the backing layer and pressing the base portion 334 of the mounting unit onto the host's skin adheres the mounting unit 314 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 3B and 3C are described in more detail with reference to U.S. Pat. No. 7,310,544, which is incorporated herein by reference in its entirety. Preferably, configurations and arrangements that provide water resistant, waterproof, and/or hermetically sealed properties are provided associated with the mounting unit/sensor electronics module embodiments described herein.

Figure 4:
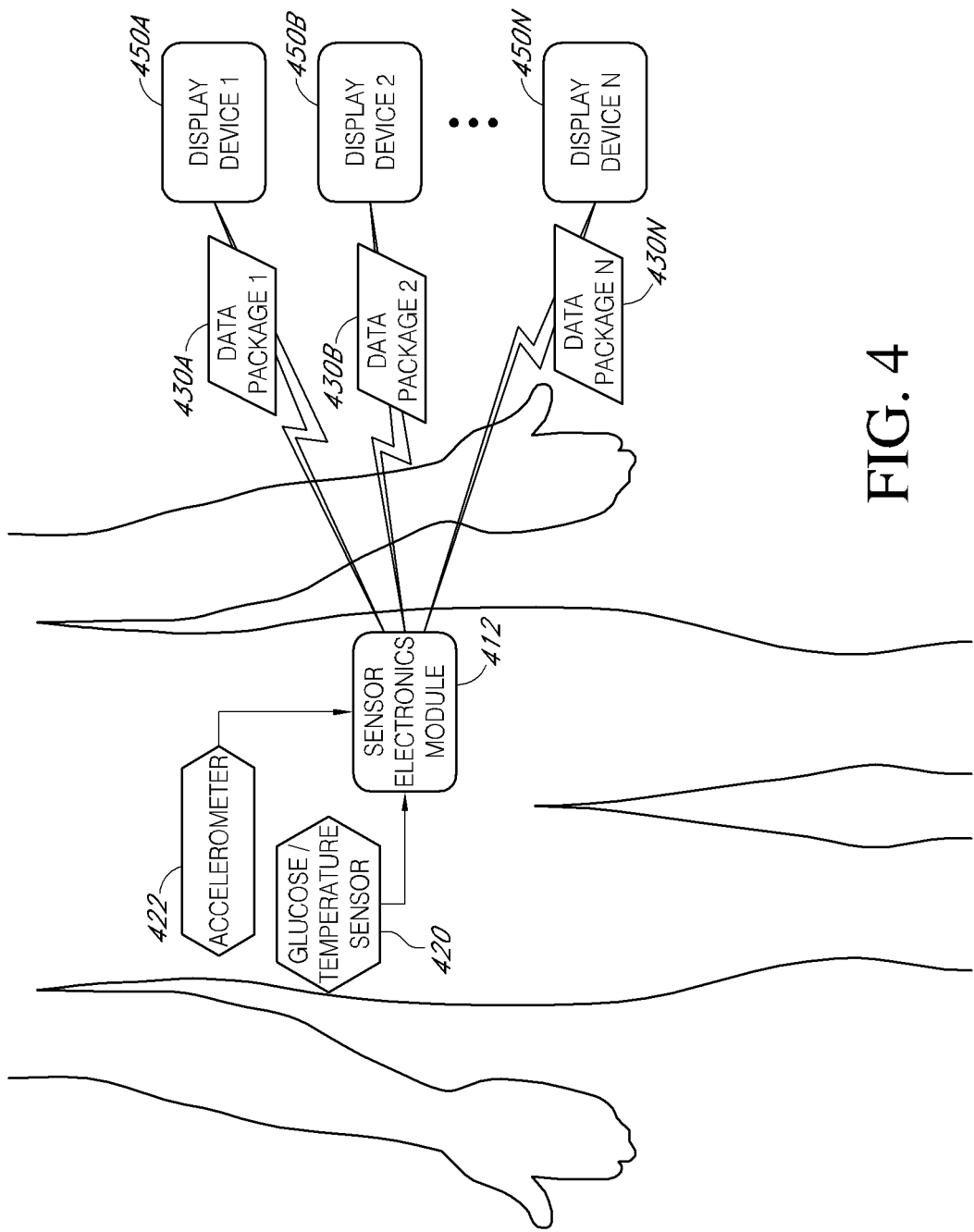
FIG. 4 is a diagram illustrating one embodiment of a sensor electronics module in communication with a combined glucose and temperature sensor, as well as an accelerometer.

FIG. 4 is a diagram illustrating one embodiment of a sensor electronics module 412 in communication with a combined glucose and temperature sensor 420, as well as an accelerometer 422. In the embodiment of FIG. 4, the glucose and temperature sensor 420 senses both a glucose level of the host and a temperature of the host, such as a skin temperature and/or a subcutaneous temperature of the host. In the embodiment of FIG. 4, the glucose and temperature sensor 420 are coupled to the sensor electronics module 412 via a physical connection, such as one or more electrical lines. In one embodiment, a housing attached to the glucose and temperature sensor 420 attaches directly to the sensor electronics module 412. In the embodiment of FIG. 4, an accelerometer 422 is also in wireless communication with the sensor electronics module 412, such as radio frequency, Bluetooth, or ANT communications, for example.

The sensor electronics module 412 is configured to generate and transmit customized data packages to each of a plurality of display devices, including display devices 450A, 450B and 450N. As discussed further below, the timing, content, and formatting of displayable sensor information that is included in respective data packages may be based on one or more of a plurality of factors. For example, one or more alerts may be established based on default alert conditions or custom alert conditions that are designated by the device manufacturer, the host, or a guardian of the host. An alert is said to be "triggered" when the alert conditions associated with the alert are met by the sensor data and/or transformed sensor data. For example, a near hypoglycemic alert may include an alert condition that requires that the host's current glucose level is below 80 mg/dL. Thus, the particular near hypoglycemic alert would be triggered when the host's current glucose level is below 80 mg/dL, and, in response to triggering of the alert, any actions associated with the particular alert are initiated. In one embodiment, actions associated with an alert may include generation of displayable sensor information, transmission of a data package to one or more display devices, activating one or more alarms (e.g., auditory or vibratory), communicating data to another device, or any other action. For example an action that transmits a customized data package to each of a plurality of display devices may be associated with a near hypoglycemic alert. Thus, when the alert conditions for the near hypoglycemic alert are triggered, the actions initiate compilation and transmission of the indicated data packages to the respective display devices. In one embodiment, the content and formatting of each data package may be customized, such that displayable sensor information included in the respective data packages may include quite different displayable sensor information.

In the embodiment of FIG. 4, a first data package 430A is transmitted to a first display device 450A, while a second data package 430B is transmitted to a second display device 450B and a third data package 430N is transmitted to a third display device 450N. In this embodiment, each data package 430A, 430B, 430C may be customized for the respective receiving display devices. For example, the first data package 430A may include only an indication of a current glucose level of the host, while the second data package 430B may include historical sensor data as well as one or more trend indicators associated with the host's glucose levels. Additionally, the formatting of the displayable sensor data may be customized for each receiving display device. For example, each of display devices 450B and 450N may receive a 20 minute trend indicator in response to triggering a near hypoglycemic alert; however, the formatting of the 20 minute trend indicators that are transmitted to the display devices 450B and 450N may be quite different. Thus, the sensor electronics module 412 allows extensive customization of the timing, content, and delivery parameters for delivering data packages to respective display devices.

Figure 5A:
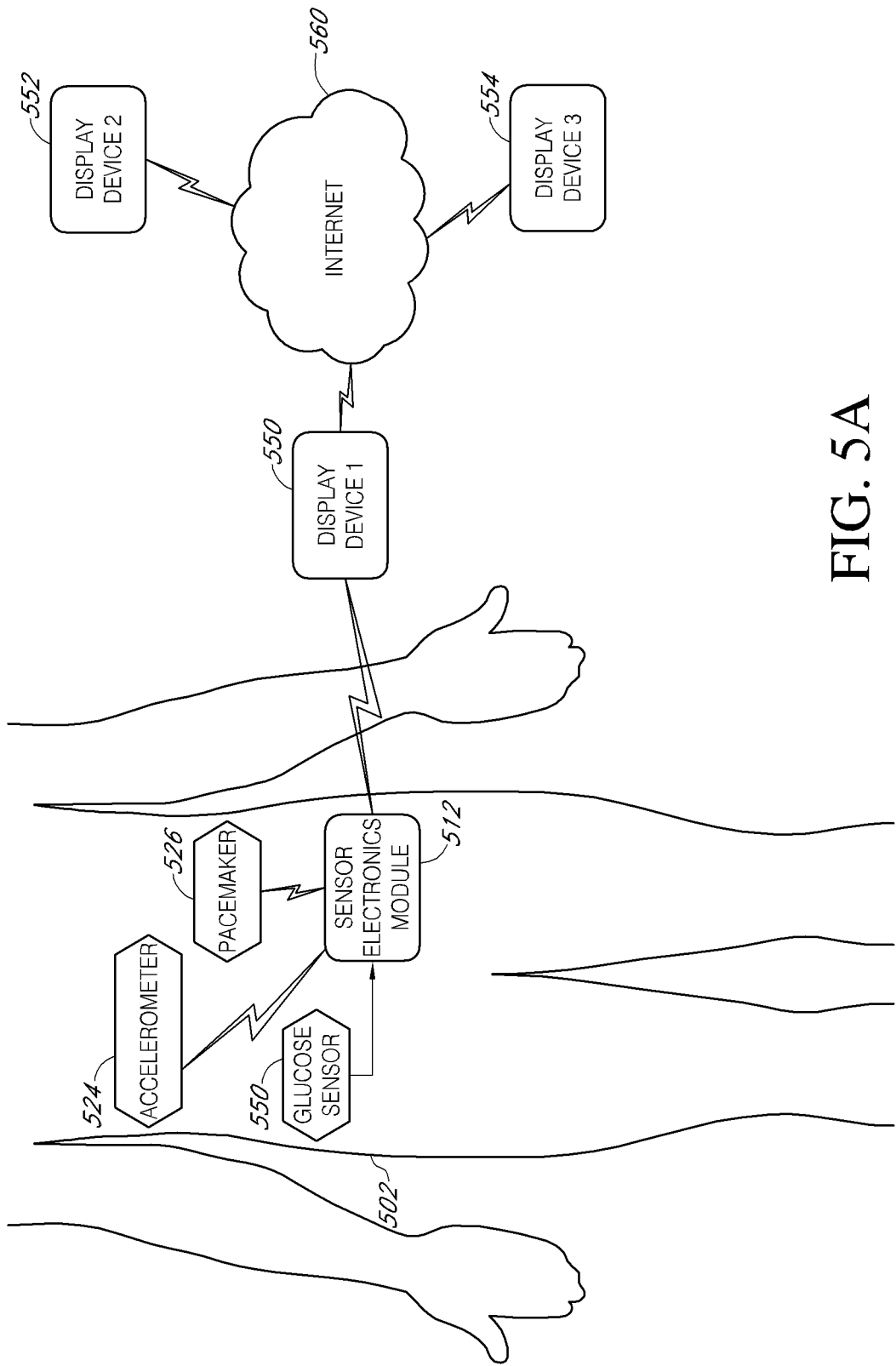
FIG. 5A is a diagram illustrating one embodiment of a sensor electronics module directly transmitting data to a first display device and indirectly transmitting data to second and third display devices.

FIG. 5A is a diagram illustrating one embodiment of a sensor electronics module 512 directly transmitting data to a first display device 550 and indirectly transmitting sensor data to second and third display devices 552, 554 via the Internet 560 and the display device 550. In the embodiment of FIG. 5A, the sensor electronics module 512 comprises a telemetry module that is configured to communicate with the first display device 550, which in turn, is configured to communicate with multiple other display devices via the Internet 560. For example, the sensor electronics module 512 may include a Bluetooth transmitter that transmits data packages, such as in response to triggering of an alert, to the first display device 550, such as a mobile phone. In this example, the mobile phone may also include wireless Internet capabilities, such as might be provided by Wi-Fi or WiMax circuitry, such that the mobile phone can communicate with other devices in communication with the Internet 560. Accordingly, the sensor electronics module 512 may transmit data packages to a nearby display device 550, along with an indication that the display device 550 should transmit the data package (or a portion of the displayable sensor information in the data package) to one or more other display devices (such as display devices that are not in close proximity to the sensor electronics module 512), via the Internet 560. In this embodiment, displayable sensor information is transmitted to remote display devices through the use of an intermediate display device 550. In other embodiments, the sensor electronics module 512 is configured to transmit data packages according to two or more communication protocols, such as Bluetooth and Wi-Fi. In that embodiment, the sensor electronics module 512 may communicate with the display device 550 via Bluetooth and may communicate with the display devices 552, 554 via the Internet 560 (without the need for the data to be retransmitted by the display device 550), for example.

In the embodiment of FIG. 5A, a pacemaker 526 is in communication with the glucose sensor 550. In this embodiment, the pacemaker 526 may transmit data to the glucose sensor 550 and/or may receive data, such as control signals, from the glucose sensor 550. In this embodiment, the glucose sensor 550 functions as a repeater, transferring control signals from the sensor electronics module 512 to the pacemaker 526, such as in response to triggering of an alert based on sensor data from one or more of the glucose sensor 550, the accelerometer 524, and/or the pacemaker 526. In one embodiment, control signals transmitted to the pacemaker 526 may indicate changes in operation of the pacemaker 526, such as increasing or decreasing a frequency of stimulation applied by the pacemaker 526. In another embodiment, the pacemaker 526, or other devices such as an insulin pump or a brain scintillator, may be coupled directly to the sensor electronics module 512, via a wired and/or wireless communication path. Accordingly, the sensor electronics module 512 may receive sensor data from multiple sensors, process the sensor data in order to generate transformed sensor data, determine if any alert conditions have been satisfied by the sensor data and/or the transformed sensor data, and perform actions associated with any triggered alerts, including transmission of control signals to other devices, such as the pacemaker 526, and transmission of customized data packages to one or more display devices.

Figure 5B:
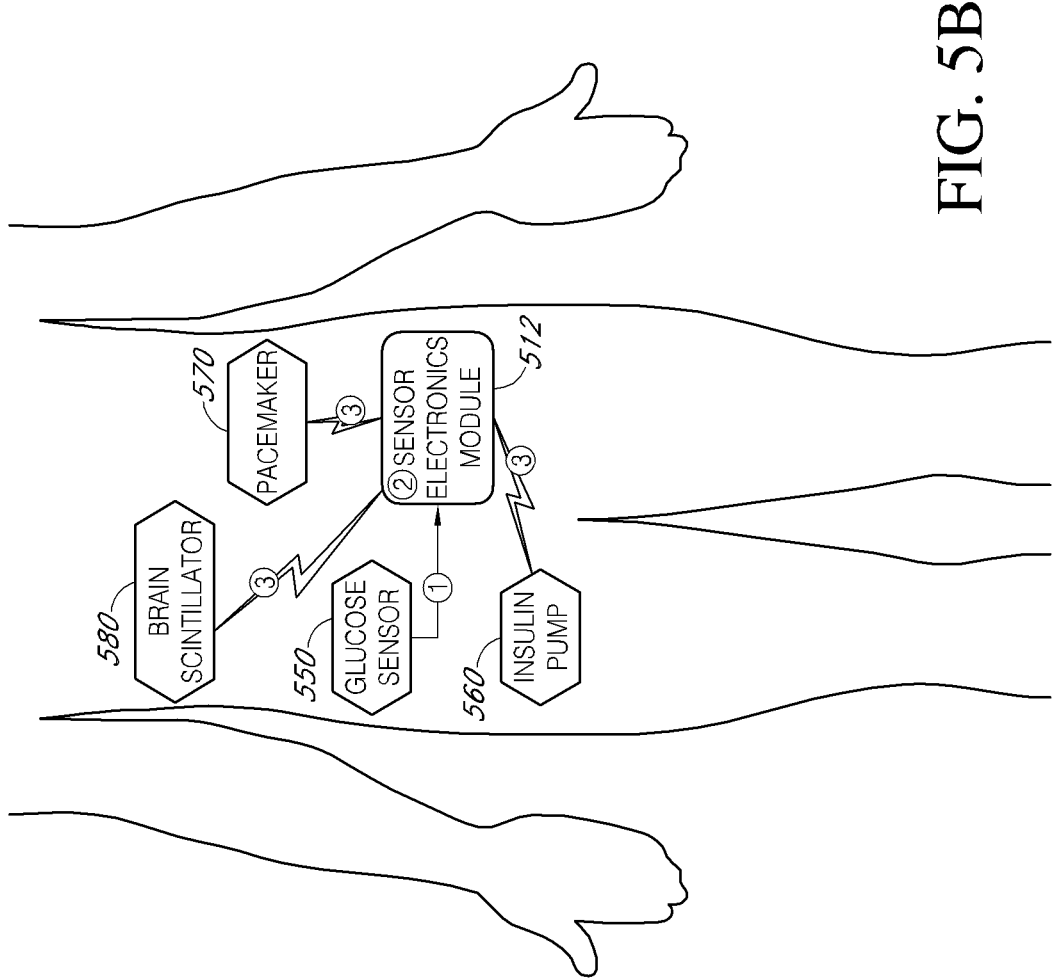
FIG. 5B is a diagram illustrating one embodiment of the sensor electronics module configured to transmit control signals to biological devices coupled to the host.

FIG. 5B is a diagram illustrating one embodiment of the sensor electronics module 512 configured to transmit control signals to biological devices coupled to the host. In the embodiment of FIG. 5B, the sensor electronics module 512 receives sensor data from a glucose sensor 550, and possibly other sensors, and transmits control signals to one or more of the insulin pump 560, the pacemaker 570, and/or the brain scintillator 580. Other biological devices that provide medicines and/or stimulations to the host may also be in communication with the sensor electronics module 512. In the embodiment of FIG. 5B, an exemplary temporal flow of data is indicated by the circled numerals. In step one of the exemplary process (indicated by the circled "1" in FIG. 5B), the glucose sensor provides raw sensor data to the sensor electronics module 512, such as on a periodic or intermittent basis. In step two, the sensor electronics module 512 processes the sensor data, generates any transformed sensor data that is required to determine if any alerts have triggered, and determines if any alerts have triggered based on the received sensor data and/or transformed sensor data. In this embodiment, one possible action associated with a triggered alert is to transmit control signals to one or more other biological devices, such as the insulin pump 560, the brain scintillator 580, and/or the pacemaker 570 (e.g., step 3 of FIG. 5B). For example, a hyperglycemic alert may be associated with an action of transmitting a control signal to the insulin pump 560 indicating that insulin should be pumped to the host, and possibly details of a dosage and/or time for providing the insulin to the host. Similarly, a low heart rate alert, such as based on data received from a heart rate sensor (not shown) may include an action of transmitting a control signal to the pacemaker 570 indicating that the pacemaker should adjust a timing and/or algorithm at which impulses are administered to the host. Accordingly, a sensor electronics module 512 may receive sensor data from one or more sensors, process the sensor data in order to determine if any alerts are triggered, and perform actions associated with triggered alerts that cause control signals to be transmitted to respective biological devices, such as those illustrated in FIG. 5B.

In the embodiment of FIG. 5B, biological devices 560, 570, 580 are each in communication with the sensor electronics module 512 via a wireless communication link, such as radio frequency, Bluetooth, or ANT communications. In other embodiments, one or more of these biological devices may be directly physically coupled to the sensor electronics module, such as via one or more data lines. In another embodiment, one or more of the biological devices may be integral to a sensor, such as glucose sensor 550, such that control signals from the sensor electronics module 512 may be transmitted to a integrated sensor/biological device. In yet another embodiment, the sensor electronics module transmits indications of control signals to an external device, such as a display device, which then relays the appropriate control signal to the corresponding biological device. For example, the sensor electronics module 512 may transmit an indication of a control signal to a cellular phone of the host, for example, with an indication that the control signal should be transmitted to a particular biological device, such as the brain scintillator 580. In one embodiment, the communication protocol used by the sensor electronics module 512 in communicating with the cellular telephone is different than a communication protocol used by the cellular telephone in communicating with the brain scintillator 580. Accordingly, the sensor electronics module 512 may communicate with a wider range of biological devices through the use of another device, such as a display device, that receives the control signal indications via a first communication protocol (e.g., Bluetooth) and transmits corresponding control signals to the appropriate biological devices via a second communication protocol (e.g., Radio Frequency), which the sensor electronics module may not be configured to use.

Figure 5C:
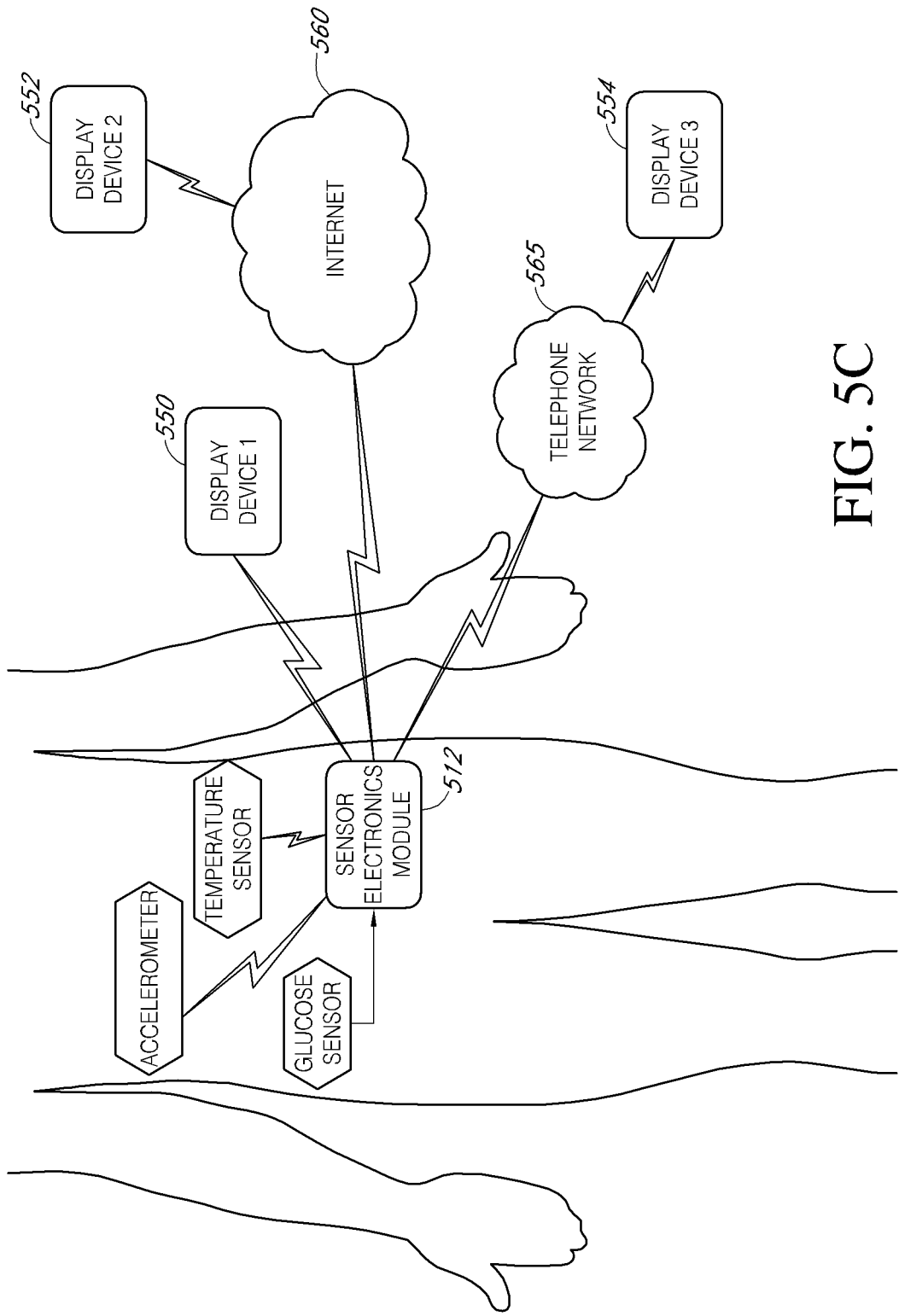
FIG. 5C is a diagram illustrating one embodiment of the sensor electronics module in communication with multiple sensors, wherein the sensor electronics module transmits data packages to multiple display devices via multiple networks, such as the Internet and a telephone network.

FIG. 5C is a diagram illustrating one embodiment of the sensor electronics module 512 in communication with multiple sensors, wherein the sensor electronics module 512 transmits data packages to multiple display devices via multiple networks, such as the Internet 560 and a telephone network 565. In the embodiment of FIG. 5C, the sensor electronics module 512 is in communication with the Internet 560 as well as a telephone network 565, which may comprise one or more cellular networks, digital or analog wireless telephone networks, or plain old telephone service (POTS) networks. Thus, in the embodiment of FIG. 5C, the sensor electronics module 512 may transmit short message service (SMS) messages, for example, to the display device 554. Additionally, the sensor electronics module 512 may transmit other types of messages, such as voice messages, paging signals, or other data packages, via the telephone network 565. In this embodiment, the sensor electronics module 512 is also configured to transmit data packages to the other display devices 550, 552 via the Internet 560.

FIG. 6 is a flowchart illustrating one embodiment of a method of generating customizable data packages for delivery to respective display devices, such as based on user-defined delivery options. As noted above, the sensor electronics modules discussed herein advantageously allow customization of displayable sensor information, such as combinations of sensor data and/or transformed sensor data, for transmission to respective display devices. Depending on the embodiment, the method of FIG. 6 may include viewer or additional blocks in the blocks may breed performed in a different order than is illustrated.

Beginning in block 610, the sensor electronics module intermittently receives and/or processes sensor data from one or more sensors, such as a glucose sensor, accelerometer, altimeter, or any other sensor. Each of the sensors that transmit sensor data to the sensor electronics module may have a predetermined or dynamic schedule for transmitting sensor data. For example, a first sensor may transmit sensor data to the sensor electronics module on a consistent periodic basis, such as one sensor data point per minute, 5 minutes, 10 minutes, 30 minutes etc., while a second sensor may transmit sensor data to the sensor electronics module only when the sensor data reaches a certain threshold. For example, an altimeter may only transmit sensor data to the sensor electronics module 512 when an altitude of the altimeter is above a predetermined threshold.

Moving to block 620, the sensor data received from the one or more sensors is stored, such as in one or more memories and/or storage devices of the sensor electronics module. With reference to the embodiment of FIG. 2, the sensor data may be stored in the data storage memory 220 and/or the random access memory 218.

Next, in block 630 the sensor electronics module determines if one or more alerts have been triggered. As noted above, each alert is associated alert conditions that must be met in order for the respective alert to trigger. The alert conditions could be any characteristic of the sensor data, transformed sensor data, a display device, a host, or an operator of a display device, along with other characteristics. For example, two different alerts that are each related to the host reaching a hypoglycemic glucose level may have slightly different alert conditions that must be satisfied in order to trigger the alerts. For example, a first hypoglycemic alert may require that the host's glucose level is below a first threshold and that a temperature of the host is above a certain threshold, while a second hypoglycemic alert may only require that the host's glucose level is below a second threshold (which may be slightly lower than the first threshold). In this embodiment, the first and second hypoglycemic alerts may be associated with actions that are quite different, such as transmission of data packages of various content and formatting to different display devices.

If the sensor electronics module determines that an alert has triggered in block 630, the method continues to block 640 where one or more actions associated with the triggered alert are initiated. For an action that includes transmission of one or more data packages to a respective one or more display devices, each of the data packages may be associated with one or more delivery options indicating the content (e.g., which displayable sensor information, such as sensor data and/or transformed sensor data, should be included in the data package) and/or formatting requirements for the indicated displayable sensor information, such as whether the displayable sensor information should be in a textual or graphical format. Other actions might include alarms that are associated with the sensor electronics module or a display device, such as activation of a vibrator motor or audio transducer, for example.

In block 650, the sensor electronics module determines the delivery options associated with the actions of the triggered alert and generates the appropriate displayable sensor information in response to the delivery options. In one embodiment, the sensor electronics module performs algorithmic operations on the sensor data in order to generate transformed sensor data, such as trending data, which is stored in the sensor electronics module for later access. In other embodiments, the sensor electronics module executes algorithms on the sensor data in response to triggering of an alert, such that the transformed sensor data included in the data package is generated after the alert is triggered. Alternatively, the sensor electronics module may generate some transformed sensor data as the sensor data is received and may also generate additional transformed sensor data in response to triggering of an alert. In one embodiment, the displayable sensor information is selected according to parameters of the alert action, and the displayable sensor information is combined into one or more data packages for transmission to the display device indicated in the action.

Next, in block 660, the generated data package is transmitted to display device indicated in the alert action. If more than one action is associated with a triggered alert, multiple data packages may be generated and transmitted to respective display devices. Accordingly, the sensor electronics module allows customization of alert notifications including various levels of detail that are desired by the host or other interested parties.

Figure 7:
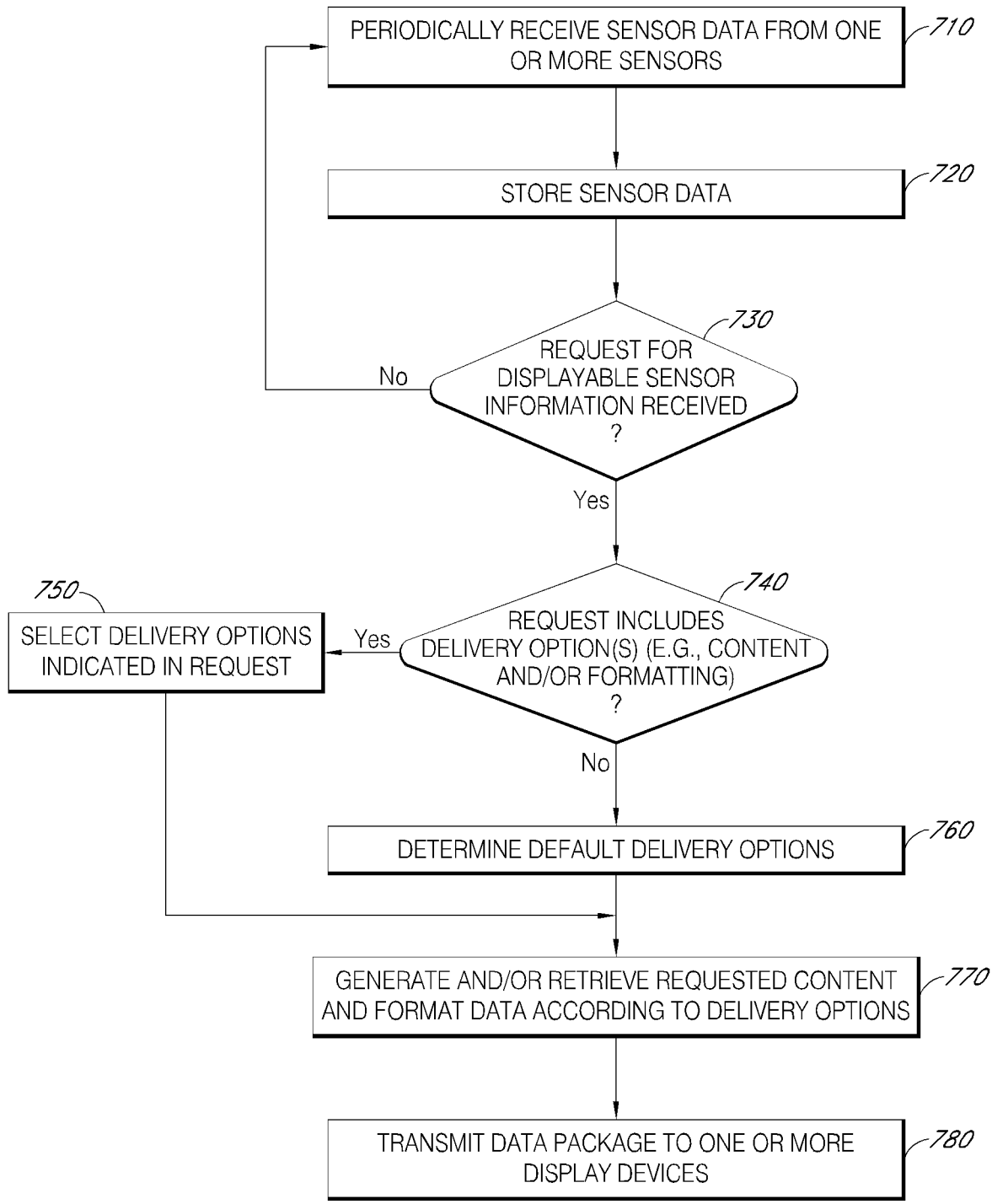
FIG. 7 is a flowchart illustrating one embodiment of a method of generating customizable data packages for delivery to requesting display devices, such as in response to receiving a request from a display device.

FIG. 7 is a flowchart illustrating one embodiment of a method of generating customizable data packages for delivery to requesting display devices, such as in response to receiving a request for certain sensor information from a display device. In one embodiment, a display device may request sensor information from the sensor electronics module, rather than waiting to receive a data package from the sensor electronics module in response to triggering of an alert. For example, a display device, such as a mobile telephone, may be configured to request certain displayable sensor information up to once a day whenever the mobile device is within Bluetooth range of the sensor electronics module. Thus, the mobile telephone may receive displayable sensor information even when alerts having actions for delivery of displayable sensor information to the mobile telephone are not triggered. Depending on embodiment, the method of FIG. 7 may include fewer or additional blocks and blocks may be performed in a different order than is illustrated.

Beginning in block 710, the sensor electronics module periodically receives sensor data from one or more sensors. As noted above, the sensor electronics module may be configured to receive data from any type of sensor via any suitable wired and/or wireless communication protocols.

Next, in block 720, the received sensor data is stored. Depending on embodiment, sensor data may be stored for predetermined time periods and/or predetermined quantities. For example, data from one sensor may be removed from the sensor electronics module after it is more than 30 days old, while data from another sensor may remain in the sensor electronics module until storage space on the sensor electronics module reaches a certain threshold.

Continuing to block 730, the sensor electronics module determines if a request for displayable sensor information has been received from a display device. If no request for displayable sensor information has been received, the method returns to block 710 where sensor data from the one or more sensors continues to be received. If, however, a request for displayable sensor information has been received from a display device, or from another device, the method continues to block 740.

In block 740, the sensor electronics module determines if the request for displayable sensor information includes custom delivery options for the displayable sensor information. For example, the delivery options may include indications of particular sensor data and/or transformed sensor data that are to be included in the displayable sensor information, as well as possibly formatting instructions for the displayable sensor information.

If the request does include delivery options, the delivery options are selected in block 750. If, however, the request does not include delivered options, the method continues to block 760, where default delivery options are selected. In one embodiment, the default delivery options comprise a standard set of displayable sensor information with formatting options that are compatible with many/most display devices. In another embodiment, default delivery options may be specific to one or more attributes of the requesting display device, such as a type, make, or model of the display device. In other embodiments, the default delivery options may be based on other attributes, such as a time of day at which the request is received, a status of the requesting display device, or a transmission protocol by which the data package will be transmitted to the requesting display device, for example. In other embodiments, default delivery options may be determined based on any other relevant factors.

In block 770, the sensor electronics module generates and/or retrieves the requested content, such as sensor data and/or transformed sensor data, and formats the data according to the selected default and/or custom delivery options. If delivery options were received in the request, displayable sensor information is selected and formatted according to the receive delivered options. Alternatively, if no delivery options were received in the request, displayable sensor information is selected and formatted according to one or more default delivery options.

In block 780, the displayable sensor information is packaged into one or more data packages and transmitted to the requesting display device. In one embodiment, a requesting display device may indicate a different recipient of the requested displayable sensor information. For example, a first display device, e.g., a mobile telephone, may send a request for displayable sensor information to a sensor electronics module indicating that the requested displayable sensor information be transmitted to a notebook computer rather than, or in addition to, transmitting the requested displayable sensor information to the requesting mobile telephone. In one embodiment, the request may include multiple sets of delivery options associated with multiple recipients of displayable sensor information.

Figure 8:
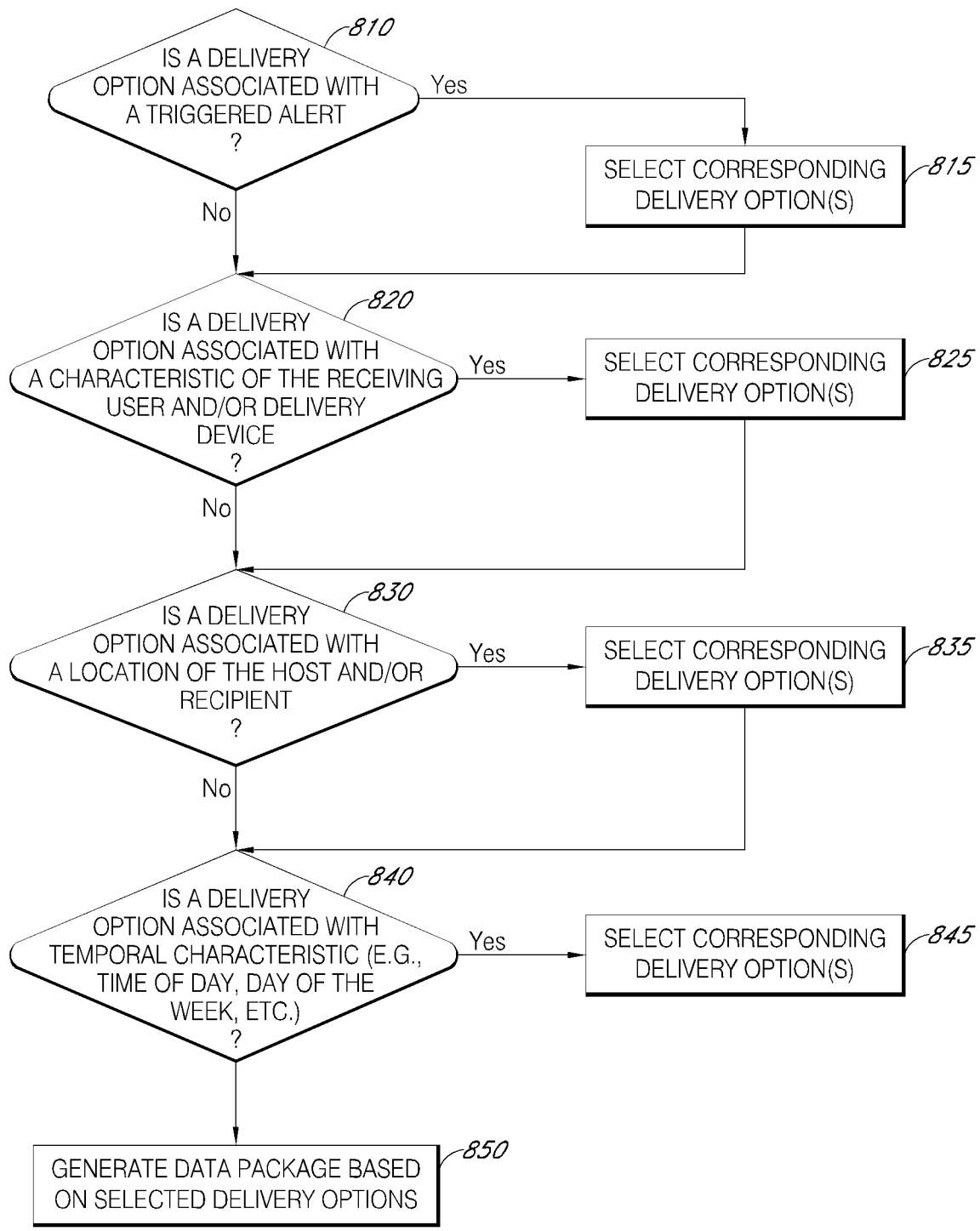
FIG. 8 is a flowchart illustrating what embodiment of a method of selecting delivery options for a data package based on one or more of a plurality of attributes.

FIG. 8 is a flowchart illustrating one embodiment of a method of selecting delivery options for a data package based on one or more of a plurality of attributes. As noted above, delivery options may be associated with one or more of a plurality of attributes associated with a triggered alert, a host, a time of day/week/month, a location of a host, a recipient display device, a display device characteristic (e.g., a type, model, and/or make of display device), and/or any other relevant characteristics. Thus, delivery options, such as what sensor data and transformed sensor data should be included in the displayable sensor information, and how the displayable sensor information should be formatted for delivery, may be based on multiple characteristics.

The method of FIG. 8 illustrates selection of delivery options associated with a few exemplary characteristics. The method of FIG. 8 may be performed, for example as part of an alert action that is initiated in response to triggering of an alert. Thus, in one embodiment the method of FIG. 8 describes an exemplary method of selecting delivery options for transmission of a data package to a particular delivery device in response to triggering of an alert. In other embodiments, delivery options may be selected based on any other characteristic. The relationship of delivery options to the characteristics discussed below, as well as other characteristics, may be stored in any suitable data structure, such as a database, a flat file, a spreadsheet, a text document, or any other file structure. Depending on the embodiment, the method of FIG. 8 may include fewer or additional blocks and blocks may be performed in a different order than is illustrated.

Beginning in block 810, the sensor electronics module determines if a delivery option is associated with a triggered alert. If a delivery option is associated with a triggered alert, the method continues to block 815 wherein the appropriate delivery options are selected. In certain embodiments, depending on the alert, certain sensor data and/or transformed sensor data may be important to transmit to the corresponding delivery device. For example, key information associated with a first alert may include a series of sensor data points from a glucose monitor, while key information associated with a second alert may include transformed data indicating a 60 minute trend in the glucose level of the host. Thus, each alert may be associated with different displayable sensor information and/or options for formatting the displayable sensor information.

Continuing to block 820, the sensor electronics module determines if a delivery option is associated with the delivery device and/or one or more users of the delivery device. For sample, if an alert action indicates that a data package should be transmitted to an electronic medical records (EMR) system, a sensor electronics module may select certain displayable sensor information for delivery to the EMR. Similarly, if an alert action indicates that a data package should be transmitted to a cell phone, a sensor electronics module may select different (e.g. a much smaller subset) displayable sensor information for delivery to the cell phone. Additionally, the formatting of the displayable sensor information for delivery to an EMR and a cell phone, for example, may be customized by the sensor electronics module based on the type of display device.

In certain embodiments, the sensor electronics module may determine respective users of receiving displayed devices and customize the displayable sensor information transmitted to the respective display devices accordingly. For example, a mother of a diabetic child that wears a sensor electronics module may always be interested in knowing the location of her child when alerts are transmitted to her. Accordingly, if the sensor electronics module determines that the mother is the user of a receiving display device, whether the display device is a cell phone, a notebook computer, or desktop computer, for example, the sensor electronics module may include the child's location in the displayable sensor information that is included in the corresponding data package. If delivery options are associated with the receiving delivery device and/or the user of the delivery device, the method continues to block 825 where the corresponding delivery options are selected.

Moving to block 830, the sensor electronics module determines if a delivery option is associated with a location of the host and/or the delivery device. In one embodiment, the sensor electronics module includes a global positioning system (GPS) sensor that determines an approximate or precise location of the sensor electronics module. In other embodiments, the sensor electronics module may include other circuitry that determines a location of the sensor electronics module, such as using cell phone communication signals, for example. In one embodiment, the delivery options for a data package may be modified based on the current location of the associated host. For example, if the host is at home, the delivery options may indicate that a minimal set of displayable sensor information is included in the transmitted data package. However, if the host is at an unknown location, the delivery options may indicate that a more comprehensive set of displayable sensor information is included in the transmitted data package. If delivery options are associated with the location of the patient and/or recipient, the method continues to block 835 where those delivery options are selected.

Continuing to block 840, the sensor electronics module determines if a delivery option is associated with a temporal characteristics, such as a time of day or day of the week, for example. Thus, the delivery options may be adjusted based on the time at which the alert is triggered. For example, if a near hypoglycemic alert is triggered at 7 a.m. and the host typically eats breakfast at about 7:30 a.m., the delivery options may indicate only a minimal set of displayable sensor information for transmission to a display device of the host. However, if the near hypoglycemic alert is triggered at 10 p.m., a more complete set of displayable sensor information may be selected for transmission to the display device of the host. Similarly, a display device, either of the host or another interested party, may receive data packages with displayable sensor information that is customized based on the day of the week on which the corresponding alert was triggered. For example, the content of displayable sensor information may vary depending on whether the alert is triggered on a weekday or a weekend. If delivery options are associated with the one or more temporal characteristics the method continues to block 845 where those temporal characteristics are selected.

Next, in block 850 the sensor electronics module generates a data package according to the selected delivery options (e.g., in blocks 815, 825, 835, 845) and initiates transmission of the data package to the delivery device indicated in the delivery action. Accordingly, the data package comprises displayable sensor information that is customized based on one or more of multiple parameters, including those parameters discussed with respect to FIG. 8, elsewhere in this specification, and any other relevant parameters.

In other embodiments, certain delivery options may be included as alert conditions of respective alerts. Thus, if a delivery option is included as an alert condition (e.g., do not deliver data packages during a certain time period), the alert would not trigger unless the alert condition is satisfied.

Figure 9:
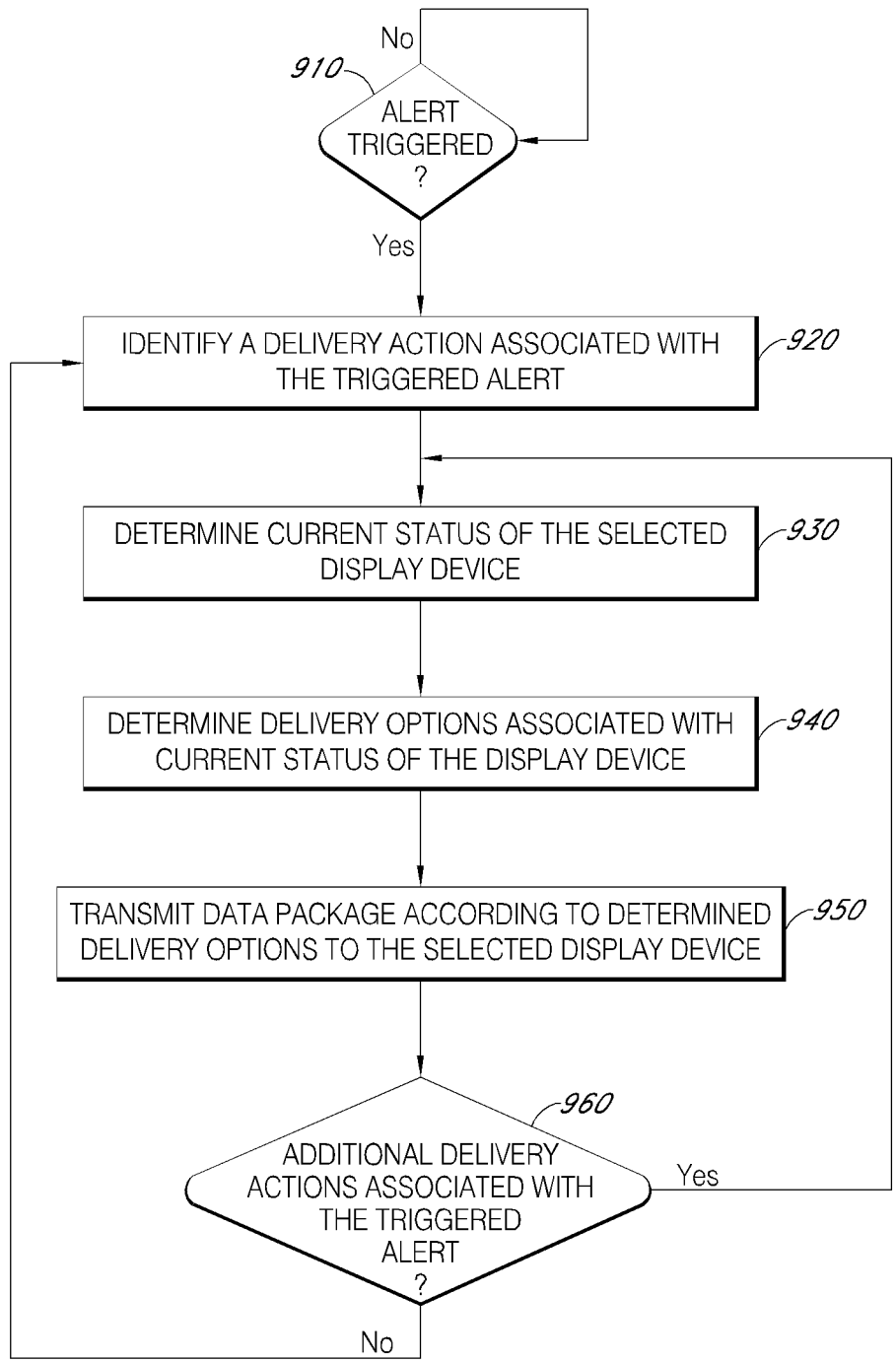
FIG. 9 is a flowchart illustrating one embodiment of a method of generating and transmitting a data package that is customized according to a status of the host and/or a status of the receiving display device.

FIG. 9 is a flowchart illustrating one embodiment of a method of generating and transmitting a data package that is customized according to a status of the host and/or a status of the receiving display device. For example, statuses may include one or more of resting, exercise, do not disturb, illness, menstruation, mealtime, snooze, day, night, hyperglycemia, hypoglycemia, clinical risk, noise, and the like. In one embodiment, different statuses of the host indicate to the sensor electronics changes in how sensor data should be analyzed, such as how transformed sensor data is determined. Depending on the embodiment, statuses of the host may be automatically detected by the sensor electronics module, other sensors or devices associated with the host, and/or display device of the host. For example, an accelerometer that communicates with the sensor electronics module may provide data that is indicative of running motion, such that the sensor electronics module determines that a status of the host is "exercise" or the like. Statuses may also be determined from other sensor data, such as transformed sensor data, from a glucose sensor, for example. Additionally, statuses of the host and/or display devices (or the user of the display device) may be changed according to a status schedule, such as a schedule indicating that the host should be in sleep mode from 10 pm to 7 am each night and that a particular display device is in do not disturb mode from 1 pm to 4 pm Monday through Friday. In other embodiments, the status of a host may be provided by the host (or caretaker of the host) via a user interface of the sensor electronics module or a display device. For example, a display device of the host may include an interface that allows the host to select from a group of statuses, such as by scrolling through a list of status indicators (graphical and/or textual). Any other suitable user interface may also be used for selecting statuses and/or creating new statuses. In one embodiment, a timer may be associated with a status change such that after an indicated time period the status of the host returns to a default status. For example, a host may change their status to "exercise" when entering a gym for a one hour training session and may associate a 60 minute (or slightly longer) timer with the status so that their status is returned to a default status automatically after the workout is complete.

In one embodiment, the status of the host may affect alert conditions associated with one or more alerts, such that certain sensor data and/or certain transformed sensor data might trigger an alert when the host is in a first status, but would not trigger an alert when the host is in a second status. For example, when a person is exercising, his/her glucose levels may increase or decrease in trends that would be abnormal under any other circumstances; by setting the appropriate status, the sensor electronics module is configured to modify its processing associated with the user in a particular status, e.g., "exercise status" to trigger alerts, analyte estimates, trend information, therapy recommendations, and the like, customized with one or more criteria associated with exercise. Additional disclosure of statuses that are associated with a host of a glucose sensor are discussed in commonly own U.S. patent application Ser. No. 12/258,345, entitled "systems and methods for processes sensory data," filed on Oct. 24, 2008, which is hereby incorporated by reference in its entirety.

In one embodiment, a user (e.g., the host to which the sensor electronics module is coupled) may enter events in real time (or retrospectively) in a display device and the events may be transmitted to the sensor electronics module. In one embodiment, the events are useful when the historical sensor data and/or transformed sensor data is later analyzed. Events may be entered to indicate when a particular action was taken by the host, such as when carbohydrates were consumed, when insulin was taken, when exercise was performed, when any relevant change in the health of the host occurs, and/or any other event that might possible effect the sensor data. These events may include more detailed information regarding the respective event, such as an indication of an insulin dosage associated with an insulin event or an indication of a particular type of exercise performed and a total exercise time that are associated with an exercise event. The events could then be represented textually and/or pictorially in the displayable sensor information that is transmitted to display devices. Accordingly, triggering of an alert that would otherwise raise great concern may not be as worrisome when events surrounding the alert trigger are viewable by the user of the display device.

In some embodiments, the event data may be used to modify when alerts are triggered and/or when/how data packages are transmitted to respective display devices. For example, entry of an event may cause adjustments to algorithms that are used in real-time generation of transformed sensor data. Thus, similar to the use of statuses discussed above, the events associated with the host may be used in the real-time determination of alert triggers and delivery of displayable sensor information, as well as being useful in later analysis of sensor information associated with the host.

In the method of FIG. 9, statuses are associated with display devices so that the delivery options for transmitting a data package to a display device may be modified according to a current status of the receiving display device. Depending on embodiment, the method of FIG. 9 may include fewer or additional blocks and the blocks may be performed in a different order that is illustrated.

Beginning in block 910, the sensor electronics module determines if an alert is triggered. As discussed above, alerts may be triggered based on raw sensor data, transformed sensor data (e.g., calibrated and/or filtered data), or any other data from one or more sensors.

Next, in block 920, the sensor electronics module identifies a delivery action associated with a triggered alert. As discussed above, a delivery action is a specific type of action wherein a data package comprising displayable sensor information is generated and transmitted to an indicated display device. Thus, with identification of a delivery action, a corresponding display device is also identified in block 920.

Continuing to block 930, the sensor electronics module determines a current status of a display device indicated in the identified delivery action. In one embodiment, a status of certain display devices may be determined without receiving real-time information from the respective display device. For example, a status schedule indicating statuses of a display device that are associated with various times/dates may be accessed in order to determine a current status of the display device. Similarly, a status rule may indicate that a particular display device is always in night status between 9 p.m. and 9 a.m. Other formats and types of status schedules may also be used.

In one embodiment, the sensor electronics module determines a current status of the display device by requesting status information from the display device. For example, a status request signal may be transmitted to the display device (or to a service provider associated with the display device or another device that maintains updated status information) prior to transmission of the indicated data package. In one embodiment, the status request signal does not cause the display device to perform any functions that are readily detectable by the user of the display device, but only causes the display device to respond to the sensor electronics module with an indication of a current status of the display device. Thus, the sensor electronics module may determine a status of the display device without interrupting the user of the display device in the event that a current status of the display device indicates that the user does not wish to be interrupted with data packages (or at least data packages associated with certain types of alerts). In some embodiments, the display device may transmit an indication of when the current status will change to a different status, such as when a sleep status will change to an awake status. Thus, the sensor electronics module may delay transmission of a data package until the display device is in a status wherein transmission of the data package is appropriate. In other embodiments, a status of a display device may be determined in any other manner.

Moving to block 940, the sensor electronics module determines delivery options associated with the current status of the display device. For example, certain statuses may include no delivery options, such that the delivery options already associated with the delivery action are used in generating the data package. Other statuses, however may include delivery options that limit or expand the content of the displayable sensor information, adjust the formatting of the displayable sensor information, and/or adjust the method by which the displayable sensor information is transmitted to the display device. Accordingly, the user of the display device may customize the displayable sensor information that is delivered to the display device by adjusting a status of the display device.

Continuing to block 950, the sensor electronics module initiates transmission of the data package that is generated according to the delivery options associated with the current status of the display device. In some embodiments, certain statuses may cause the sensor electronics module to not generate a data package for transmission to the delivery device in response.

Next, in block 960, the sensor electronics module determines if additional delivery actions are associated with the triggered alert. For example, certain alerts have multiple associated delivery actions, each indicating delivery options for respective display devices. If the triggered alert is associated with one or more additional delivery actions, the method returns to blocks 920-950 wherein the status of another display device is determined and an appropriate data package, if any, is generated and transmitted.

Figure 10A:
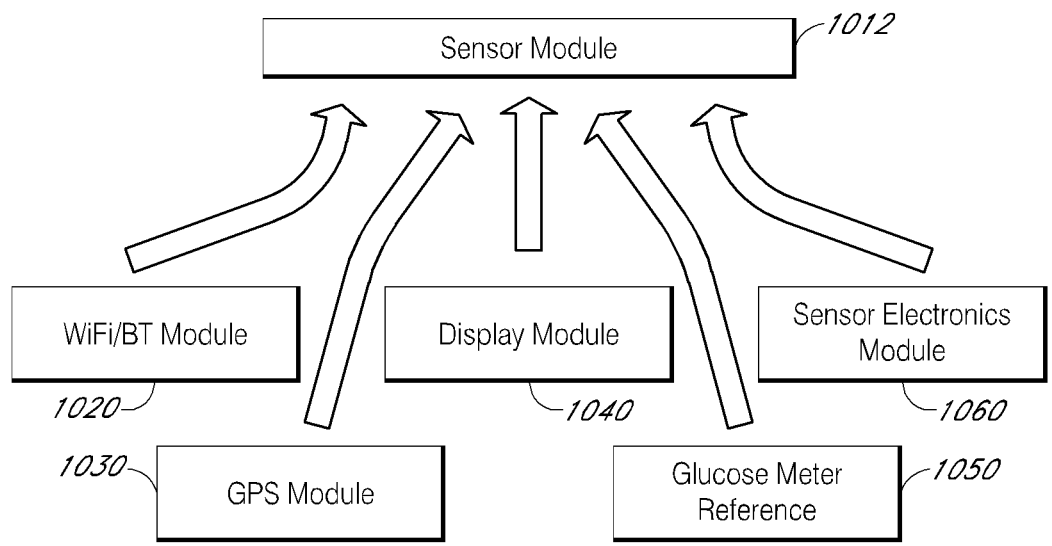
FIGS. 10A and 10B are block diagrams illustrating one embodiment of a sensor module that is configured to alternatively couple with each of a plurality of modular devices each having different functionalities.
Figure 10B:
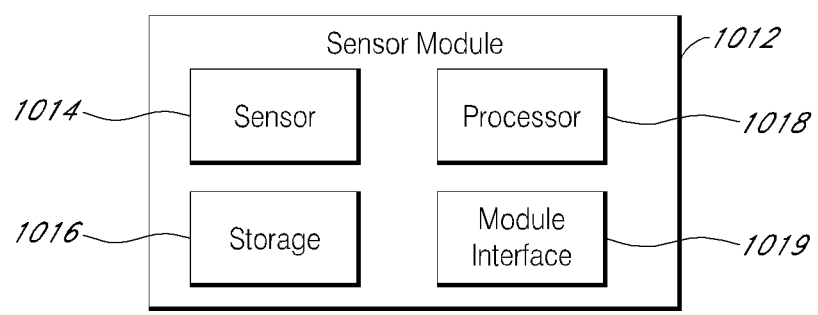

FIGS. 10A and 10B are block diagrams illustrating one embodiment of a sensor module 1012 that is configured to alternatively couple with each of a plurality of modular devices 1020, 1030, 1040, 1050, 1060, and/or other devices, each having different functionalities. FIG. 10A illustrates the sensor module 1012 along with multiple modular devices that may be alternately attached to the sensor module 1000 and FIG. 10B illustrates exemplary components of a sensor module 1012. As illustrated in FIG. 10B, the sensor module 1012 comprises fewer components than the sensor electronics module 12 of FIG. 2, for example. Accordingly, the sensor module 1012 may be a much smaller device that is less bothersome to the host. Advantageously, however, a host may attach modular devices to the sensor module 1004 in order to allow the sensor module 1012 to perform additional functions.

The exemplary sensor module 1012 comprises a sensor 1014, which may be integral to the sensor module 1012 or may be attached to one or more electrodes (or other connection port) of the sensor module 1012. The sensor module 1012 also includes a processor 1018, such as a conventional microprocessor, an ASIC, an FPGA, or any other processing logic, as well as a storage device 1016 that stores sensor data from the sensor 1014 and possibly transformed sensor data that is determined by the processor 1018. In one embodiment, the storage device 1016 is configured to store only a small portion of the data that data storage memory 220 of the sensor electronic module 12 (FIG. 2) is configured to store.

Advantageously, the sensor module 1012 comprises a module interface 1019 comprising both a physical and an electrical interface for coupling with modular devices, such as those of FIG. 10A. For example, the module interface 1019 may be configured such that a modular device may releasably lock into attachment with the sensor module 1012. Additionally, in certain embodiments the coupling of the modular devices with the module interface 1019 causes one or more electrical contacts of each component to engage in order to communicate data between the sensor module 1012 and the respective modular device.

Modular devices that may be coupled to the sensor module 1012 vary greatly and may include a Wi-Fi/Bluetooth module 1020 that is configured to add additional communication capabilities to the sensor module 1012. In other embodiments, the module 1020 may be configured to communicate using additional communication protocols. With the module 1020 attached to the sensor module 1012, the sensor module 1012 may transmit data packages, such as in response to triggered alerts, to one or more display devices using Wi-Fi, ANT and/or Bluetooth communications. Another modular device is a GPS module 1030 that provides location data to the sensor module 1012. As described above, in certain embodiments location conditions are included in alert conditions for certain alerts and might be included in displayable sensor information that is transmitted to one or more display devices. Thus, the sensor module 1012 may use the location data from the GPS module 1030 in order to determine if such alert conditions have been met.

Modular devices that may be attached to the sensor module 1012 may also include a display device 1040, which may include any size of display panel, such as an LCD or OLED display, for example. Depending on the embodiment, the display module 1040 may be able to display different types of displayable sensor information formatted using various formatting options. A sensor electronics module 1060 comprising additional processing logic, data storage space, and user interface controls, for example, may also be removably coupled to the sensor module 1012. Depending on embodiment, the sensor electronics module 1060 may have all, or some subset of, the features discussed herein with respect to other sensor electronics modules. In one embodiment, a glucose meter reference module 1050 may be coupled to the sensor module 1012. The glucose meter reference module 1050 may be configured to determine a reference glucose level of the host in order to calibrate the sensor data received from the sensor 1014.

In one embodiment, the sensor module 1012 also includes an alarm device, such as a light or speaker that is activated in response to triggering of certain alerts. Thus, if an alert is triggered, such as based on sensor data and/or GPS location data provided by the GPS module 1030, the sensor module 1012 may activate a light of the sensor module 1012 in order to alert the host to the triggering of the alarm. Depending on embodiment, different patterns of activation/deactivation of the light and/or speaker may be used to indicate triggering of different alerts.

FIG. 11 illustrates an exemplary user interface 1100 for defining alert conditions. In one embodiment, default alert conditions (e.g., that might be set by a manufacturer of the sensor electronics module) are used in determining whether alerts have been triggered. In other embodiments, a user of the sensor electronics module, such as the host or a guardian of the host, for example, may establish custom alerts having user-defined alert conditions. In the embodiment of FIG. 11, the user provides an alert ID 1110 and minimum and/or maximum threshold levels for each of one or more sensors data or transformed sensor data. In embodiment of FIG. 11, alert conditions for three sensors, namely, a glucose sensor, a temperature sensor and a pulse sensor, may be established. In other embodiments, fewer or additional sensors may be included in a similar user interface in order to allow defining alert conditions based on those sensors.

The exemplary user interface 1100 includes a glucose conditions portion 1120, a temperature conditions portions 1130, and a pulse conditions portion 1140, where each of the portions allow the user to set conditions associated with the respective sensor data and/or transformed sensor data. In the embodiment of FIG. 11, the alert ID provided by the user is "Hypo1", which may be triggered in order to indicate that the host is approaching hypoglycemia. In this embodiment, the user has set a glucose condition requiring that the glucose level is less than 70 mg/dL and that a rate of change of the glucose level (in mg/dL/min) is less than five. Each of these conditions associated with a glucose sensor data must be met in order for the Hypo1 alert to trigger. In the example of FIG. 11, the user interface 1100 does not include any conditions associated with a temperature sensor. However, in other embodiments alert conditions associated with a current temperature of the host, temperature change trends, and/or any other transformed sensor data associated with a temperature sensor, may be included in an alert condition.

The pulse conditions portion 1140 indicates that the pulse of the host must be below 80 beats per minute and the pulse must have changed at least 15 beats per minute over the last five minutes. Accordingly, based on the conditions indicated in exemplary FIG. 11, the Hypo1 alert is triggered when the glucose level of the host is 70 or below, the glucose rate of change is five or below, the pulse is 80 or below, and the pulse has changed at least 15 beats per minute over a five minute period. In other embodiments, other conditions associated with other sensors may be established in a similar manner. Once the user is satisfied with the alert conditions, a save button 1150 may be selected in order to store the newly defined alert in a data structure that is accessible to the sensor electronics module.

Figure 12:
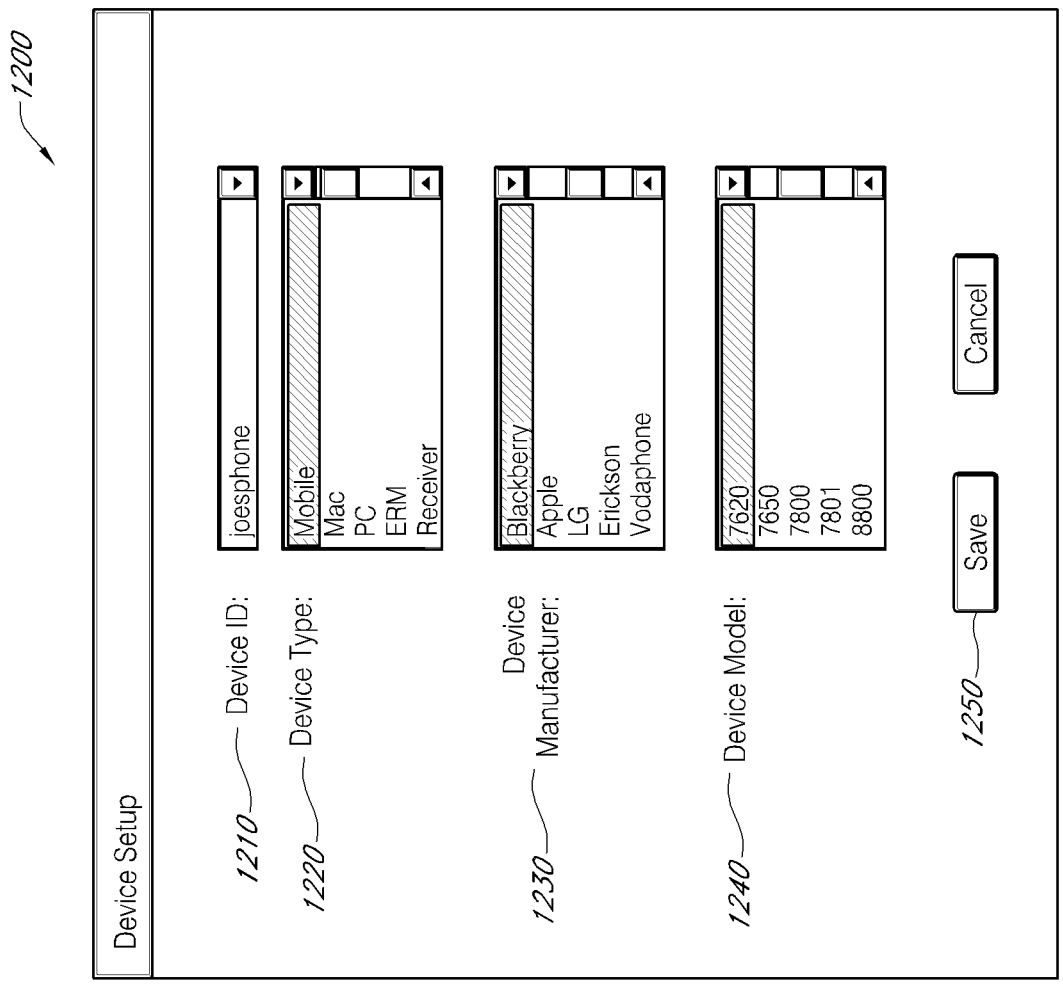
FIG. 12 illustrates an exemplary user interface for defining display device characteristics.

FIG. 12 illustrates an exemplary user interface 1200 for defining display device characteristics. In certain embodiments, delivery options are determined based on a type, make, model, or other characteristic of a display device. Thus, in certain embodiments, characteristics of display devices that are available to receive data packages from the sensor electronics module may be defined so that the sensor electronics module may determined delivery options for respective display devices. Additionally, in certain embodiments alert conditions may be based on one or more characteristics of a display device.

In the embodiment of FIG. 12, a user supplies a device ID 1210, a device type 1220, a device manufacturer 1230, and a device model 1240 via any suitable data entry controls. For example, a device type may be provided via a drop-down list wherein the user can select a type of display device from a series of listed display devices. Similarly, a device manufacturer and device model may be selected by drop-down lists where the options illustrated in the drop-down lists are narrowed as more general information regarding the device is received. For example, once a user selects a device type, the choices of device manufacturers may be narrowed to only those device manufacturers that manufacture the selected device type. In other embodiments, fewer or additional device characteristics may be provided by the user. When the appropriate device characteristics are selected, the user selects a save button 1250 that initiates the storage of the device characteristics in a data structure that is accessible by the sensor electronics module.

Figure 13:
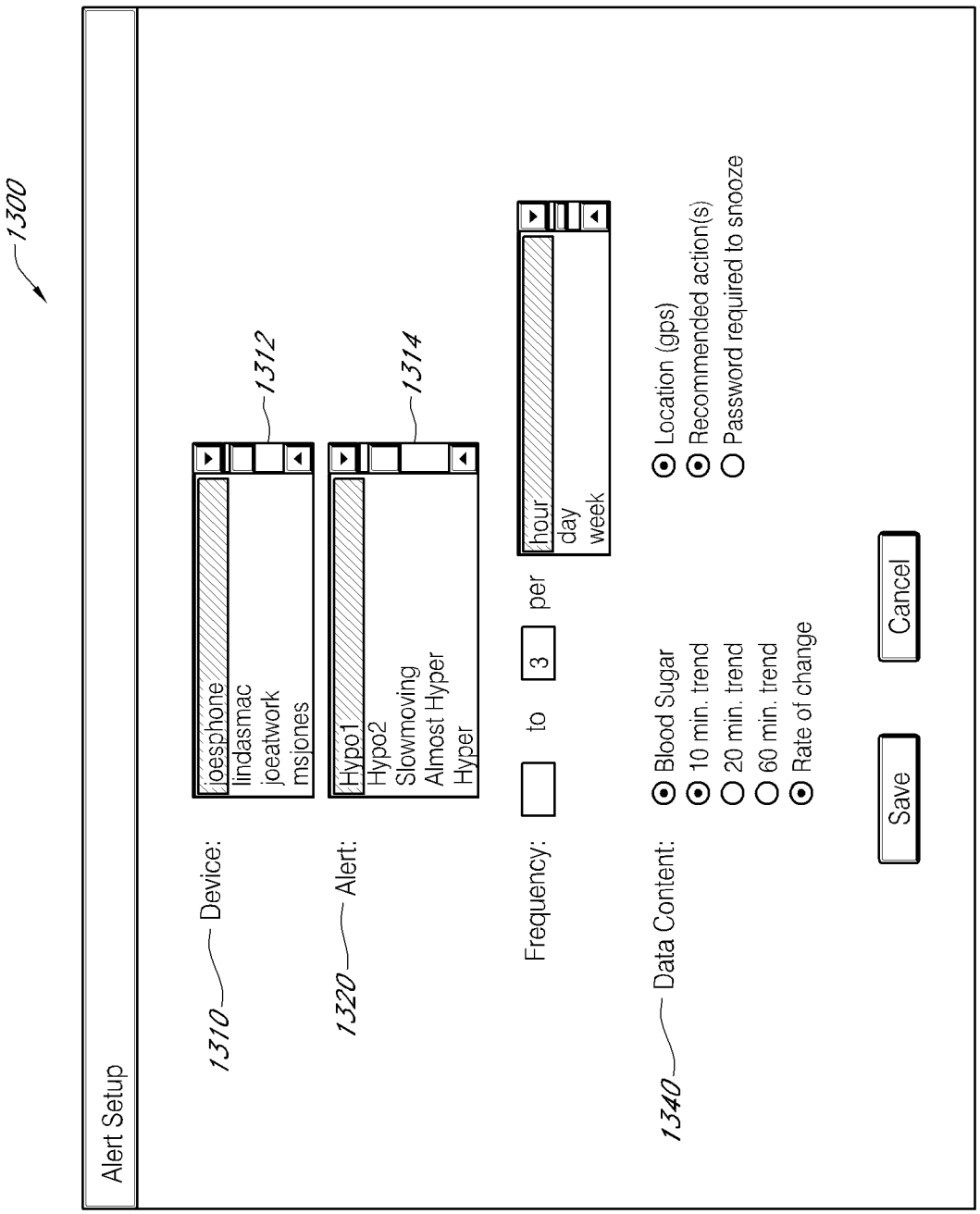
FIG. 13 illustrates an exemplary user interface for establishing delivery options associated with respective alerts and display devices.

FIG. 13 illustrates an exemplary user interface 1300 for establishing delivery options associated with respective alerts and display devices. Using the user interface 1300, delivery options may be established for respective display devices that are associated with respective alerts, such as customized alerts and/or default alerts. In the embodiment of FIG. 13, a display device and an alert are selected in the device selection portion 1310 and alert selection portion 1320, respectively. In this embodiment, the devices that have been set up by a user, such as via a user interface similar to that of FIG. 12, are listed in a drop-down box 1312. Similarly, the alerts that have been established by the user, such as via the alert conditions interface 1100 of FIG. 11 and/or other default alerts are displayed for selection in an alert drop-down box 1314.

In the exemplary user interface 1300, the user has selected the "joesphone" display device to receive a data package in response to triggering of the Hypo1 alert. The lower portion of the user interface 1300 allows the user to establish delivery options, such as which sensor data and/or transformed sensor data should be included in the displayable sensor information that is transmitted to the selected display device. In this embodiment, the user may select a minimum and/or maximum frequency at which data packages associated with the selected alert should be transmitted to the selected display device. The frequency of sending alerts may change depending on one or more attributes of the sample data, the triggered alert, actions taken by the host in response to the alert, a status of the host or display device, and any other characteristic of the host. For example, a data package associated with a severe hypoglycemia condition may be transmitted frequently (e.g., every 5 minutes), while a data package associated with a near hypoglycemia condition may be transmitted only once each hour (assuming the alert conditions associated with near hypoglycemia are still matched by the sensor data at each one hour interval). Additionally, the frequency of retransmitting data packages associated with an alert may accelerate (or decelerate) over time, such as sending a severe hypoglycemia data package every minute for the first 10 minutes after the alert conditions are matched and thereafter sending a data package every 5 minutes. Depending on the embodiment, (re)transmissions of data packages that are associated with delivery options indicating multiple (re)transmissions of the data packages may be delayed and/or halted in response to triggering of other alerts associated with the host, performing of an action by the host, or actions by the receiving display device. For example, delivery options may indicate that data packages associated with a hyperglycemic condition are stopped in response to the host receiving insulin (either manually or automatically). Additionally, a user of a particular display device may indicate that they do not wish to receive further data packages associated with a triggered alert, such as after receiving a first data package including information regarding the triggered alert.

Additionally, the user may select displayable sensor information that will be transmitted to be selected display device in response to triggering of the selected alert. The data content portion 1340 lists only a few of the content items that may be selected for inclusion in displayable sensor information that is transmitted to the display device. In other embodiments, the format of the selected data content may also be established in a user interface similar to that of FIG. 13. For example, a user may indicate whether a five-minute trend information should be formatted as a line graph, bar graph, pie graph, or in some other format. Accordingly, the user is provided great flexibility in how the sensor electronics module transmits data to each of multiple display devices.

FIG. 14A illustrates a portion of an exemplary alert data structure 1400. Although the data structures discussed herein are illustrated in a particular arrangement in the corresponding drawings, the data structures may include any other type and/or format of data structure, such as a database, a table, a flat file, a spreadsheet file, or any other file that stores data. In the embodiment of FIG. 14A, the data structure 1400 includes an alert ID column 1410, a display device address column 1420, a device type column 1430, and a frequency column 1440. In this embodiment, when an alert is triggered, such as the alerts listed in column 1410, a delivery action is initiated, wherein a generated data package is transmitted to each of the delivery addresses listed in column 1420 that are associated with the triggered alert. In this embodiment, the delivery options associated with respective data packages are determined based on the device type listed in column 1430. For example, FIG. 14B illustrates a delivery options data structure 1450 that indicates particular data content to include in the transmitted displayable sensor information based on the device type indicated in column 1430. For example, the exemplary delivery options data structure 1450 indicates that for a mobile device type, the displayable sensor information includes a 10 minute trend and a one hour trend. In other embodiments, the delivery options data structure also includes formatting options for particular content.

Returning to FIG. 14A, the frequency column 1440 indicates a maximum (and/or minimum) frequency at which data packages should be transmitted to the corresponding delivery addresses (in column 1420, for example). Thus, the hypoglycemic alert of FIG. 14 triggers a delivery action to six different delivery addresses, including Joe@MSN.com, Linda@e-mail.com, ftp://admin:pass@123.12.12.42, etc. Thus, when the hypoglycemic alert is triggered, data packages comprising displayable sensor information that is selected based on a type of display to which the data package is to be sent are generated. Accordingly, the data package that is delivered to joe@MSN.com is generated based on the display device characteristics for a mobile device, such as those in column 1460 of FIG. 14B. Similarly, the delivery options for the data package that is transmitted to Linda@e-mail.com, which column 1430 indicates is associated with a PC, are determined based on the delivery options of column 1470 in FIG. 14B.

FIGS. 15A and 15B illustrate exemplary data structures that may be used to establish alerts, detect when alert conditions are met, and generate customized data packages for different display devices based on one or more of multiple factors. FIG. 15A illustrates a device data structure 1500 that stores device characteristics associated with each of one or more device IDs. In one embodiment, the data of FIG. 15A is provided by a user via a user interface, such as user interface of FIG. 12. The exemplary data structure 1500 comprises a device ID column 1510 that lists a device ID that is specific to a particular display device, a device address column 1512 that indicates an address to which the data package for the corresponding display device should be delivered, a device type column 1514 that indicates a type of device, and a device model column 1516 that indicates a model of the particular device. In other embodiments, fewer or additional characteristics of the devices may be included in a similar data structure.

FIG. 15B illustrates an alert data structure 1520 that provides alert actions corresponding with each of a plurality of alerts, as well as delivery options for specific display devices indicated in the alert actions. In particular, the data structure 1520 includes an alert column 1522 that includes an alert ID of the alerts for which alert actions are to be performed. An alert action column 1524 lists an action that should be performed when the corresponding alert is triggered, such as a device ID associated with a delivery action. In this embodiment, the device characteristics may be determined by accessing the data structure of 15A, for example. The data structure 1520 also includes a plurality of delivery options in columns 1530. As discussed above, delivery options may include indications of the content of sensor data and/or transformed sensor data that should be included in the displayable sensor information transmitted to a display device, as well as limits on the frequency at which such data packages are transmitted to the display device, and/or formatting options for the displayable sensor information.

FIG. 16 is a multi-sensor alert data structure 1600 storing alert conditions associated with multiple sensors in alert conditions section 1610. Thus, the data structure of FIG. 16 defines alert conditions in columns 1610 and includes a device ID and column 1620 that may be used to indicate display device and specific delivery options for delivery of data packages in response to triggering of alerts. In one embodiment, delivery options may also be customized based on the type of device to which a data package is transmitted, where device characteristics may be determined using a table such as that of FIG. 15A.

In other embodiments, various other arrangements of data may be utilized to allow the sensor electronics module to customize displayable sensor data for each of a plurality of display devices in response to triggering of alerts (that may be customized also).

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; 7,110,803; 7,192,450; 7,226,978; and 7,310,544.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No.

US-2005-0154271-A1; U.S. Patent Publication No.
US-2004-0199059-A1; U.S. Patent Publication No.
US-2005-0054909-A1; U.S. Patent Publication No.
US-2005-0051427-A1; U.S. Patent Publication No.
US-2003-0032874-A1; U.S. Patent Publication No.
US-2005-0103625-A1; U.S. Patent Publication No.
US-2005-0203360-A1; U.S. Patent Publication No.
US-2005-0090607-A1; U.S. Patent Publication No.
US-2005-0187720-A1; U.S. Patent Publication No.
US-2005-0161346-A1; U.S. Patent Publication No.
US-2006-0015020-A1; U.S. Patent Publication No.
US-2005-0043598-A1; U.S. Patent Publication No.
US-2005-0033132-A1; U.S. Patent Publication No.
US-2005-0031689-A1; U.S. Patent Publication No.
US-2004-0186362-A1; U.S. Patent Publication No.
US-2005-0027463-A1; U.S. Patent Publication No.
US-2005-0027181-A1; U.S. Patent Publication No.
US-2005-0027180-A1; U.S. Patent Publication No.
US-2006-0020187-A1; U.S. Patent Publication No.
US-2006-0036142-A1; U.S. Patent Publication No.
US-2006-0020192-A1; U.S. Patent Publication No.
US-2006-0036143-A1; U.S. Patent Publication No.
US-2006-0036140-A1; U.S. Patent Publication No.
US-2006-0019327-A1; U.S. Patent Publication No.
US-2006-0020186-A1; U.S. Patent Publication No.
US-2006-0036139-A1; U.S. Patent Publication No.
US-2006-0020191-A1; U.S. Patent Publication No.
US-2006-0020188-A1; U.S. Patent Publication No.
US-2006-0036141-A1; U.S. Patent Publication No.
US-2006-0020190-A1; U.S. Patent Publication No.
US-2006-0036145-A1; U.S. Patent Publication No.
US-2006-0036144-A1; U.S. Patent Publication No.
US-2006-0016700-A1; U.S. Patent Publication No.
US-2006-0142651-A1; U.S. Patent Publication No.
US-2006-0086624-A1; U.S. Patent Publication No.
US-2006-0068208-A1; U.S. Patent Publication No.
US-2006-0040402-A1; U.S. Patent Publication No.
US-2006-0036142-A1; U.S. Patent Publication No.
US-2006-0036141-A1; U.S. Patent Publication No.
US-2006-0036143-A1; U.S. Patent Publication No.
US-2006-0036140-A1; U.S. Patent Publication No.
US-2006-0036139-A1; U.S. Patent Publication No.
US-2006-0142651-A1; U.S. Patent Publication No.
US-2006-0036145-A1; U.S. Patent Publication No.
US-2006-0036144-A1; U.S. Patent Publication No.
US-2006-0200022-A1; U.S. Patent Publication No.
US-2006-0198864-A1; U.S. Patent Publication No.
US-2006-0200019-A1; U.S. Patent Publication No.
US-2006-0189856-A1; U.S. Patent Publication No.
US-2006-0200020-A1; U.S. Patent Publication No.
US-2006-0200970-A1; U.S. Patent Publication No.
US-2006-0183984-A1; U.S. Patent Publication No.
US-2006-0183985-A1; U.S. Patent Publication No.
US-2006-0195029-A1; U.S. Patent Publication No.
US-2006-0229512-A1; U.S. Patent Publication No.
US-2006-0222566-A1; U.S. Patent Publication No.
US-2007-0032706-A1; U.S. Patent Publication No.
US-2007-0016381-A1; U.S. Patent Publication No.
US-2007-0027370-A1; U.S. Patent Publication No.
US-2007-0027384-A1; U.S. Patent Publication No.
US-2007-0032717-A1; U.S. Patent Publication No.
US-2007-0032718-A1; U.S. Patent Publication No.
US-2007-0059196-A1; U.S. Patent Publication No.
US-2007-0066873-A1; U.S. Patent Publication No.
US-2007-0093704-A1; U.S. Patent Publication No.
US-2007-0197890-A1; U.S. Patent Publication No.
US-2007-0173710-A1; U.S. Patent Publication No.
US-2007-0163880-A1; U.S. Patent Publication No.
US-2007-0203966-A1; U.S. Patent Publication No.
US-2007-0213611-A1; U.S. Patent Publication No.
US-2007-0232879-A1; U.S. Patent Publication No.
US-2007-0235331-A1; U.S. Patent Publication No.
US-2008-0021666-A1; and U.S. Patent Publication No.
US-2008-0033254-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/543,396 filed Oct. 4, 2006 and entitled "ANALYTE SENSOR"; U.S. patent application Ser. No. 11/543,490 filed Oct. 4, 2006 and entitled "ANALYTE SENSOR"; U.S. patent application Ser. No. 11/543,404 filed Oct. 4, 2006 and entitled "ANALYTE SENSOR"; U.S. patent application Ser. No. 11/691,426 filed Mar. 26, 2007 and entitled "ANALYTE SENSOR"; U.S. patent application Ser. No. 11/691,432 filed Mar. 26, 2007 and entitled "ANALYTE SENSOR"; U.S. patent application Ser. No. 11/691,424 filed Mar. 26, 2007 and entitled "ANALYTE SENSOR"; and U.S. patent application Ser. No. 11/691,466 filed Mar. 26, 2007 and entitled "ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method of monitoring analyte concentration levels in a host, the method comprising:
 downloading first software to a first mobile phone to configure the first mobile phone to display sensor information derived at least in part from sensor data obtained by sensor electronics connected to a transcutaneous analyte sensor that is implanted in the host;

using the first downloaded software, generating a user interface on the first mobile phone;

receiving input of an identifier of at least one additional recipient of at least some of the sensor information into the generated user interface, wherein one recipient of the at least one additional recipient is associated with a second mobile phone hosting second downloaded software;

based at least in part on the receiving of the input, establishing a communication path specific to the one recipient of the at least one additional recipient that is used for transmission of the at least some of the sensor information from the first downloaded software to the second downloaded software in real-time once the first downloaded software has obtained the sensor information from the sensor electronics;

using the first downloaded software, obtaining the sensor information from the sensor electronics and displaying the sensor information on the first mobile phone; and once the first mobile phone has obtained the sensor information, using the first downloaded software to send one or more data packets containing the at least some of the sensor information over the established communication path to the second downloaded software so that information associated with the at least some of the sensor information is displayable on the second mobile phone to the one recipient of the at least one additional recipient using the second downloaded software.

2. The method of claim 1, wherein the communication path comprises the Internet.

3. The method of claim 1, wherein the information associated with the at least some of the sensor information is displayed on the second mobile phone with or without additional processing.

4. The method of claim 1, wherein the identifier is associated with a device type.

5. The method of claim 4, wherein the second downloaded software comprises a mobile app.

6. The method of claim 1, comprising querying the sensor electronics with the first mobile phone for at least some of the sensor information.

7. The method of claim 6, further comprising using a first communication protocol including magnetic induction for the querying of the at least some of the sensor information by the first mobile phone.

8. The method of claim 7, comprising transmitting data associated with the at least some of the queried sensor information from the first mobile phone using a second communication protocol.

9. The method of claim 8, wherein the second communication protocol includes a WiFi or a cellular wireless protocol.

10. The method of claim 1, wherein the receiving of the input causes-selective authorization of the at least one additional recipient to remotely receive and view the at least some of the sensor information during one or more sensor sessions of the host.

11. The method of claim 1, wherein the communication path is usable for communicating the at least some of the sensor information from the first downloaded software to the second downloaded software over a period of a day or more.

12. The method of claim 1, comprising receiving by the first mobile phone from the sensor electronics via a first wireless communication protocol the sensor information and transmitting by the first mobile phone via a second wireless communication protocol data associated with the at least some of the received sensor information, wherein the first wireless communication protocol is different than the second wireless communication protocol.

13. A method of monitoring analyte concentration levels in a host, the method comprising:

downloading first software to a first mobile phone to configure the first mobile phone to display sensor information derived at least in part from sensor data obtained from sensor electronics connected to a transcutaneous analyte sensor that is implanted in the host;

using the first downloaded software, generating a user interface on the first mobile phone;

receiving input of an identifier of at least one additional recipient of at least some of the sensor information into the generated user interface, wherein one recipient of the at least one additional recipient is associated with a second mobile phone hosting second downloaded software;

based at least in part on the receiving of the input, establishing a communication path specific to the one recipient of the at least one additional recipient that is used for transmission of the at least some of the sensor information from the first downloaded software to the second downloaded software in real-time once the first downloaded software has obtained the sensor data from the sensor electronics;

using the first downloaded software, obtaining the sensor data from the sensor electronics and displaying the sensor information on the first mobile phone; and once the first mobile phone has obtained the sensor data, using the first downloaded software to send one or more data packets containing the at least some of the sensor information over the established communication path to the second downloaded software so that information associated with the at least some of the sensor information is displayable on the second mobile phone to the one recipient of the at least one additional recipient using the second downloaded software.

14. The method of claim 13, wherein the communication path comprises the Internet.

15. The method of claim 13, wherein the information associated with the at least some of the sensor information is displayed on the second mobile phone with or without additional processing.

16. The method of claim 13, wherein the identifier is associated with a device type.

17. The method of claim 16, wherein the second downloaded software comprises a mobile app.

18. The method of claim 13, comprising querying the sensor electronics with the first mobile phone for at least some of the sensor data.

19. The method of claim 18, further comprising using a first communication protocol including magnetic induction for the querying of the at least some of the sensor data by the first mobile phone.

20. The method of claim 19, comprising transmitting sensor information associated with the at least some of the queried sensor data from the first mobile phone using a second communication protocol.

21. The method of claim 20, wherein the second communication protocol includes a WiFi or a cellular wireless protocol.

22. The method of claim 13, wherein the receiving of the input causes-selective authorization of the at least one additional recipient to remotely receive and view the at least some of the sensor information during one or more sensor sessions of the host.

23. The method of claim 13, wherein the communication path is usable for communicating the at least some of the sensor information from the first downloaded software to the second downloaded software over a period of a day or more.

24. The method of claim 13, comprising receiving by the first mobile phone from the sensor electronics via a first wireless communication protocol the sensor data and transmitting by the first mobile phone via a second wireless communication protocol informatior associated with the at least some of the sensor information, wherein the first wireless communication protocol is different than the second wireless communication protocol.

* * * * *